United States Patent
Oguri et al.

(10) Patent No.: US 6,338,955 B2
(45) Date of Patent: *Jan. 15, 2002

(54) β1-4 N-ACETYLGLUCOSAMINYLTRANSFERASE AND GENE ENCODING

(75) Inventors: Suguru Oguri, Hokkaido; Mari Minowa; Aruto Yoshida, both of Kanagawa; Naoyuki Taniguchi, Osaka; Makoto Takeuchi, Kanagawa, all of (JP)

(73) Assignee: Kirin Beer Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,860
(22) PCT Filed: Dec. 10, 1997
(86) PCT No.: PCT/JP97/04546
§ 371 Date: Aug. 12, 1998
§ 102(e) Date: Aug. 12, 1998
(87) PCT Pub. No.: WO98/26053
PCT Pub. Date: Jun. 18, 1998

(30) Foreign Application Priority Data

Dec. 12, 1996 (JP) ............................................ 8/332411
Jun. 18, 1997 (JP) ............................................ 9/161462

(51) Int. Cl.⁷ .......................... C12N 15/54; C12N 9/10; C12P 19/18
(52) U.S. Cl. ....................... 435/97; 435/193; 435/320.1; 435/325; 435/252.3; 536/23.2
(58) Field of Search ............................. 435/193, 320.1, 435/325, 252.3, 97; 536/23.2

(56) References Cited

FOREIGN PATENT DOCUMENTS

EP           585 083        * 3/1994

OTHER PUBLICATIONS

S. Oguri et al. "Purification and Characterization of a New N-Acetylglucosaminyl Transferase", Glycoconjugate J. 14(6): 767, Abstract P20., Mar. 1997.*

S. Oguri et al. Purification and Characterization of UDP--N-Acetylglucosamine: alpha 1,3–D–Mannoside β1,4N–Acetylglucosaminyltransferase (N–Acetylglucosaminyltransferase–IV) From Bovine Small Intestine, J. Biol. Chem. 272(36): 22721–22727, Sep. 1997.*

Makoto Takeuchi, "Glycobiology Series 5: Glycotechnology", Kihata, Hakomori and Nagai (eds.), Kodansha Scientific Co., (1994), 191–208 English Abstract provided see attached 1.

(List continued on next page.)

Primary Examiner—Rebecca E. Prouty
(74) Attorney, Agent, or Firm—Foley & Lardner

(57) ABSTRACT

The present invention relates to a novel enzyme having β1→4 N-acetylglucosaminyltransferase (GnT-IV) activity; a gene encoding the enzyme; a recombinant DNA comprising the gene; a host cell comprising the recombinant DNA; a method for producing an enzyme protein having GnT-IV activity comprising culturing the host cell in a medium; and a saccharide in which the sugar chain is modified using a GnT-IV.

According to the present invention, a novel GnT-IV, a method for producing the enzyme and a gene coding for the enzyme are provided. With the GnT-IV of the present invention, it has become possible to produce a saccharide having a branching structure which could not be formed with conventional glycosyltransferases. Thus, the GnT-IV of the invention is useful not only for producing or improving glycoconjugate type pharmaceuticals, reagents and foods, but also for modifying the sugar chain structure of any biopolymer.

72 Claims, 17 Drawing Sheets

Positions of GlcNAc transfer by various GlcNAc Transferases

OTHER PUBLICATIONS

Hiroshi Nakajima, Sugar Chain Technology, Industry Survey Association (1992), 384–397 English Abstract provided see attached 2.

Kiyoshi Furukawa, Sugar Chain Technology, Industry Survey Association (1992), 64–75 English Abstract provided see attached 3.

Mouritsen et al., Eur. J. Immunol., (1994), 24, 1066–1072.

Takeuchi et al., Glycobiology, (1991), 1, 337–346.

Takeuchi et al., Proc. Natl. Acad. Sci. USA, (1989), 86, 7819–22.

Misaizu et al. Blood, (1995), 86, 4097–4104.

Toshihiro Kawasaki, Sugar Chain Technology, Industry Survey Association (1992), 125–136 English Abstract provided see attached 8.

Tatsuo Irimura, "Glycobiology Series 3: Glycobiology in Cell Society", Nagai et al. (eds.) Kodansha Scientific Co., (1993), 127–175 English Abstract provided see attached 9.

Kato et al., "Sugar Chain Technology and Development of Pharmaceutical", Foundation for the Relief and Study of Injury Caused by Pharmaceutical Side Effect (ed.) Yakugyo–Jiho–Sha, (1994), 107–132 English Abstract provided see attached 10.

Katsuko Yamashita, Protein, Nucleic Acid and Enzyme (1992), 37, 1880–1888 English Abstract provided see attached 11.

Yamashita et al., J. Biochem., (1989), 105, 728–735.

Takasaki et al., Biochem. Biophys. Res. Commun. (1980), 90, (3), 735–742.

Glesson et al., J. Biol. Chem., (1983), 258, 6162–6173.

Kumar et al., Proc. Natl. Acad. Sci. USA (1990), 87, 9948–9952.

Sarkar et al. Proc. Natl. Acad. Sci., USA, (1991), 88, 234–238.

D'Agostaro, J. Biol. Chem., (1995), 270, 15211–21.

Nishikawa et al., J. Biol. Chem., (1992), 267, 18199–18204.

Shorebah et al., J. Biol. Chem., (1992), 267, 2920–2927.

Gu et al., J. Biochem, (1993), 113, 614–619.

Yoshima et al., J. Biol. Chem., (1981), 256, 8476–8484.

Takeuchi et al., J. Biol. Chem., (1990), 265, 12127–12130.

Bierhuizen et al., J. Biol. Chem., (1994), 269, 4473–4479.

Kawashima et al. J. Biol. Chem., (1993), 268, 27118–27126.

Bierhuizen et al., Genes Dev., (1993), 7, 468–478.

Minowa et al., "Cloning and expression of a newly purified N–acetylglucosaminyl transferase", p. 767 Glycoconjugate J 14(6) (1997).

* cited by examiner

Biosynthetic Pathways of Asn-Linked Sugar Chains

FIG.2
Variations of Asn-Linked Sugar Chains
[Revised from Fig.1, Makoto Takeuchi, Wako Purechemical Newsletter 64, 18-19, 1996]
a. Mannan type
b. Xylo-high-mannose type
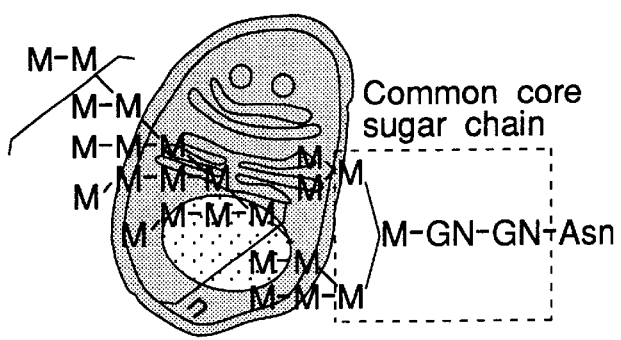
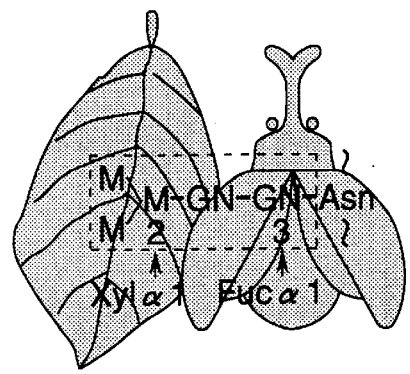
c. High mannose type
d. Hybrid type
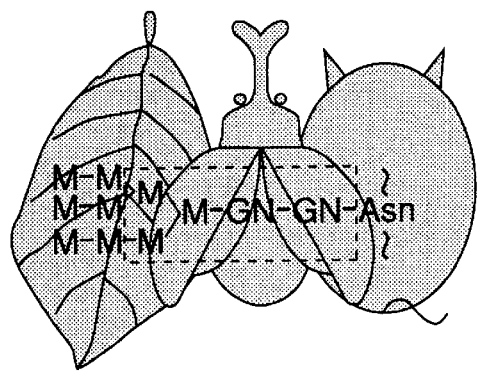
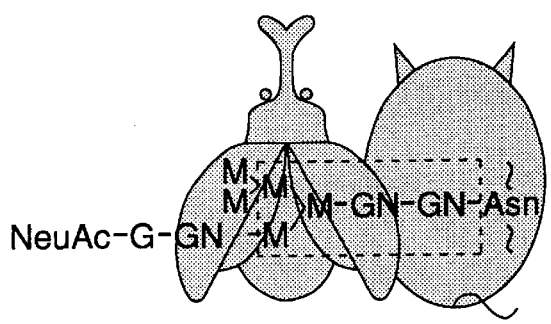
e. Complex type
f. Prokaryotic cell
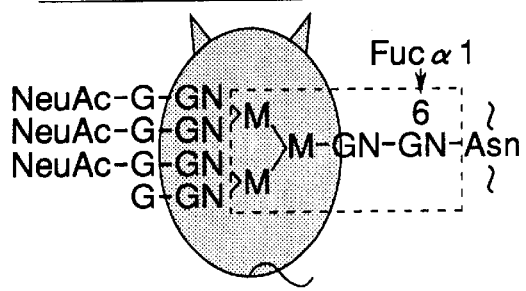
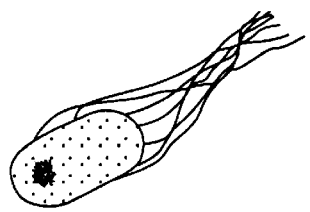

Positions of GlcNAc transfer by various GlcNAc Transferases

FIG.4

Structures and Designations of Oligosaccharides

Manα1→6
         \
          Manβ1→4GlcNAcβ1→4GlcNAc-PA  (Core type oligosaccharide)
         /
Manα1→3

                    Manα1→6
                           \
                            Manβ1→4GlcNAcβ1→4GlcNAc-PA
                           /
GlcNAcβ1→2Manα1→3
                    (GnT-I product type oligosaccharide)

GlcNAcβ1→2Manα1→6
                 \
                  Manβ1→4GlcNAcβ1→4GlcNAc-PA
                 /
GlcNAcβ1→2Manα1→3
                 (GnT-II product type oligosaccharide)

GlcNAcβ1→6
          \
           Manα1→6
                  \
                   Manβ1→4GlcNAcβ1→4GlcNAc-PA
GlcNAcβ1→2       /
          \     /
           Manα1→3
GlcNAcβ1→2/
          (GnT-V product type oligosaccharide)

GlcNAcβ1→2Manα1→6
                 \
                  Manβ1→4GlcNAcβ1→4GlcNAc-PA
GlcNAcβ1→4      /
          \    /
           Manα1→3
GlcNAcβ1→2/
          (GnT-IV product type oligosaccharide)

Q Sepharose FF Chromatography

Cu Chelate Sepharose FF Chromatography

UDP-Hexanolamine Agarose Affinity Chromatography I

UDP-Hexanolamine Agarose Affinity Chromatography II

Sephadex 200 Gel Chromatography

SDS-PAGE of Purified GnT-IV

Native Gel Electrophoresis and Activity of purified GnT-IV

Smith Degradation of GnT-IV, V and VI Product Type Oligosaccharides $^1$H-NMR (at 30°C) of GnT-IV Reaction Product Optimum pH for GnT-IV Optimum Mn²⁺ Concentration for GnT-IV Activity of GnT-IV on Glycoproteins Open Reading Frame of Human GnT-IVa and the Region Contained in pCore-His Expression Vector

SEQUENCE LISTING

<160> NUMBER OF SEQ ID NOS: 63

<210> SEQ ID NO 1
<211> LENGTH: 8
<212> TYPE: PRT
<213> ORGANISM: Bovine

<400> SEQUENCE: 1

Asp Asn Leu Tyr Pro Glu Glu Lys
 1               5

<210> SEQ ID NO 2
<211> LENGTH: 11
<212> TYPE: PRT
<213> ORGANISM: Bovine

<400> SEQUENCE: 2

Asp Tyr Val Asn Gly Val Val Ala Asn Glu Lys
 1               5                  10

<210> SEQ ID NO 3
<211> LENGTH: 21
<212> TYPE: PRT
<213> ORGANISM: Bovine

<400> SEQUENCE: 3

```
Glu Ile Ser Ser Gly Leu Val Glu Ile Ser Pro Pro Glu Ser Tyr
 1               5                  10                  15

Tyr Pro Asp Leu Thr
            20

<210> SEQ ID NO 4
<211> LENGTH: 8
<212> TYPE: PRT
<213> ORGANISM: Bovine

<400> SEQUENCE: 4

Glu Arg Val Arg Trp Arg Thr Lys
 1               5

<210> SEQ ID NO 5
<211> LENGTH: 15
<212> TYPE: PRT
<213> ORGANISM: Bovine

<400> SEQUENCE: 5

Lys Gln Asn Leu Asp Tyr Cys Phe Leu Met Met Tyr Ala Gln Glu
 1               5                  10                  15

<210> SEQ ID NO 6
<211> LENGTH: 6
<212> TYPE: PRT
<213> ORGANISM: Bovine

<400> SEQUENCE: 6

Asp His Ile Leu Trp Val
 1               5

<210> SEQ ID NO 7
<211> LENGTH: 14
<212> TYPE: PRT
<213> ORGANISM: Bovine

<400> SEQUENCE: 7

Lys Ile His Val Asn Pro Pro Ala Glu Val Ser Thr Ser Leu
 1               5                  10

<210> SEQ ID NO 8
<211> LENGTH: 10
<212> TYPE: PRT
<213> ORGANISM: Bovine

<400> SEQUENCE: 8

Lys Val Tyr Gln Gly His Thr Leu Glu Lys
 1               5                  10

<210> SEQ ID NO 9
<211> LENGTH: 10
<212> TYPE: PRT
<213> ORGANISM: Bovine

<400> SEQUENCE: 9

Asp Phe Phe Trp Ala Ile Thr Pro Val Ala
 1               5                  10

<210> SEQ ID NO 10
<211> LENGTH: 6
<212> TYPE: PRT
<213> ORGANISM: Bovine

<400> SEQUENCE: 10
```

Asp Tyr Ile Leu Phe Lys
1               5

<210> SEQ ID NO 11
<211> LENGTH: 15
<212> TYPE: PRT
<213> ORGANISM: Bovine

<400> SEQUENCE: 11

Asp Lys Pro Val Asn Val Glu Ser Tyr Leu Phe His Ser Gly Asn
1               5                   10                  15

<210> SEQ ID NO 12
<211> LENGTH: 10
<212> TYPE: PRT
<213> ORGANISM: Bovine

<400> SEQUENCE: 12

Asp Ile Leu Leu Asn Thr Thr Val Glu Val
1               5                   10

<210> SEQ ID NO 13
<211> LENGTH: 9
<212> TYPE: PRT
<213> ORGANISM: Bovine

<400> SEQUENCE: 13

Lys Ser Glu Gly Leu Asp Ile Ser Lys
1               5

<210> SEQ ID NO 14
<211> LENGTH: 8
<212> TYPE: PRT
<213> ORGANISM: Bovine

<400> SEQUENCE: 14

Asp Gly Tyr Phe Arg Ile Gly Lys
1               5

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: variation
<222> LOCATION: (24)
<223> OTHER INFORMATION: n is A or C or G or T/U

<400> SEQUENCE: 15
aaratycayg tbaaycchcc hgcngargt                                29

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 16
tgraavarrt arswytcvac rttvacdggy ttrtc                         35

<210> SEQ ID NO 17
<211> LENGTH: 2246

-continued

```
<212> TYPE: DNA
<213> ORGANISM: Bovine
<220> FEATURE:
<221> NAME/KEY: CDS
<222> LOCATION: (288)..(1892)

<400> SEQUENCE: 17
```

| | | | | | |
|---|---|---|---|---|---|
| ggcggctgct cggtggcggc tcgtcggcgg ccgcggcagg actggcagcg ccggcggcgg | | | | | 60 |
| ggagaaagaa gcatccacct atgaagaccg tgcagacagt cctgaataat aattgtgaat | | | | | 120 |
| ggtgtggctg ccagactagt tctgctgagc atctgaaatg aacctctcct attgattgtt | | | | | 180 |
| tcagttggcc ccgagccagg agtactgggt ttgcttgact tcaggataaa agaaacgga | | | | | 240 |
| cttggttatc atcgtaaaca tatgaaccag tgtgatggtg aaatgag atg agg ctc | | | | | 296 |
| | | | | Met Arg Leu | |
| | | | | 1 | |

| cga aat gga act gta gcc act gtt tta gca ttt atc acc tcg ttc ctc | 344 |
|---|---|
| Arg Asn Gly Thr Val Ala Thr Val Leu Ala Phe Ile Thr Ser Phe Leu | |
| 5                    10                   15 | |

| act tta tct tgg tat aca aca tgg caa aat ggg aaa gaa aaa gtg att | 392 |
|---|---|
| Thr Leu Ser Trp Tyr Thr Thr Trp Gln Asn Gly Lys Glu Lys Val Ile | |
| 20                   25                   30                   35 | |

| gct tat caa cga gaa ttt ctt gct ctg aaa gaa cgt ctc cga ata gct | 440 |
|---|---|
| Ala Tyr Gln Arg Glu Phe Leu Ala Leu Lys Glu Arg Leu Arg Ile Ala | |
| 40                   45                   50 | |

| gaa cat cga atc tct cag cgc tct tct gag ctc agt gcc att gta cag | 488 |
|---|---|
| Glu His Arg Ile Ser Gln Arg Ser Ser Glu Leu Ser Ala Ile Val Gln | |
| 55                   60                   65 | |

| caa ttc aag cgt gta gaa gca gaa aca aac agg agt aag gat cca gtg | 536 |
|---|---|
| Gln Phe Lys Arg Val Glu Ala Glu Thr Asn Arg Ser Lys Asp Pro Val | |
| 70                   75                   80 | |

| aat aaa ttt tca gat gat acc cta aag ata cta aag gag tta aca agc | 584 |
|---|---|
| Asn Lys Phe Ser Asp Asp Thr Leu Lys Ile Leu Lys Glu Leu Thr Ser | |
| 85                   90                   95 | |

| aaa aag tct ctt caa gtg cca agt att tat tat cat ttg cct cat tta | 632 |
|---|---|
| Lys Lys Ser Leu Gln Val Pro Ser Ile Tyr Tyr His Leu Pro His Leu | |
| 100                  105                  110                  115 | |

| ttg caa aat gaa gga agc ctt caa cct gcc gtg cag atc gga aat gga | 680 |
|---|---|
| Leu Gln Asn Glu Gly Ser Leu Gln Pro Ala Val Gln Ile Gly Asn Gly | |
| 120                  125                  130 | |

| cga aca gga gtt tca ata gta atg gga att cct aca gtg aag aga gaa | 728 |
|---|---|
| Arg Thr Gly Val Ser Ile Val Met Gly Ile Pro Thr Val Lys Arg Glu | |
| 135                  140                  145 | |

| gtt aaa tct tac ctc ata gaa act ctt cat tcc ctt att gat aat ctg | 776 |
|---|---|
| Val Lys Ser Tyr Leu Ile Glu Thr Leu His Ser Leu Ile Asp Asn Leu | |
| 150                  155                  160 | |

| tat cct gaa gag aag ttg gac tgt gtt ata gta gtc ttc ata gga gag | 824 |
|---|---|
| Tyr Pro Glu Glu Lys Leu Asp Cys Val Ile Val Val Phe Ile Gly Glu | |
| 165                  170                  175 | |

| aca gat act gat tat gta aat ggt gtt gta gcc aac ctg gag aaa gaa | 872 |
|---|---|
| Thr Asp Thr Asp Tyr Val Asn Gly Val Val Ala Asn Leu Glu Lys Glu | |
| 180                  185                  190                  195 | |

| ttt tct aaa gaa atc agt tct ggc ttg gtg gaa ata ata tca cct cct | 920 |
|---|---|
| Phe Ser Lys Glu Ile Ser Ser Gly Leu Val Glu Ile Ile Ser Pro Pro | |
| 200                  205                  210 | |

| gaa agc tat tat cct gac ctg acg aac tta aag gag aca ttt gga gat | 968 |
|---|---|
| Glu Ser Tyr Tyr Pro Asp Leu Thr Asn Leu Lys Glu Thr Phe Gly Asp | |
| 215                  220                  225 | |

| tct aaa gaa aga gta aga tgg aga aca aag caa aac cta gat tat tgt | 1016 |
|---|---|
| Ser Lys Glu Arg Val Arg Trp Arg Thr Lys Gln Asn Leu Asp Tyr Cys | |
| 230                  235                  240 | |

```
ttt cta atg atg tat gct cag gaa aaa ggc aca tac tac atc cag ctt      1064
Phe Leu Met Met Tyr Ala Gln Glu Lys Gly Thr Tyr Tyr Ile Gln Leu
    245                 250                 255 gaa gat gat att att gtc aaa cag aat tac ttt aac acc ata aag aat      1112
Glu Asp Asp Ile Ile Val Lys Gln Asn Tyr Phe Asn Thr Ile Lys Asn
260                 265                 270                 275 ttt gca ctt caa ctt tct tct gag gaa tgg atg ata ctt gag ttc tcc      1160
Phe Ala Leu Gln Leu Ser Ser Glu Glu Trp Met Ile Leu Glu Phe Ser
                280                 285                 290 cag ctg gga ttc att ggt aaa atg ttt caa gca cct gac cca ctc ctg      1208
Gln Leu Gly Phe Ile Gly Lys Met Phe Gln Ala Pro Asp Pro Leu Leu
            295                 300                 305 att gtg gaa ttc ata ttt atg ttc tat aag gag aag ccc atc gac tgg      1256
Ile Val Glu Phe Ile Phe Met Phe Tyr Lys Glu Lys Pro Ile Asp Trp
        310                 315                 320 ctc ttg gac cat att ctg tgg gtc aaa gtc tgc aac ccg gaa aaa gat      1304
Leu Leu Asp His Ile Leu Trp Val Lys Val Cys Asn Pro Glu Lys Asp
    325                 330                 335 gca aaa cac tgt gat cga cag aag gca aat ctg cga att cgt ttc aga      1352
Ala Lys His Cys Asp Arg Gln Lys Ala Asn Leu Arg Ile Arg Phe Arg
340                 345                 350                 355 ccg tcc ctt ttc caa cac gtt ggt ctg cat tct tca ctc aca gga aaa      1400
Pro Ser Leu Phe Gln His Val Gly Leu His Ser Ser Leu Thr Gly Lys
                360                 365                 370 att cag aaa ctc acg gat aaa gat tac atg aaa cca tta ctg ctc aaa      1448
Ile Gln Lys Leu Thr Asp Lys Asp Tyr Met Lys Pro Leu Leu Leu Lys
            375                 380                 385 atc cat gta aac ccc cct gca gag gta tct act tct ttg aag gtc tac      1496
Ile His Val Asn Pro Pro Ala Glu Val Ser Thr Ser Leu Lys Val Tyr
        390                 395                 400 caa ggt cat aca ctg gag aaa act tac atg ggt gag gac ttc ttc tgg      1544
Gln Gly His Thr Leu Glu Lys Thr Tyr Met Gly Glu Asp Phe Phe Trp
    405                 410                 415 gct ata acc cca gta gct gga gac tac atc cta ttt aaa ttc gac aag      1592
Ala Ile Thr Pro Val Ala Gly Asp Tyr Ile Leu Phe Lys Phe Asp Lys
420                 425                 430                 435 cca gtc aat gtg gaa agt tat ttg ttc cat agt ggc aac cag gat cat      1640
Pro Val Asn Val Glu Ser Tyr Leu Phe His Ser Gly Asn Gln Asp His
                440                 445                 450 cca ggg gat att ctg ctc aac aca acg gtg gaa gtt ctg cct ttg aag      1688
Pro Gly Asp Ile Leu Leu Asn Thr Thr Val Glu Val Leu Pro Leu Lys
            455                 460                 465 agt gaa ggt ttg gac atc agc aaa gaa acc aaa gac aaa cga tta gaa      1736
Ser Glu Gly Leu Asp Ile Ser Lys Glu Thr Lys Asp Lys Arg Leu Glu
        470                 475                 480 gat ggc tat ttc aga ata ggg aaa ttt gaa aac ggt gtt gcg gaa ggg      1784
Asp Gly Tyr Phe Arg Ile Gly Lys Phe Glu Asn Gly Val Ala Glu Gly
    485                 490                 495 atg gtg gat ccc agc cta aac ccc att tcg gcc ttc cga ctt tca gtt      1832
Met Val Asp Pro Ser Leu Asn Pro Ile Ser Ala Phe Arg Leu Ser Val
500                 505                 510                 515 att cag aat tct gct gtt tgg gcc att ctt aat gag atc cat att aaa      1880
Ile Gln Asn Ser Ala Val Trp Ala Ile Leu Asn Glu Ile His Ile Lys
                520                 525                 530 aaa gtc aca aac tgaccatctc tactaagaaa ccaacacatt ttttccctgt          1932
Lys Val Thr Asn
            535 gaatttgttg attaaagaca gctgagcacg taccttttt tggtaacttg aattctacct      1992
```

-continued

```
ctcgcgaaat ctactgtaga taaaatgatt gtcatatttc cacttggaaa atgaatctcc      2052
cacggataat tgtattcatt tgaatctaag ctgtcctcca gttttaactc aactcaaacg      2112
ttttacagtt atgacagcct gttaatatga cttgtactat tttggtatta tactaataca      2172
taagagttgt acatattgtt acattcatta aatttgagaa aaattaatgt taaatacatt      2232
ttatgaacgg gccg                                                        2246
```

<210> SEQ ID NO 18
<211> LENGTH: 535
<212> TYPE: PRT
<213> ORGANISM: Bovine

<400> SEQUENCE: 18

```
Met Arg Leu Arg Asn Gly Thr Val Ala Thr Val Leu Ala Phe Ile Thr
 1               5                  10                  15

Ser Phe Leu Thr Leu Ser Trp Tyr Thr Thr Trp Gln Asn Gly Lys Glu
            20                  25                  30

Lys Val Ile Ala Tyr Gln Arg Glu Phe Leu Ala Leu Lys Glu Arg Leu
        35                  40                  45

Arg Ile Ala Glu His Arg Ile Ser Gln Arg Ser Ser Glu Leu Ser Ala
    50                  55                  60

Ile Val Gln Gln Phe Lys Arg Val Glu Ala Glu Thr Asn Arg Ser Lys
65                  70                  75                  80

Asp Pro Val Asn Lys Phe Ser Asp Thr Leu Lys Ile Leu Lys Glu
                85                  90                  95

Leu Thr Ser Lys Lys Ser Leu Gln Val Pro Ser Ile Tyr Tyr His Leu
            100                 105                 110

Pro His Leu Leu Gln Asn Glu Gly Ser Leu Gln Pro Ala Val Gln Ile
        115                 120                 125

Gly Asn Gly Arg Thr Gly Val Ser Ile Val Met Gly Ile Pro Thr Val
    130                 135                 140

Lys Arg Glu Val Lys Ser Tyr Leu Ile Glu Thr Leu His Ser Leu Ile
145                 150                 155                 160

Asp Asn Leu Tyr Pro Glu Glu Lys Leu Asp Cys Val Ile Val Val Phe
                165                 170                 175

Ile Gly Glu Thr Asp Thr Asp Tyr Val Asn Gly Val Val Ala Asn Leu
            180                 185                 190

Glu Lys Glu Phe Ser Lys Glu Ile Ser Ser Gly Leu Val Glu Ile Ile
        195                 200                 205

Ser Pro Pro Glu Ser Tyr Tyr Pro Asp Leu Thr Asn Leu Lys Glu Thr
    210                 215                 220

Phe Gly Asp Ser Lys Glu Arg Val Arg Trp Arg Thr Lys Gln Asn Leu
225                 230                 235                 240

Asp Tyr Cys Phe Leu Met Met Tyr Ala Gln Glu Lys Gly Thr Tyr Tyr
                245                 250                 255

Ile Gln Leu Glu Asp Asp Ile Ile Val Lys Gln Asn Tyr Phe Asn Thr
            260                 265                 270

Ile Lys Asn Phe Ala Leu Gln Leu Ser Ser Glu Glu Trp Met Ile Leu
        275                 280                 285

Glu Phe Ser Gln Leu Gly Phe Ile Gly Lys Met Phe Gln Ala Pro Asp
    290                 295                 300

Pro Leu Leu Ile Val Glu Phe Ile Phe Met Phe Tyr Lys Glu Lys Pro
305                 310                 315                 320

Ile Asp Trp Leu Leu Asp His Ile Leu Trp Val Lys Val Cys Asn Pro
```

```
                          325                 330                 335
Glu Lys Asp Ala Lys His Cys Asp Arg Gln Lys Ala Asn Leu Arg Ile
                340                 345                 350

Arg Phe Arg Pro Ser Leu Phe Gln His Val Gly Leu His Ser Ser Leu
            355                 360                 365

Thr Gly Lys Ile Gln Lys Leu Thr Asp Lys Asp Tyr Met Lys Pro Leu
        370                 375                 380

Leu Leu Lys Ile His Val Asn Pro Pro Ala Glu Val Ser Thr Ser Leu
385                 390                 395                 400

Lys Val Tyr Gln Gly His Thr Leu Glu Lys Thr Tyr Met Gly Glu Asp
                405                 410                 415

Phe Phe Trp Ala Ile Thr Pro Val Ala Gly Asp Tyr Ile Leu Phe Lys
                420                 425                 430

Phe Asp Lys Pro Val Asn Val Glu Ser Tyr Leu Phe His Ser Gly Asn
                435                 440                 445

Gln Asp His Pro Gly Asp Ile Leu Leu Asn Thr Thr Val Glu Val Leu
        450                 455                 460

Pro Leu Lys Ser Glu Gly Leu Asp Ile Ser Lys Glu Thr Lys Asp Lys
465                 470                 475                 480

Arg Leu Glu Asp Gly Tyr Phe Arg Ile Gly Lys Phe Glu Asn Gly Val
                485                 490                 495

Ala Glu Gly Met Val Asp Pro Ser Leu Asn Pro Ile Ser Ala Phe Arg
                500                 505                 510

Leu Ser Val Ile Gln Asn Ser Ala Val Trp Ala Ile Leu Asn Glu Ile
            515                 520                 525

His Ile Lys Lys Val Thr Asn
        530                 535

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 19
ccctcgagat gaggctccga aatggaactg t                              31

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 20
tttctagatc agtttgtgac ttttttaata t                              31

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 21
acgattgtgc aacagttcaa gcgt                                      24

<210> SEQ ID NO 22
```

```
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 22
gggagaactc caggatcatc cagt                                          24

<210> SEQ ID NO 23
<211> LENGTH: 2115
<212> TYPE: DNA
<213> ORGANISM: Homo sapiens
<220> FEATURE:
<221> NAME/KEY: CDS
<222> LOCATION: (136)..(1740)

<400> SEQUENCE: 23
gaaatgaacc tctcttattg attttattg gcctagagcc aggagtactg cattcagttg    60
actttcaggg taaaagaaa acagtcctgg ttgttgtcat cataaacata tggaccagtg   120
tgatggtgaa atgag atg agg ctc cgc aat gga act gta gcc act gct tta   171
                Met Arg Leu Arg Asn Gly Thr Val Ala Thr Ala Leu
                  1               5                  10 gca ttt atc act tcc ttc ctt act ttg tct tgg tat act aca tgg caa   219
Ala Phe Ile Thr Ser Phe Leu Thr Leu Ser Trp Tyr Thr Thr Trp Gln
         15                  20                  25 aat ggg aaa gaa aaa ctg att gct tat caa cga gaa ttc ctt gct ttg   267
Asn Gly Lys Glu Lys Leu Ile Ala Tyr Gln Arg Glu Phe Leu Ala Leu
 30                  35                  40 aaa gaa cgt ctt cga ata gct gaa cac aga atc tca cag cgc tct tct   315
Lys Glu Arg Leu Arg Ile Ala Glu His Arg Ile Ser Gln Arg Ser Ser
 45                  50                  55                  60 gaa tta aat acg att gtg caa cag ttc aag cgt gta gga gca gaa aca   363
Glu Leu Asn Thr Ile Val Gln Gln Phe Lys Arg Val Gly Ala Glu Thr
                 65                  70                  75 aat gga agt aag gat gcg ttg aat aag ttt tca gat aat acc cta aag   411
Asn Gly Ser Lys Asp Ala Leu Asn Lys Phe Ser Asp Asn Thr Leu Lys
         80                  85                  90 ctg tta aag gag tta aca agc aaa aaa tct ctt caa gtg cca agt att   459
Leu Leu Lys Glu Leu Thr Ser Lys Lys Ser Leu Gln Val Pro Ser Ile
 95                 100                 105 tat tat cat ttg cct cat tta ttg aaa aat gaa gga agt ctt caa cct   507
Tyr Tyr His Leu Pro His Leu Leu Lys Asn Glu Gly Ser Leu Gln Pro
        110                 115                 120 gct gta cag att ggc aac gga aga aca gga gtt tca ata gtc atg ggc   555
Ala Val Gln Ile Gly Asn Gly Arg Thr Gly Val Ser Ile Val Met Gly
125                 130                 135                 140 att ccc aca gtg aag aga gaa gtt aaa tct tac ctc ata gaa act ctt   603
Ile Pro Thr Val Lys Arg Glu Val Lys Ser Tyr Leu Ile Glu Thr Leu
                145                 150                 155 cat tcc ctt att gat aac ctg tat cct gaa gag aag ttg gac tgt gtt   651
His Ser Leu Ile Asp Asn Leu Tyr Pro Glu Glu Lys Leu Asp Cys Val
        160                 165                 170 ata gta gtc ttc ata gga gag aca gat att gat tat gta cat ggt gtt   699
Ile Val Val Phe Ile Gly Glu Thr Asp Ile Asp Tyr Val His Gly Val
        175                 180                 185 gta gcc aac ctg gag aaa gaa ttt tct aaa gaa atc agt tct ggc ttg   747
Val Ala Asn Leu Glu Lys Glu Phe Ser Lys Glu Ile Ser Ser Gly Leu
190                 195                 200 gtg gaa gtc ata tca ccc cct gaa agc tat tat cct gac ttg aca aac   795
Val Glu Val Ile Ser Pro Pro Glu Ser Tyr Tyr Pro Asp Leu Thr Asn
```

```
                -continued 205                 210                 215                 220 cta aag gag aca ttt gga gac tcc aaa gaa aga gta aga tgg aga aca      843
Leu Lys Glu Thr Phe Gly Asp Ser Lys Glu Arg Val Arg Trp Arg Thr
                    225                 230                 235 aag caa aac cta gat tac tgt ttt cta atg atg tat gct caa gaa aag      891
Lys Gln Asn Leu Asp Tyr Cys Phe Leu Met Met Tyr Ala Gln Glu Lys
                240                 245                 250 ggc ata tat tac att cag ctt gaa gat gat att att gtc aaa caa aat      939
Gly Ile Tyr Tyr Ile Gln Leu Glu Asp Asp Ile Ile Val Lys Gln Asn
                255                 260                 265 tat ttt aat acc ata aaa aat ttt gca ctt caa ctt tct tct gag gaa      987
Tyr Phe Asn Thr Ile Lys Asn Phe Ala Leu Gln Leu Ser Ser Glu Glu
                270                 275                 280 tgg atg att cta gag ttt tcc cag ctg ggc ttc att ggt aaa atg ttt     1035
Trp Met Ile Leu Glu Phe Ser Gln Leu Gly Phe Ile Gly Lys Met Phe
285                 290                 295                 300 caa gcg ccg gat ctt act ctg att gta gaa ttc ata ttc atg ttt tac     1083
Gln Ala Pro Asp Leu Thr Leu Ile Val Glu Phe Ile Phe Met Phe Tyr
                305                 310                 315 aag gag aaa ccc att gat tgg ctc ctg gac cat att ctc tgg gtg aaa     1131
Lys Glu Lys Pro Ile Asp Trp Leu Leu Asp His Ile Leu Trp Val Lys
                320                 325                 330 gtc tgc aac cct gaa aaa gat gca aaa cat tgt gat aga cag aaa gca     1179
Val Cys Asn Pro Glu Lys Asp Ala Lys His Cys Asp Arg Gln Lys Ala
                335                 340                 345 aat ctg cga att cgc ttc aga cct tcc ctt ttc caa cat gtt ggt ctg     1227
Asn Leu Arg Ile Arg Phe Arg Pro Ser Leu Phe Gln His Val Gly Leu
350                 355                 360 cac tca tca cta tca gga aaa atc caa aaa ctc acg gat aaa gat tat     1275
His Ser Ser Leu Ser Gly Lys Ile Gln Lys Leu Thr Asp Lys Asp Tyr
365                 370                 375                 380 atg aaa cca tta ctt ctt aaa atc cat gta aac cca cct gcg gag gta     1323
Met Lys Pro Leu Leu Leu Lys Ile His Val Asn Pro Pro Ala Glu Val
                385                 390                 395 tct act tcc ttg aag gtc tac caa ggg cat acg ctg gag aaa act tac     1371
Ser Thr Ser Leu Lys Val Tyr Gln Gly His Thr Leu Glu Lys Thr Tyr
                400                 405                 410 atg gga gag gat ttc ttc tgg gct atc aca ccg ata gct gga gac tac     1419
Met Gly Glu Asp Phe Phe Trp Ala Ile Thr Pro Ile Ala Gly Asp Tyr
                415                 420                 425 atc ttg ttt aaa ttt gat aaa cca gtc aat gta gaa agt tat ttg ttc     1467
Ile Leu Phe Lys Phe Asp Lys Pro Val Asn Val Glu Ser Tyr Leu Phe
                430                 435                 440 cat agc ggc aac caa gaa cat cct gga gat att ctg cta aac aca act     1515
His Ser Gly Asn Gln Glu His Pro Gly Asp Ile Leu Leu Asn Thr Thr
445                 450                 455                 460 gtg gaa gtt ttg cct ttt aag agt gaa ggt ttg gaa ata agc aaa gaa     1563
Val Glu Val Leu Pro Phe Lys Ser Glu Gly Leu Glu Ile Ser Lys Glu
                465                 470                 475 acc aaa gac aaa cga tta gaa gat ggc tat ttc aga ata gga aaa ttt     1611
Thr Lys Asp Lys Arg Leu Glu Asp Gly Tyr Phe Arg Ile Gly Lys Phe
                480                 485                 490 gag aat ggt gtt gca gaa gga atg gtg gat cca agt ctc aat ccc att     1659
Glu Asn Gly Val Ala Glu Gly Met Val Asp Pro Ser Leu Asn Pro Ile
                495                 500                 505 tca gcc ttt cga ctt tca gtt att cag aat tct gct gtt tgg gcc att     1707
Ser Ala Phe Arg Leu Ser Val Ile Gln Asn Ser Ala Val Trp Ala Ile
                510                 515                 520 ctt aat gag att cat att aaa aaa gcc acc aac tgatcatctg agaaaccaac   1760
Leu Asn Glu Ile His Ile Lys Lys Ala Thr Asn
```

```
Leu Asn Glu Ile His Ile Lys Lys Ala Thr Asn
525                 530                 535 acatttttc ctgtgaattt gttaattaaa gatagttaag catgtatctt tttttttattt    1820 ctacttgaac actacctctt gtgaagtcta ctgtagataa gacgattgtc atttccactt    1880
ggaaagtgaa tctcccataa taattgtatt tgtttgaaac taagctgtcc tcagatttta    1940
acttgactca aacattttc aattatgaca gcctgttaat atgacttgta ctattttggt     2000
attatactaa tacataagag ttgtacatat tgttacattc tttaaatttg agaaaaacta    2060
atgttacata cattttatga aggggtact  tttgaggttc acttattta ctatt           2115

<210> SEQ ID NO 24
<211> LENGTH: 535
<212> TYPE: PRT
<213> ORGANISM: Homo sapiens

<400> SEQUENCE: 24

Met Arg Leu Arg Asn Gly Thr Val Ala Thr Ala Leu Ala Phe Ile Thr
1               5                   10                  15

Ser Phe Leu Thr Leu Ser Trp Tyr Thr Thr Trp Gln Asn Gly Lys Glu
                20                  25                  30

Lys Leu Ile Ala Tyr Gln Arg Glu Phe Leu Ala Leu Lys Glu Arg Leu
            35                  40                  45

Arg Ile Ala Glu His Arg Ile Ser Gln Arg Ser Ser Glu Leu Asn Thr
        50                  55                  60

Ile Val Gln Gln Phe Lys Arg Val Gly Ala Glu Thr Asn Gly Ser Lys
65                  70                  75                  80

Asp Ala Leu Asn Lys Phe Ser Asp Asn Thr Leu Lys Leu Leu Lys Glu
                85                  90                  95

Leu Thr Ser Lys Lys Ser Leu Gln Val Pro Ser Ile Tyr Tyr His Leu
                100                 105                 110

Pro His Leu Leu Lys Asn Glu Gly Ser Leu Gln Pro Ala Val Gln Ile
            115                 120                 125

Gly Asn Gly Arg Thr Gly Val Ser Ile Val Met Gly Ile Pro Thr Val
        130                 135                 140

Lys Arg Glu Val Lys Ser Tyr Leu Ile Glu Thr Leu His Ser Leu Ile
145                 150                 155                 160

Asp Asn Leu Tyr Pro Glu Glu Lys Leu Asp Cys Val Ile Val Val Phe
                165                 170                 175

Ile Gly Glu Thr Asp Ile Asp Tyr Val His Gly Val Val Ala Asn Leu
                180                 185                 190

Glu Lys Glu Phe Ser Lys Glu Ile Ser Ser Gly Leu Val Glu Val Ile
            195                 200                 205

Ser Pro Pro Glu Ser Tyr Tyr Pro Asp Leu Thr Asn Leu Lys Glu Thr
        210                 215                 220

Phe Gly Asp Ser Lys Glu Arg Val Arg Trp Arg Thr Lys Gln Asn Leu
225                 230                 235                 240

Asp Tyr Cys Phe Leu Met Met Tyr Ala Gln Glu Lys Gly Ile Tyr Tyr
                245                 250                 255

Ile Gln Leu Glu Asp Asp Ile Ile Val Lys Gln Asn Tyr Phe Asn Thr
            260                 265                 270

Ile Lys Asn Phe Ala Leu Gln Leu Ser Ser Glu Glu Trp Met Ile Leu
        275                 280                 285

Glu Phe Ser Gln Leu Gly Phe Ile Gly Lys Met Phe Gln Ala Pro Asp
290                 295                 300
```

-continued

```
Leu Thr Leu Ile Val Glu Phe Ile Phe Met Phe Tyr Lys Glu Lys Pro
305                 310                 315                 320

Ile Asp Trp Leu Leu Asp His Ile Leu Trp Val Lys Val Cys Asn Pro
            325                 330                 335

Glu Lys Asp Ala Lys His Cys Asp Arg Gln Lys Ala Asn Leu Arg Ile
        340                 345                 350

Arg Phe Arg Pro Ser Leu Phe Gln His Val Gly Leu His Ser Ser Leu
    355                 360                 365

Ser Gly Lys Ile Gln Lys Leu Thr Asp Lys Asp Tyr Met Lys Pro Leu
370                 375                 380

Leu Leu Lys Ile His Val Asn Pro Pro Ala Glu Val Ser Thr Ser Leu
385                 390                 395                 400

Lys Val Tyr Gln Gly His Thr Leu Glu Lys Thr Tyr Met Gly Glu Asp
                405                 410                 415

Phe Phe Trp Ala Ile Thr Pro Ile Ala Gly Asp Tyr Ile Leu Phe Lys
            420                 425                 430

Phe Asp Lys Pro Val Asn Val Glu Ser Tyr Leu Phe His Ser Gly Asn
        435                 440                 445

Gln Glu His Pro Gly Asp Ile Leu Leu Asn Thr Thr Val Glu Val Leu
450                 455                 460

Pro Phe Lys Ser Glu Gly Leu Glu Ile Ser Lys Glu Thr Lys Asp Lys
465                 470                 475                 480

Arg Leu Glu Asp Gly Tyr Phe Arg Ile Gly Lys Phe Glu Asn Gly Val
                485                 490                 495

Ala Glu Gly Met Val Asp Pro Ser Leu Asn Pro Ile Ser Ala Phe Arg
            500                 505                 510

Leu Ser Val Ile Gln Asn Ser Ala Val Trp Ala Ile Leu Asn Glu Ile
        515                 520                 525

His Ile Lys Lys Ala Thr Asn
    530                 535

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 25
ttctcgagat gaggctccgc aatggaactg                                    30

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 26
agaaatgtgg gcttcagggc tggc                                          24

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 27
```
ttctcgagat gaggctccgc aatggaactg                    30

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 28
agaaatgtgg gcttcagggc tggc                          24

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 29
ttctcgagat gaggctccgc aatggaactg                    30

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 30
agaaatgtgg gcttcagggc tggc                          24

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 31
ttccatcacc tgccacacct gctgg                         25

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 32
acaaccctca gtcagacaag gagg                          24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 33 acaccccag aaatgtgggc ttca                           24

<210> SEQ ID NO 34
<211> LENGTH: 24
<212> TYPE: DNA

```
<213> ORGANISM: Artificial Sequence
<220> FEATURE:
<223> OTHER INFORMATION: Description of Artificial Sequence: Primer

<400> SEQUENCE: 34
atgaccgagt cctccttctc ctgc                                          24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 35
atgcccatca ccaccgacac tccg                                          24

<210> SEQ ID NO 36
<211> LENGTH: 1724
<212> TYPE: DNA
<213> ORGANISM: Homo sapiens
<220> FEATURE:
<221> NAME/KEY: CDS
<222> LOCATION: (43)..(1686)

<400> SEQUENCE: 36
tgcagcctcg gccccgcggg cgcccgccgc gcacccgagg ag atg agg ctc cgc      54
                                             Met Arg Leu Arg
                                               1 aat ggc acc ttc ctg acg ctg ctc ttc tgc ctg tgc gcc ttc ctc        102
Asn Gly Thr Phe Leu Thr Leu Leu Phe Cys Leu Cys Ala Phe Leu
  5                  10                  15                  20 tcg ctg tcc tgg tac gcg gca ctc agc ggc cag aaa ggc gac gtt gtg   150
Ser Leu Ser Trp Tyr Ala Ala Leu Ser Gly Gln Lys Gly Asp Val Val
                 25                  30                  35 gac gtt tac cag cgg gag ttc ctg gcg ctg cgc gat cgg ttg cac gca   198
Asp Val Tyr Gln Arg Glu Phe Leu Ala Leu Arg Asp Arg Leu His Ala
             40                  45                  50 gct gag cag gag agc ctc aag cgc tcc aag gag ctc aac ctg gtg ctg   246
Ala Glu Gln Glu Ser Leu Lys Arg Ser Lys Glu Leu Asn Leu Val Leu
         55                  60                  65 gac gag atc aag agg gcc gtg tca gaa agg cag gcg ctg cga gac gga   294
Asp Glu Ile Lys Arg Ala Val Ser Glu Arg Gln Ala Leu Arg Asp Gly
     70                  75                  80 gac ggc aat cgc acc tgg ggc cgc cta aca gag gac ccc cga ttg aag   342
Asp Gly Asn Arg Thr Trp Gly Arg Leu Thr Glu Asp Pro Arg Leu Lys
 85                  90                  95                 100 ccg tgg aac ggc tca cac cgg cac gtg ctg cac ctg ccc acc gtc ttc   390
Pro Trp Asn Gly Ser His Arg His Val Leu His Leu Pro Thr Val Phe
                105                 110                 115 cat cac ctg cca cac ctg ctg gcc aag gag agc agt ctg cag ccc gcg   438
His His Leu Pro His Leu Leu Ala Lys Glu Ser Ser Leu Gln Pro Ala
            120                 125                 130 gtg cgc gtg ggc cag ggc cgc acc gga gtg tcg gtg gtg atg ggc atc   486
Val Arg Val Gly Gln Gly Arg Thr Gly Val Ser Val Val Met Gly Ile
        135                 140                 145 ccg agc gtg cgg cgc gag gtg cac tcg tac ctg act gac act ctg cac   534
Pro Ser Val Arg Arg Glu Val His Ser Tyr Leu Thr Asp Thr Leu His
    150                 155                 160 tcg ctc atc tcc gag ctg agc ccg cag gag aag gag gac tcg gtc atc   582
Ser Leu Ile Ser Glu Leu Ser Pro Gln Glu Lys Glu Asp Ser Val Ile
165                 170                 175                 180
```

-continued

| | | |
|---|---|---|
| gtg gtg ctg atc gcc gag act gac tca cag tac act tcg gca gtg aca<br>Val Val Leu Ile Ala Glu Thr Asp Ser Gln Tyr Thr Ser Ala Val Thr<br>185 190 195 | 630 |
| gag aac atc aag gcc ttg ttc ccc acg gag atc cat tct ggg ctc ctg<br>Glu Asn Ile Lys Ala Leu Phe Pro Thr Glu Ile His Ser Gly Leu Leu<br>200 205 210 | 678 |
| gag gtc atc tca ccc tcc ccc cac ttc tac cct gac ttc tcc cgc ctc<br>Glu Val Ile Ser Pro Ser Pro His Phe Tyr Pro Asp Phe Ser Arg Leu<br>215 220 225 | 726 |
| cga gag tcc ttt ggg gac ccc aag gag aga gtc agg tgg agg acc aaa<br>Arg Glu Ser Phe Gly Asp Pro Lys Glu Arg Val Arg Trp Arg Thr Lys<br>230 235 240 | 774 |
| cag aac ctc gat tac tgc ttc ctc atg atg tac gcg cag tcc aaa ggc<br>Gln Asn Leu Asp Tyr Cys Phe Leu Met Met Tyr Ala Gln Ser Lys Gly<br>245 250 255 260 | 822 |
| atc tac tac gtg cag ctg gag gat gac atc gtg gcc aag ccc aac tac<br>Ile Tyr Tyr Val Gln Leu Glu Asp Asp Ile Val Ala Lys Pro Asn Tyr<br>265 270 275 | 870 |
| ctg agc acc atg aag aac ttt gca ctg cag cag cct tca gag gac tgg<br>Leu Ser Thr Met Lys Asn Phe Ala Leu Gln Gln Pro Ser Glu Asp Trp<br>280 285 290 | 918 |
| atg atc ctg gag ttc tcc cag ctg ggc ttc att ggt aag atg ttc aag<br>Met Ile Leu Glu Phe Ser Gln Leu Gly Phe Ile Gly Lys Met Phe Lys<br>295 300 305 | 966 |
| tcg ctg gac ctg agc ctg att gta gag ttc att ctc atg ttc tac cgg<br>Ser Leu Asp Leu Ser Leu Ile Val Glu Phe Ile Leu Met Phe Tyr Arg<br>310 315 320 | 1014 |
| gac aag ccc atc gac tgg ctc ctg gac cat att ctg tgg gtg aaa gtc<br>Asp Lys Pro Ile Asp Trp Leu Leu Asp His Ile Leu Trp Val Lys Val<br>325 330 335 340 | 1062 |
| tgc aac ccc gag aag gat gcg aag cac tgt gac cgg cag aaa gcc aac<br>Cys Asn Pro Glu Lys Asp Ala Lys His Cys Asp Arg Gln Lys Ala Asn<br>345 350 355 | 1110 |
| ctg cgg atc cgc ttc aaa ccg tcc ctc ttc cag cac gtg ggc act cac<br>Leu Arg Ile Arg Phe Lys Pro Ser Leu Phe Gln His Val Gly Thr His<br>360 365 370 | 1158 |
| tcc tcg ctg gct ggc aag atc cag aaa ctg aag gac aaa gac ttt gga<br>Ser Ser Leu Ala Gly Lys Ile Gln Lys Leu Lys Asp Lys Asp Phe Gly<br>375 380 385 | 1206 |
| aag cag gcg ctg cgg aag gag cat gtg aac ccg cca gca gag gtg agc<br>Lys Gln Ala Leu Arg Lys Glu His Val Asn Pro Pro Ala Glu Val Ser<br>390 395 400 | 1254 |
| acg agc ctg aag aca tac cag cac ttc acc ctg gag aaa gcc tac ctg<br>Thr Ser Leu Lys Thr Tyr Gln His Phe Thr Leu Glu Lys Ala Tyr Leu<br>405 410 415 420 | 1302 |
| cgc gag gac ttc ttc tgg gcc ttc acc cct gcc gcg ggg gac ttc atc<br>Arg Glu Asp Phe Phe Trp Ala Phe Thr Pro Ala Ala Gly Asp Phe Ile<br>425 430 435 | 1350 |
| cgc ttc cgc ttc ttc caa cct cta aga ctg gag cgg ttc ttc ttc cgc<br>Arg Phe Arg Phe Phe Gln Pro Leu Arg Leu Glu Arg Phe Phe Phe Arg<br>440 445 450 | 1398 |
| agt ggg aac atc gag cac ccg gag gac aag ctc ttc aac acg tct gtg<br>Ser Gly Asn Ile Glu His Pro Glu Asp Lys Leu Phe Asn Thr Ser Val<br>455 460 465 | 1446 |
| gag gtg ctg ccc ttc gac aac cct cag tca gac aag gag gcc ctg cag<br>Glu Val Leu Pro Phe Asp Asn Pro Gln Ser Asp Lys Glu Ala Leu Gln<br>470 475 480 | 1494 |
| gag ggc cgc acc gcc acc ctc cgg tac cct cgg agc ccc gac ggc tac<br>Glu Gly Arg Thr Ala Thr Leu Arg Tyr Pro Arg Ser Pro Asp Gly Tyr<br>485 490 495 500 | 1542 |

```
ctc cag atc ggc tcc ttc tac aag gga gtg gca gag gga gag gtg gac     1590
Leu Gln Ile Gly Ser Phe Tyr Lys Gly Val Ala Glu Gly Glu Val Asp
             505                 510                 515 cca gcc ttc ggc cct ctg gaa gca ctg cgc ctc tcg atc cag acg gac     1638
Pro Ala Phe Gly Pro Leu Glu Ala Leu Arg Leu Ser Ile Gln Thr Asp
        520                 525                 530 tcc cct gtg tgg gtg att ctg agc gag atc ttc ctg aaa aag gcc gac     1686
Ser Pro Val Trp Val Ile Leu Ser Glu Ile Phe Leu Lys Lys Ala Asp
    535                 540                 545 taagctgcgg gcttctgagg gtaccctgtg gccagccc                            1724
```

<210> SEQ ID NO 37
<211> LENGTH: 548
<212> TYPE: PRT
<213> ORGANISM: Homo sapiens

<400> SEQUENCE: 37

```
Met Arg Leu Arg Asn Gly Thr Phe Leu Thr Leu Leu Phe Cys Leu
 1               5                  10                  15

Cys Ala Phe Leu Ser Leu Ser Trp Tyr Ala Ala Leu Ser Gly Gln Lys
             20                  25                  30

Gly Asp Val Val Asp Val Tyr Gln Arg Glu Phe Leu Ala Leu Arg Asp
         35                  40                  45

Arg Leu His Ala Ala Glu Gln Glu Ser Leu Lys Arg Ser Lys Glu Leu
     50                  55                  60

Asn Leu Val Leu Asp Glu Ile Lys Arg Ala Val Ser Glu Arg Gln Ala
 65                  70                  75                  80

Leu Arg Asp Gly Asp Gly Asn Arg Thr Trp Gly Arg Leu Thr Glu Asp
                 85                  90                  95

Pro Arg Leu Lys Pro Trp Asn Gly Ser His Arg His Val Leu His Leu
            100                 105                 110

Pro Thr Val Phe His His Leu Pro His Leu Leu Ala Lys Glu Ser Ser
        115                 120                 125

Leu Gln Pro Ala Val Arg Val Gly Gln Gly Arg Thr Gly Val Ser Val
    130                 135                 140

Val Met Gly Ile Pro Ser Val Arg Arg Glu Val His Ser Tyr Leu Thr
145                 150                 155                 160

Asp Thr Leu His Ser Leu Ile Ser Glu Leu Ser Pro Gln Glu Lys Glu
                165                 170                 175

Asp Ser Val Ile Val Val Leu Ile Ala Glu Thr Asp Ser Gln Tyr Thr
            180                 185                 190

Ser Ala Val Thr Glu Asn Ile Lys Ala Leu Phe Pro Thr Glu Ile His
        195                 200                 205

Ser Gly Leu Leu Glu Val Ile Ser Pro Ser Pro His Phe Tyr Pro Asp
    210                 215                 220

Phe Ser Arg Leu Arg Glu Ser Phe Gly Asp Pro Lys Glu Arg Val Arg
225                 230                 235                 240

Trp Arg Thr Lys Gln Asn Leu Asp Tyr Cys Phe Leu Met Met Tyr Ala
                245                 250                 255

Gln Ser Lys Gly Ile Tyr Tyr Val Gln Leu Glu Asp Asp Ile Val Ala
            260                 265                 270

Lys Pro Asn Tyr Leu Ser Thr Met Lys Asn Phe Ala Leu Gln Gln Pro
        275                 280                 285

Ser Glu Asp Trp Met Ile Leu Glu Phe Ser Gln Leu Gly Phe Ile Gly
    290                 295                 300
```

```
Lys Met Phe Lys Ser Leu Asp Leu Ser Leu Ile Val Glu Phe Ile Leu
305                 310                 315                 320

Met Phe Tyr Arg Asp Lys Pro Ile Asp Trp Leu Leu Asp His Ile Leu
            325                 330                 335

Trp Val Lys Val Cys Asn Pro Glu Lys Asp Ala Lys His Cys Asp Arg
            340                 345                 350

Gln Lys Ala Asn Leu Arg Ile Arg Phe Lys Pro Ser Leu Phe Gln His
            355                 360                 365

Val Gly Thr His Ser Ser Leu Ala Gly Lys Ile Gln Lys Leu Lys Asp
            370                 375                 380

Lys Asp Phe Gly Lys Gln Ala Leu Arg Lys Glu His Val Asn Pro Pro
385                 390                 395                 400

Ala Glu Val Ser Thr Ser Leu Lys Thr Tyr Gln His Phe Thr Leu Glu
            405                 410                 415

Lys Ala Tyr Leu Arg Glu Asp Phe Phe Trp Ala Phe Thr Pro Ala Ala
            420                 425                 430

Gly Asp Phe Ile Arg Phe Arg Phe Gln Pro Leu Arg Leu Glu Arg
            435                 440                 445

Phe Phe Phe Arg Ser Gly Asn Ile Glu His Pro Glu Asp Lys Leu Phe
450                 455                 460

Asn Thr Ser Val Glu Val Leu Pro Phe Asp Asn Pro Gln Ser Asp Lys
465                 470                 475                 480

Glu Ala Leu Gln Glu Gly Arg Thr Ala Thr Leu Arg Tyr Pro Arg Ser
            485                 490                 495

Pro Asp Gly Tyr Leu Gln Ile Gly Ser Phe Tyr Lys Gly Val Ala Glu
            500                 505                 510

Gly Glu Val Asp Pro Ala Phe Gly Pro Leu Glu Ala Leu Arg Leu Ser
            515                 520                 525

Ile Gln Thr Asp Ser Pro Val Trp Val Ile Leu Ser Glu Ile Phe Leu
            530                 535                 540

Lys Lys Ala Asp
545

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 38
ttctcgagga gatgaggctc cgcaatggc                              29

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 39
aatctagaaa tgtgggcttc agggctggc                              29

<210> SEQ ID NO 40
<211> LENGTH: 28
<212> TYPE: DNA
<213> ORGANISM: Artificial Sequence
<220> FEATURE:
```

```
<223> OTHER INFORMATION: Description of Artificial Sequence: Primer

<400> SEQUENCE: 40
ccctcgagat gggggtgcac gaatgtcc                                              28

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 41 cttttttgctt gttaactcct ttagtattgg ggcgcccagg actgggag                       48

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 42
ctcccagtcc tgggcgcccc aatactaaag gagttaacaa gcaaaaag                        48

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 43
cttccttcat tttgcaataa atgaggggcg cccaggactg ggag                            44

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 44
atttaacttc tctcttcact gtagggggcgc ccaggactgg gag                            43

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 45
ctcccagtcc tgggcgcccc tcatttattg caaaatgaag gaag                            44

<210> SEQ ID NO 46
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 46
ctcccagtcc tgggcgcccc tacagtgaag agagaagtta aat                             43
```

```
<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 47
ttctagaatc acccttccgc aacacc                                          26

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 48
ttctagaatc aaggcagaac ttccaccg                                        28

<210> SEQ ID NO 49
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 49
ttctagaatc atttaaatag gatgtagtct ccagctac                             38

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 50
ttctagaatc atggtttcat gtaatcttta tccg                                 34

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 51
ttcatgaggc tccgaaatg                                                  19

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 52
caagcttcag tttgtgactt ttttaatat                                       29

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Primer
```

```
<400> SEQUENCE: 53
tcatgatact aaaggagtta acaagca                                        27

<210> SEQ ID NO 54
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 54
caagcttcag tggtggtggt ggtggtggtt tgtgactttt taatatgga t              51

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 55
caagcttcag tggtggtg                                                  18

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 56
tcatgatatt aaaggagtta acaagcaaaa aa                                  32

<210> SEQ ID NO 57
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 57
caagcttcag tggtggtggt ggtggtggtt ggtggctttt taatatgaa t              51

<210> SEQ ID NO 58
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 58
caagcttcag tggtggtggt ggtggtgtgg tttcatataa tctttatcc                49

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 59
ttcatgaggc tccgcaatg                                                 19

<210> SEQ ID NO 60
<211> LENGTH: 18
```

```
<212> TYPE: DNA
<213> ORGANISM: Artificial Sequence
<220> FEATURE:
<223> OTHER INFORMATION: Description of Artificial Sequence: Primer

<400> SEQUENCE: 60
caggttgagc tccttgga                                                      18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 61
tccaaggagc tcaacctg                                                      18

<210> SEQ ID NO 62
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 62
caagcttcag tggtggtggt ggtggtggtc ggcctttttc agga                          44

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 63
cccatgggcc gcctaacaga gga                                                23
```

β1-4 N-ACETYLGLUCOSAMINYLTRANSFERASE AND GENE ENCODING

TECHNICAL FIELD

The present invention relates to a novel N-acetylglucosaminyl-transferase (GlCNAc transferase) which recognizes a specific sugar chain structure in a saccharide and introduces thereinto a GlcNAc β1→4 branching structure.

BACKGROUND ART

1. Glycoproteins

Most of proteins occurring in nature are not simple proteins composed of amino acids alone, but "mature" proteins having sugar chains and other substances such as phosphates and lipids attached thereto. Therefore, the development of simple protein-type products produced by *Escherichia coli* as a host has involved various problems because such products lack the maturing process of proteins. Since all of secretion-type physiologically active proteins (e.g. cytokines) are glycoproteins with a few exceptions, the function and the role of sugar chains have attracted attention as the most important point in the development of biological pharmaceuticals.

Sugar chains in glycoproteins are classified roughly into Asn-linked type, mucin-type, O-linked GlcNAc type, GPI anchor type and proteoglycan type [Makoto Takeuchi, "Glycobiology Series 5: Glycotechnology", Kihata, Hakomori and Nagai (eds.), Kodansha Scientific Co., (1994), 191–208]. Each of these types of sugar chains has its own biosynthesis pathway and a discrete physiological function. Asn-linked sugar chains are distributed widely in molds, yeasts, insects, plants and animals. The basic biosynthesis pathway for Asn-linked sugar chains is conserved beyond species (FIG. 1). A sugar chain(s) characteristic of a specific species is(are) formed on the outer side (called the "non-reducing terminal side") of the core sugar chain moiety which is common in the biosynthesis of Asn-linked sugar chains. A mannan-type sugar chain in whicha α 1,3- and α 1,2-branching mannose residues attach to a main chain extending via α 1,6 linkages is a sugar chain structure characteristic of fungi such as yeasts (see Panel a in FIG. 2) [Hiroshi Nakajima, Sugar Chain Technology, Industry Survey Association (1992), 384–397]. On the other hand, in insects, plants and animals., extension of mannose residues is not observed; instead, a high mannose type sugar chain is formed which is a sugar chain transferred from a dolichol intermediate and only trimmed (see Panel c in FIG. 2). A unique structure having characteristic xylose or the like (see Panel b in FIG. 2) is also observed in insects, plants and mollusks. In animals, characteristic sugar chain structures such as complex type sugar chain (Panel e in FIG. 2) and hybrid type sugar chain (Panel d in FIG. 2) are observed; in the former, GlcNAc branching structures are formed in a once trimmed sugar chain, and addition of other kinds of monosaccharides such as galactose and sialic acid forms complicated structures; in the latter, both a complex type sugar chain and a high mannose type sugar chain are present [Kiyoshi Furukawa, Sugar Chain Technology, Industry Survey Association (1992), 64–75].

Such sugar chains as described above are conferred on most of cell surface proteins and secretion proteins, and are thought to play important roles which determine the natures and properties of cells and proteins. Among all, the portion of a sugar chain structure which forms a branch elongating like antennas from the common core sugar chain is called a sugar chain branching structure. This structure is believed to have a function to give an organism recognition ligand (i.e., the end portion of the sugar chain) a high degree of freedom to thereby provide chances for multipoint recognition and another function to maximize the protection ability for the protein moiety by greatly increasing the space-occupying volume (Takeuchi et al., supra). Therefore, by controlling the branching structure of sugar chains, it is possible to modify the physiological functions, sush as itn vivo stability, in vivo kinetics and organ-targeting properties of glycoproteins in various ways. In view of this, technology to control branching structures of sugar chains is expected as biotechnology of the next generation for the development of glycoprotein-type pharmaceuticals which are "tender to humans".

2. Physiological Significance of Glycoprotein Sugar Chains

Sugar chains of secretion type glycoproteins exhibit excellent functions in biosynthesis, intracellular sorting, masking of antigenicity, in vivo stability and organ-targeting properties of glycoproteins. Sugar chains of cell surface proteins are known to change in response to changes in cells (such as differentiation, change to a morbid state, canceration). In particular, it has been reported that there is a close relation between the metastasis of cancer and the branching structure of sugar chains.

(1) Masking of Antigenicity

It is considered that sugar chains have a high degree of freedom in terms of steric structure and thus are moving freely like propellers. Therefore, protein molecules such as proteases and antibodies against proteins not having affinity to sugar chains are shook off by the sugar chains and thus cannot gain access to the protein moiety. As a result, even if there is antigenicity in the peptide moiety near the sugar chain binding site, antibody molecules cannot have access to the peptide moiety. Thus, an antigen-antibody reaction is extremely difficult to occur. Further, when a glycoprotein has been captured by a macrophage and the degradation products are presented as antigen, receptors are difficult of access to the peptides around the sugar chain binding site. Thus, antigenic stimulation is difficult to occur. Actually, it is reported that when sugar chains have been introduced into the central portion of the antigenic peptide of ovalbumin lysozyme, the binding of MHC class II molecules to the antigen is remarkably inhibited [Mouritsen, S., Meldal, M., Christiansen-Brams, I., Elsner, H. and Werdelin, O., Eur. J. Immunol., (1994), 24, 1066–1072]. The effect of such masking of antigenicity becomes greater as the volume occupied by sugar chains is greater. Thus, it is considered that the development of a branching structure contributes to the effect of such masking greatly.

(2) In Vivo Stability

With respect to erythropoietin which is the first glycoprotein-type pharmaceutical ever produced from a transgenic animal cell as a host, the functions of sugar chains thereof have been studied thoroughly. As a result, it has been shown that the sugar chains of erythropoietin work inhibitorily against the binding of erythropoietin with its receptor but make a decisive contribution to the retaining of the active structure and the improvement of in vivo kinetics; as a whole, the sugar chains have been shown to be essential for expression of the pharmacological activity of erythropoietin (Takeuchi, M. and Kobata, A., Glycobiology (1991), 1, 337–346). In particular, a strong correlation between the number of antennae in sugar chains and the pharmacological effect of erythropoietin has been found, and thus the importance of its branching structure (a branching structure formed by GlcNAc residues attaching to the core sugar chain) which never attracted attention has been made clear for the first time [Takeuchi, M., Inoue, N., Strickland, T. W., Kobata, M., Wada, M., Shimizu, R., Hoshi, S., Kozutsumi, H., Takasaki, S. and Kobata, A., Proc. Natl. Acad. Sci. USA, (1989), 86, 7819–22]. The major cause of the above phenomenon is explained as follows: erythropoietin without developed branching structure is cleared rather rapidly in kidney and, as a result, the in vivo residence time of such erythropoietin becomes shorter [Misaizu, T., Matsuki, S., Strickland, T. W., Takeuchi, M., Kobata, A. and Takasaki, S., Blood, (1995), 86, 4097–4104].

(3) Organ Targeting Property

Most of biological tissues have lectin-like receptors and use then in cell-cell interactions or to uptake glycoproteins from blood. The asialoprotein-binding lectin in liver is a representative example of a clearance system for aged glycoproteins [Toshihiro Kawasaki, Sugar Chain Technology, Industry Survey Association (1992), 125–136]. In addition, selectin contained in vascular endothelial cells, platelets and leucocytes (Kawasaki, supra) and the lectin receptor present on the surface of macrophages and NK cells (Kawasaki, supra) are well known. Furthermore, not only glycoproteins but also cells are known to gather in a specific tissue using sugar chains as ligands. Cases of the homing of bone marrow cells [Tatsuo Irimura, "Glycobiology Series 3: Glycobiology in Cell Society", Katsutaka Nagai, Senichiro Hakomori and Akira Kobata (eds.), Kodansha Scientific Co., (1993), 127–175] and the recruiting of neutrophiles to inflammatory sites (Irimura, supra) are examined in detail. Putting all these things together, it can be well assumed that glycoproteins and cells have, via their sugar chain structures, a targeting property toward specific organs or tissues presenting a lectin receptor in blood circulation, although such a targeting system is not found in all organ. This means that drug delivery by means of sugar chains is possible. In such drug delivery, the affinity of lectin for sugar chains is greatly influenced by the degree of freedom and the number of sugar chain ligands. Therefore, the branching structure of sugar chains will be the most important point in such drug delivery.

(4) Correlation between Cells' Change into Morbid State and Sugar Chain Branched Structure thereof [Junko Kato, Naoko Suzuki," Sugar Chain Technology and Development of Pharmaceutical", Foundation for the Relief and Study of Injury Caused by Pharmaceutical Side Effect (ed.), Yakugyo-Jiho-Sha, (1994), 107–13214]

Once a plant lectin called L-PHA was developed as a probe to detect a multi-branching type sugar chain structure, it has become possible to examine various morbid tissue samples. As a result, a tendency has been found that some types of cancer cells, particularly, cancer cells with a high metastasis ability are stained well with L-PHA. Thus, researchers have become aware of the correlation between the branching structure of sugar chains and the metastasis ability of cancer cells. Human chorionic gonadotropin (hCG) is a glycoprotein hormone vigorously biosynthesized in villus tissues at an early stage of pregnancy. Since a considerable amount of hCG is discharged into urine, hCG is clinically utilized as an indicator of pregnancy. The Asn-linked sugar chains mainly formed by the mono- and biantennary complex type chains are characteristic to hCG. As cancer increases its malignancy from trophoblastoma to invasive mole and from invasive mole to choriocarcinoma, it is reported that 2,4,2 type tri-antennary sugar chains and abnormal biantennary sugar chains (both are formed through the action of GnT-IV on normal biantennary and mono-antennary sugar chains, respectively) appear in the sugar chains of hCG [Katsuko Yamashita, Protein, Nucleic Acid and Enzyme (1992), 37, 1880–1888]. As a cause of this phenomenon, it is suggested that the activity of GnT-IV increases as the malignancy of choriocarcinoma progresses.

γ-Glutamyltranspeptidase (γ-GTP) is a glycoprotein occurring specifically abundant in liver. Since the serum γ-GTP level drastically increases when there is a liver disease, this level is used as clinical indicator of a liver disease. Further, Yamashita et al. [Yamashita, K., Totani, K., Iwaki, Y., Takamisawa, I., Takeishi, N., Higashi, T., Sakamoto, Y. and Kobata, A., J. Biochem., (1989), 105, 728–735] have found that, as a result of canceration of cells, the sugar chain structure of γ-GTP changes abnormally in its branching structure similar to those in abnormal hCG; thus, they have reported the correlation between canceration and the activation of GnT-IV. The Asn-linked sugar chains of γ-GTP derived from healthy human liver cells are composed mainly of the biantennary complex type sugar chain with small amounts of tri-antennary and tetra-antennary sugar chains mixed therein. In contrast, a remarkable increase in the degree of branching was observed in the Asn-linked sugar chains of γ-GTP derived from human hepatoma cells. At the same time, though small in amounts, high mannose type sugar chains and abnormal biantennary sugar chains (both of which were not observed in γ-GTP from normal cells) appeared. As a cause of these changes in sugar chain structure, a possibility is suggested that N-acetylglucosaminyltransferase IV (GnT-IV) and V (GnT-V) are activated in relation to canceration of liver cells (Yamashita et al., supra).

It is also reported that the sugar chain branching structure of a glycoprotein in cells is greatly changed by viral infection (Yamashita et al., supra). BHK cells have sugar chain structures with branching up to tetraantennary type. When BHK cells are transformed with polyomavirus, biantennary type sugar chains decrease in the glycoprotein sugar chains produced by the cells, while tetraantennary type sugar chains and the N-acetyllactosamine repeat structures increase; as a whole, a remarkable increase in the number of branches was recognized [Takasaki S., Ikehira, H. and Kobata A., Biochem. Biophys. Res. Commun., (1980), 90, (3), 735–742]. As a cause of the above change, activation of GnT-IV, GnT-V and i-GnT may be considered.

3. Enzymes relating to the Sugar Chain Branching Structures of Glycoproteins

The complex type sugar chain which is a glycoprotein sugar chain structure characteristic of animals has a complicated branching structure in which N-acetylglucosamine (GlcNAc) residues are attaching to the common core structure in various manners (Kiyoshi Furukawa, supra) (FIG. 1). Since this branching structure is closely related to in vivio and in vivo stability, localization, biological activity and pharmacological property of glycoproteins (Makoto Takeuchi, supra), the process of biosynthesis of the branching structure has been investigated in detail. By using inventive substrates H. Schachter et al. have discriminated the various enzyme activities in hen oviduct to thereby predict the presence of GlcNAc branch forming enzymes from GnT-I to GnT-VI (group of GlcNAc glycosyltransferases; FIG. 3) [Glesson, P. A. and Schachter, H., J. Biol. Chem., (1983), 258, 6162–6173]. Thereafter, GnT-I [Kumar, R., Yang, J., Larsen, R. D. and Stanley P., Proc. Natl. Acad. Sci. USA, (1990), 87, 9948–9952; Sarkar, M., Hull, E., Nishikawa, Y., Simpson, R. J., Moritz, R. L., Dunn, R. and Schachter, H., Proc. Natl. Acad. Sci., USA, (1991), 88, 234–238], GnT-II [D'Agostaro, G A., Zingoni, A., Moritz, R L., Simpson, R J., Schachter, H. and Bendiak, B., J. Biol.

Chem., (1995), 270, 15211–21], GnT-III [Nishikawa, A., Ihara, Y., Hatakeyama, M., Kangawa, K. and Taniguchi, N., J. Biol. Chem., (1992), 267, 18199–18204] and GnT-V [Shorebah, M. G., Hindsgaul, O . and Pierce, M., J. Biol. Chem., (1992), 267, 2920–2927; Gu, J., Nishikawa, A., Turuoka, N., Ono, M., Yamaguchi, N., Kangawa, K. and Taniguchi, N., J. Biochem., (1993), 113, 614–619] were successively purified, and the genes thereof were cloned. However, with these known GlcNAc transferases alone, it is impossible to form the main sugar chain (tetraantennary type; see the formula below) found in α 1 acid glycoprotein known as a representative human blood glycoprotein [Yoshima, K., Tsuji, T., Irimura, T. and Osawa, T, J. Biol. Chem., (1984), 256, 10834–10840] and erythropoietin [Takeuchi, M., Takasaki, S., Shimada, M. and Kobata, A., J. Biol. Chem., (1990), 265, 12127–12130]. Therefore, an N-acetylglucosaminyltransferase having such substrate specificity and reaction specificity that are expected in GnT-IV has been searched for as a missing link.

1

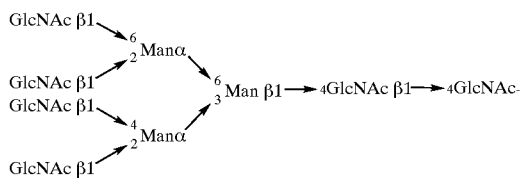

Tetraantennary type sugar chain structure

In addition to those mentioned above, the following N-acetyl-glucosaminyltransferases have been purified or the genes thereof have been cloned: a transferase acting on mucin-type sugar chains [Bierhuizen, M. F., Maemura, K. and Fukuda, M., J. Biol. Chem., (1994), 269, 4473–4479], a transferase acting on glycolipids, and a transferase forming the sugar chain epitope known as I·i antigenic structure [Kawashima, H., Yamamoto, K., Osawa, T. and Irimura, T., J. Biol. Chem., (1993), 268, 27118–27126; Bierhuizen, M. F., Mattei, M. G. and Fukuda, M., Genes Dev., (1993), 7, 468–478]. However, the substrate specificity of these transferases and the mode of binding of the GlcNAc group transferred by these transferases are different from those of GnT-IV. Any of these transferases does not yield products resembling GnT-IV products.

DISCLOSURE OF THE INVENTION

It is an object of the present invention to provide an enzyme having β1→4 N-acetylglucosaminyltransferase (hereinafter referred to as "GnT-IV") activity; a gene encoding the enzyme; a recombinant DNA comprising the gene; a cell containing the recombinant DNA; a method for producing an enzyme protein having GnT-IV activity comprising culturing the cell in a medium; and a saccharide in which the sugar chains are modified with GnT-IV.

Toward the solution of the above assignments, the present inventors have made intensive and extensive researches. As a result, the inventors have isolated and purified a GnT-IV enzyme protein from bovine small intestine, and characterized the biochemical properties of the protein. Then, the inventors have succeeded in cloning a gene coding for bovine GnT-IVa from a cDNA library and mRNA from the small intestine based on a partial amino acid sequence of the above enzyme protein. Further, based on bovine GnT-IVa gene, the inventors have succeeded in cloning two genes coding for human GnT-IVa and human GnT-IVb, from cDNA libraries and mRNAs from human liver and human lung, respectively. The present invention has been completed by confirming that the products of these genes exhibit GnT-IV activity.

The first invention of the present application relates to a GnT-IV having an activity to produce a saccharide having a partial structure represented by the formula below:

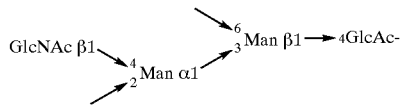

using UDP-GlcNAc as a sugar donor and a saccharide having a partial structure represented by the formula below as a sugar receptor:

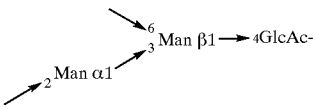

The second invention relates to a GnT-IV consisting of the amino acid sequence shown in SEQ ID NO: 18 or the amino acid sequence shown in SEQ ID NO: 18 which has addition, deletion or substitution of one or more amino acid residues and yet which produces GnT-IV activity; a GnT-IV consisting of the amino acid sequence shown in SEQ ID NO: 24 or the amino acid sequence shown in SEQ ID NO: 24 which has addition, deletion or substitution of one or more amino acid residues and yet which produces GnT-IV activity; and a GnT-IV consisting of the amino acid sequence shown in SEQ ID NO: 37 or the amino acid sequence shown in SEQ ID NO: 37 which has addition, deletion or substitution of one or more amino acid residues and yet which produces GnT-IV activity.

The third invention relates to a GnT-IV gene coding for a GnT-IV consisting of the amino acid sequence shown in SEQ ID NO: 18 or the amino acid sequence shown in SEQ ID NO: 18 which has addition, deletion or substitution of one or more amino acid residues and yet which produces GnT-IV activity; a GnT-IV gene coding for a GnT-IV consisting of the amino acid sequence shown in SEQ ID NO: 24 or the amino acid sequence shown in SEQ ID NO: 24 which has addition, deletion or substitution of one or more amino acid residues and yet which produces GnT-IV activity; a GnT-IV gene coding for a GnT-IV consisting of the amino acid sequence shown in SEQ ID NO: 37 or the amino acid sequence shown in SEQ ID NO: 37 which has addition, deletion or substitution of one or more amino acid residues and yet which produces GnT-IV activity; a GnT-IV gene consisting of the nucleotide sequence shown in SEQ ID NO: 17; a GnT-IV gene consisting of the nucleotide sequence shown in SEQ ID NO: 23; and a GnT-IV gene consisting of the nucleotide sequence shown in SEQ ID NO: 36.

The fourth invention relates to a recombinant DNA obtainable by inserting any of the above GnT-IV gene into a vector DNA; and a chromosomal fragment comprising a part or all of any one of the above GnT-IV gene.

The fifth invention relates to a host cell carrying the above recombinant DNA; and a host cell into which the above chromosomal fragment is artificially introduced.

The sixth invention relates to a method for producing a GnT-IV comprising culturing the above host cell in a medium and recovering the GnT-IV from the resultant culture; and a method for producing a GnT-IV comprising recovering the GnT-IV enzyme from the secreta, body fluids or homogenete originated from the above host cell.

The seventh invention relates to a method for purifying the GnT-IV from biological samples.

The eighth invention relates to a saccharide of which the sugar chain structure is modified with the GnT-IV.

Hereinbelow, the present invention will be described in detail.

The GnT-IV gene of the invention can be isolated as described below.

Isolation of Bovine GnT-IVa Gene

First, a microsome fraction from bovine small intestine solubilized with a detergent is subjected to a series of purification procedures using anion exchange chromatography, copper chelate chromatography, two-step affinity chromatography using a substrate analogue and gel filtration to thereby obtain a purified sample of GnT-IV enzyme. The resultant purified sample is subjected to SDS-PAGE and then transferred onto a PVDF membrane. The transferred protein, as it is or after restricted hydrolysis, is analyzed with a gas phase amino acid sequencer to obtain a partial amino acid sequence for the GnT-IV enzyme.

Subsequently, an RT-PCR is performed on the RNA extracted from the animal cells (i.e., bovine small intestine) as a template using primers designed based on the partial amino acid sequences determined above. Further, using a fragment obtained by the RT-PCR as a probe, the GnT-IV gene of interest is screened from a cDNA library from the above-mentioned tissue by plaque hybridization. A cDNA fragment contained in the resultant positive plaque is cut out and subcloned into a vector such as pUC19, followed by analysis of the nucleotide sequence thereof. If the full length of the gene coding for the protein of interest is not contained in the fragment, plaque hybridization is performed again using a part of the subcloned cDNA fragment as a probe. Alternatively, terminal portions of the cDNA of interest are obtained by RACE or the like based on the information on the nucleotide sequence obtained above. The thus obtained GnT-IV gene (which is named GnT-IVa aferward) is subjected to analysis of its entire nucleotide sequence. Subsequently, the amino acid sequence is translated from the gene having the above-mentioned nucleotide sequence. This amino acid sequence is as shown in SEQ ID NO: 18.

Isolation of Human GnT-IVa and GnT-IVb Genes

Human GnT-IVa and GnT-IVb genes can be obtained by performing a RT-PCR using RNA extracted from a human tissue (liver or lung) and based on the information on the nucleotide sequence of bovine GnT-IVa gene as obtained above, followed by screening of a cDNA library from the above tissue. The resultant human GnT-IVa and GnT-IVb genes are subjected to analysis of their entire nucleotide sequences. Subsequently, the amino acid sequences are translated by these genes. These amino acid sequences are as shown in SEQ ID NOS: 24 and 37.

In order to obtain a DNA coding for the amino acid sequence shown in SEQ ID NO: 18, 24 or 37 having addition, deletion or substitution of one or more amino acid residues, a number of methods may be used. For example, a method of treating DNA with a mutagen to induce point mutation or a deletion mutation; a method comprising cleaving DNA selectively, removing or adding a selected nucleotide and then ligating DNA; site-specific mutagenesis; and the like may be enumerated.

The GnT-IV protein of the invention can be produced by preparing a recombinant vector into which a DNA coding for the GnT-IV of the invention obtained by the method described above is inserted downstream of a promoter, introducing the vector into a host cell and culturing the resultant cell. The vector DNA used for this purpose may be either plasmid DNA or bacteriophage DNA. For example, pSVL vector (Pharmacia, Sweden) shown in an Example described later may be used. As the host cell into which the resultant recombinant DNA is introduced, any cell that is conventionally used in recombinant DNA techniques may be used, for example, a prokaryotic cell, an animal cell, a yeart, a fungi, an insect cell. Specific examples include *Escherichia coli* as a prokaryotic cell and CHO cells from chinese hamster or COS cells from monkey as an animal cell.

The transformation of the host cell described above is performed by conventional methods for each host. For example, if the host is *E. coli*, a vector comprising the recombinant DNA is introduced by the heat shock method or electroporation into competent cells prepared by the calcium method or the like. If the host is yeast, a vector comprising the recombinant DNA is introduced by the heat shock method or electroporation into competent cells prepared by the lithium method or the like. If the host is an animal cell, a vector comprising the recombinant DNA is introduced into the cell at the growth phase or the like by the calcium phosphate method, lipofection or electroporation.

By culturing the thus obtained transformant in a medium, the GnT-IV protein is produced.

In the cultivation of a transformant, any medium may be used as long as the host is viable in it. For example, LB medium or the like may be used if the host is *E. coli*. If the host is yeast, YPD medium or the like may be used. If the host is an animal cell, Dulbecco's medium supplemented with an animal serum or the like may be used. The cultivation is performed under conditions conventionally used for the host. For example, if the host is *E. coli*, cells are cultured at about 30–37 ° C. for about 3–24 hours with, if necessary, aeration and/or agitation. If the host is yeast, cells are cultured at about 25–37 ° C. for about 12 hours to 2 weeks with, if necessary, aeration and/or agitation. If the host is an animal cell, cultivation is performed at about 32–37 ° C. under 5% $CO_2$ and 100% humidity for about 24 hours to 2 weeks with, if necessary, change of the aeration conditions and/or agitation.

After the cultivation, the cultured microorganism or cells are disrupted using a homogenizer, French press, sonication, lysozyme and/or freeze-thawing to thereby elute the GnT-IV protein outside the microorganism or cells. Then, the protein can be obtained from soluble fractions. If the protein of interest is contained in insoluble fractions, the insoluble fractions are collected by centrifugation after disruption of the microorganism or cells. Then, the protein may be solubilized with a buffer containing guanidine hydrochloride or the like for recovery. Alternatively, the cultured microorganism or cells may be disrupted directly with a buffer containing a protein denaturing agent such as guanidine hydrochloride to thereby elute the protein of interest outside the microorganism or cells.

Purification of the GnT-IV protein from the above supernatant may be performed by the method described in Example 1. Alternatively, this purification may be performed by appropriately combining conventional separation/purification methods. These conventional separation/ purification methods include, but are not limited to, centrifugation, salting out, solvent precipitation, dialysis, ultrafiltration, partition chromatography, gel filtration, capillary electrophoresis, TLC, ion exchange chromatography, metal chelate chromatography, affinity chromatography, reversed phase chromatography and isoelectric focusing.

The biochemical properties of the GnT-IV enzyme protein obtained from bovine small intestine as described above are as follows.

(1) Action

This enzyme protein produces a saccharide having a partial structure represented by the formula below:

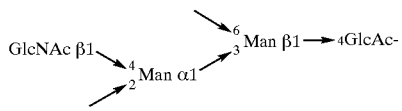

using UDP-GlcNAc as a sugar donor and a saccharide having a partial structure represented by the formula below as a sugar receptor:

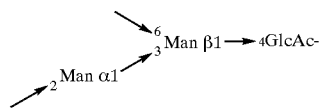

The saccharide as a sugar receptor means an oligosaccharide, polysaccharide, glycoconjugate (glycopeptide, glycoprotein, glycolipid or proteoglycan) or a derivative thereof.

(2) Substrate Specificity

When the sugar receptor is an oligosaccharide (for the structures of oligosaccharides, see FIG. 4), the enzyme protein exhibits reactivities of 0% toward core type oligosaccharides, 54% toward GnT-I product type oligosaccharides and 164% toward GnT-V product type oligosaccharides, wherein the reactivity of the enzyme protein toward GnT-II product type oligosaccharides is regarded as 100%.

The enzyme protein exhibits a reactivity of 46% toward a structure of GnT-II product type oligosaccharides in which fucose is attached via α1→6 linkage to the GlcNAc at the reducing terminus.

The enzyme protein exhibits a reactivity of 0% toward a structure of GnT-II product type oligosaccharides in which the GlcNAc on the α1→3 mannose is lacking.

The enzyme protein exhibits a reactivity of 16% toward a structure of GnT-II product type oligosaccharides in which galactose is attached viag β1→4 linkage to the GlcNAc on the α 1→6 mannose, and a reactivity of 0% toward a structure of GnT-II product type oligosaccharides in which galactose is attached via β1 4 linkage to the GlcNAc on the α1→3 mannose.

The enzyme protein exhibits a reactivity of 0% toward a structure of GnT-II product type oligosaccharides in which GlcNAc is attached via β 1→4 linkage to the β1→4 mannose.

(3) Molecular Weight

About 66 K as determined by SDS-PAGE (under non-reducing conditions). About 60 K after treatment with peptide N-glycosidase F. Since a shift of band is observed when peptide N-glycanase is used, the enzyme protein is thought to be a glycoprotein.

The apparent molecular weight as determined by filtration with a gel containing Triton X-100 is 77 K. Thus, it is thought that GnT-IV does not have a subunit structure and functions as a monomer.

The protein moiety of this enzyme deduced from the nucleotide sequence thereof consists of 535 amino acid residues and has a molecular weight of 61614.

(4) Optimum pH

The optimum pH for reaction is about 5.5. More than 50% of the maximum activity is observed in the range from pH 6.5 to 8.0.

(5) Inhibition, Activation and Stabilization (i) Inhibition

The activity of this enzyme is inhibited by addition of 20 mM EDTA.

This enzyme is inhibited by UDP derivatives. The intensity of inhibition is in the following order: UDP>>UDP-Glc>UDP-GalNAc>>2'-deoxy UDP>UDP-hexanolamine>>UDP-Gal>UTP>UDP-glucuronic acid>UMP.

Uridine, TDP and CDP do not have inhibitory effect.

(ii) Activation

A divalent cation is essential for expression of the activity. Among divalent cations, $Mn^{2+}$ shows the greatest effect. At a concentration of 7.5 mM, the respective effects of $Co^{2+}$ and $Mg^{2+}$ are about 70% of that of $Mn^{2+}$, and the effect of $Ca^{2+}$ is about 10% of that of $Mn^{2+}$. The effect of $Mn^{2+}$ is greatest in the range from 5 to 20 mM.

(iii) Stabilization

Stabilizing effect is recognized in BSA and glycerol.

(6) Kinetic Parameters

When the saccharide as a receptor is an oligosaccharide (for the structures of oligosaccharide, see FIG. 4):

(i) under assay conditions in which the enzyme is reacted in 50 μl of 125 mM MOPS buffer (pH 7.3) containing 0.8 mM receptor substrate, 20 mM UDP-GlcNAc, 7.5 mM $MnCl_2$, 200 mM GlcNAc, 0.5% (w/v) Triton X-100, 10% glycerol and 1% BSA at 37° C. for 4 hours:

Km and Vmax values toward GnT-II product type oligosaccharide are 0.73 mM and 3.23 μM/min, respectively.

Km and Vmax values toward GnT-V product type oligosaccharide are 0.13 mM and 1.75μM/min, respectively.

When GnT-II product type oligosaccharide is the receptor substrate, Km value toward UDP-GlcNAc is 0.22 mM.

(ii) under assay conditions in which the enzyme is reacted in 125 mM MOPS buffer (pH 7.3) containing 120 mM UDP-GlcNAc, 7.5 nM $MnCl_2$, 0.5% (w/v) Triton X-100, 10% glycerol and 1% BSA at 37° C. for 4 hours:

Km and Vmax values toward GnT-II product type oligosaccharide are 0.59 mM and 0.74 mM/min/mg, respectively.

Km and Vmax values toward GnT-V product type oligosaccharide are 0.14 mM and 0.47 mM/min/mg, respectively.

(7) GnT-IV Family

The homology between bovine GnT-IVa and human GnT-IVa is 91% at the nucleic acid level and 96% at the amino acid level.

All of the partial amino acid structures contained in the purified GnT-IV from bovine small intestine are encoded in the bovine GnT-IVa gene.

Human GnT-IVb and human GnT-IVa have 63% homology at the nucleic acid level and 62% homology at the amino acid level. However, they are entirely different in the C-terminal and N-terminal regions.

From the biochemical properties described above, the GnT-IV of the invention has been recognized as a novel enzyme in the point that this enzyme is able to perform the following reaction which conventional enzymes cannot perform:

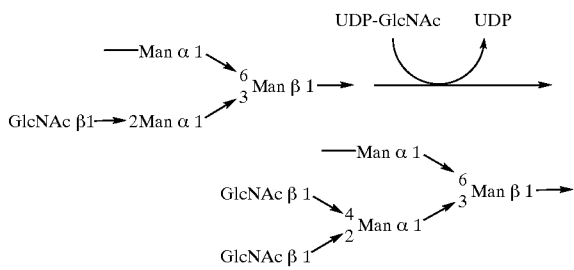

BRIEF DESCRIPTION OF THE DRAWINGS

FIG. 2 shows variations of the Asn-linked sugar chain (revised from FIG. 1 in Makoto Takeuchi, Wako Purechemical Newsletter 64, 18–19, 1996).
  a. Mannan type: a sugar chain structure characteristic of fungi such as yeasts and molds.
  b. Xylo-high-mannose type: a structure characteristic of plants, mollusks and insects.
  c. High mannose type: a structure commonly seen in plants, insects and animals.
  d. Hybrid type: a structure commonly seen in insects and animals.
  e. Complex type: a structure characteristic of animals.
  f. Prokaryotic cells: have no system for biosynthesis of Asn-linked sugar chains.

The portion boxed with dotted lines represents the common core sugar chain.

Figure 1:
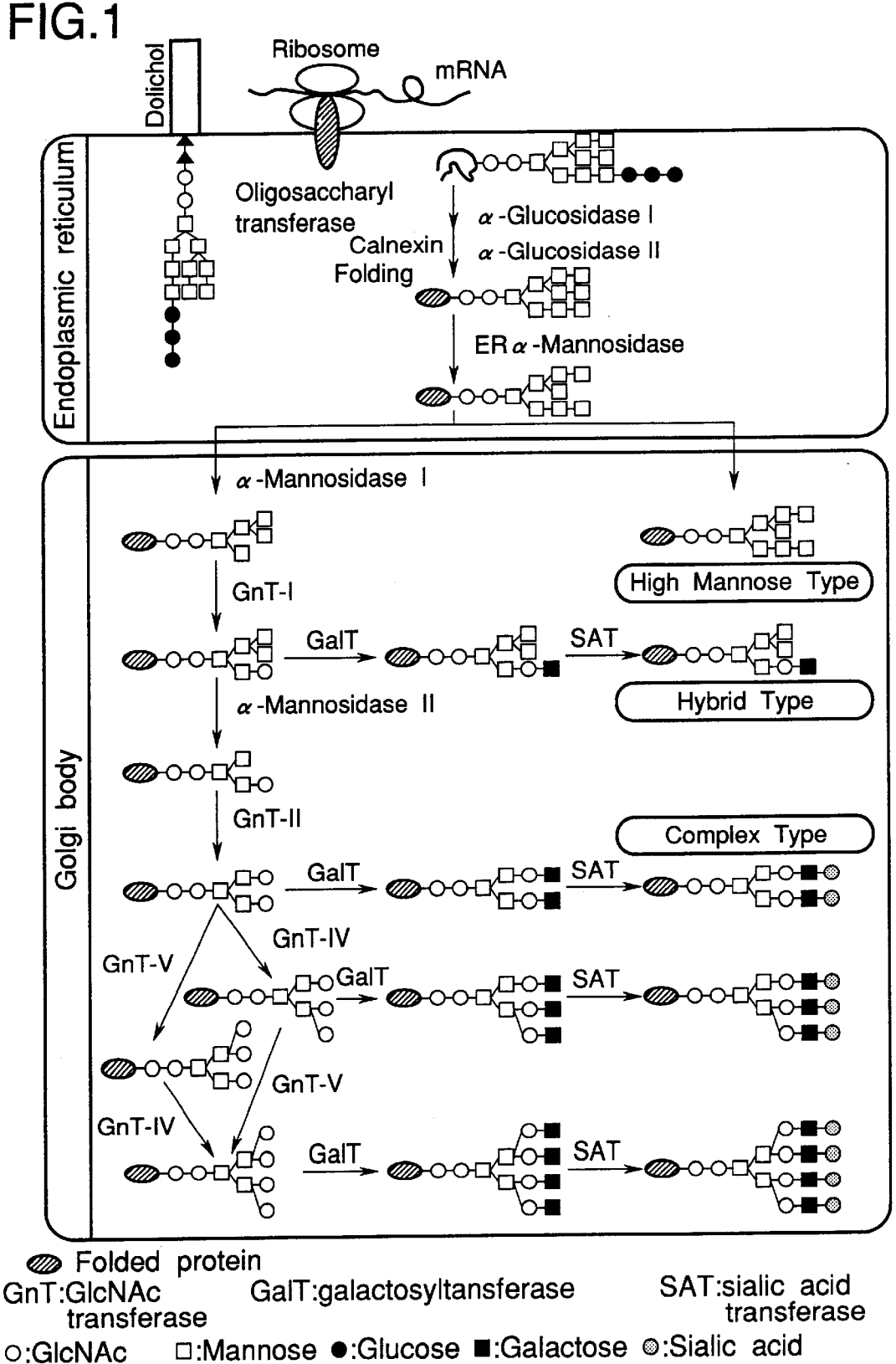
FIG. 1 shows the biosynthetic pathway of Asn-linked sugar chains.
Figure 3:
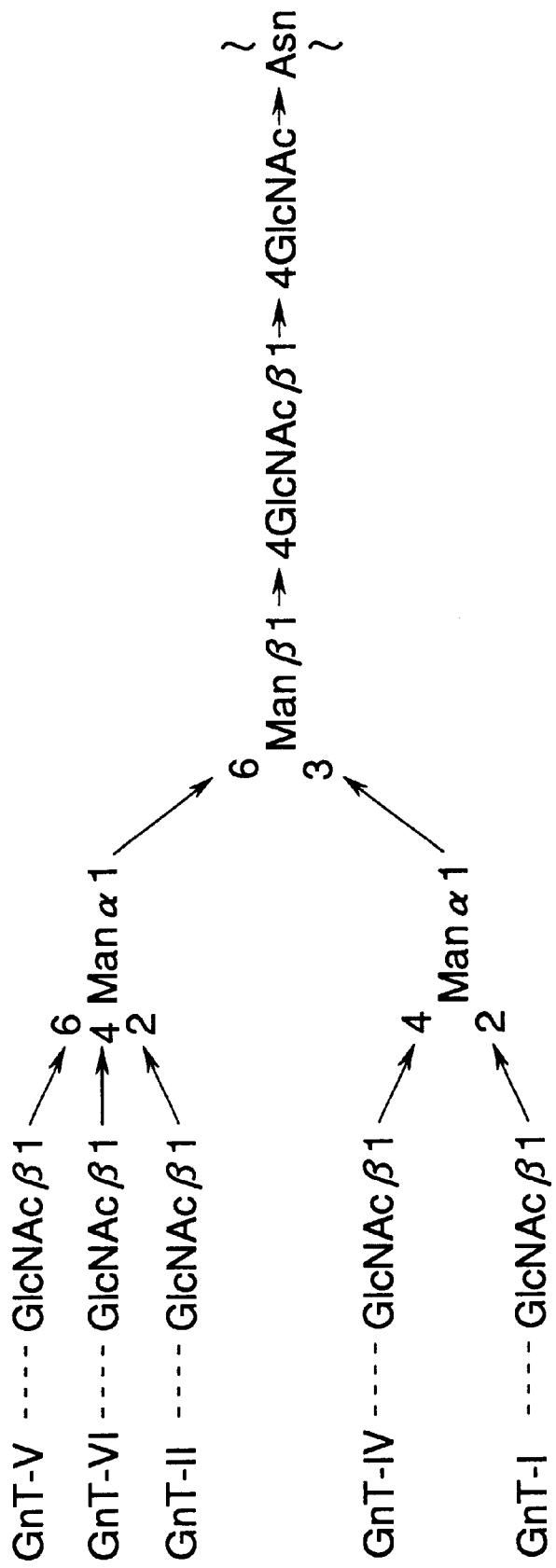

FIG. 3 shows the positions of GlcNAc transfer by various GlcNAc transferases (GlcNAc glycosyltransferases).

FIG. 4 shows the designations and structures of oligosaccharides.

Figure 5:
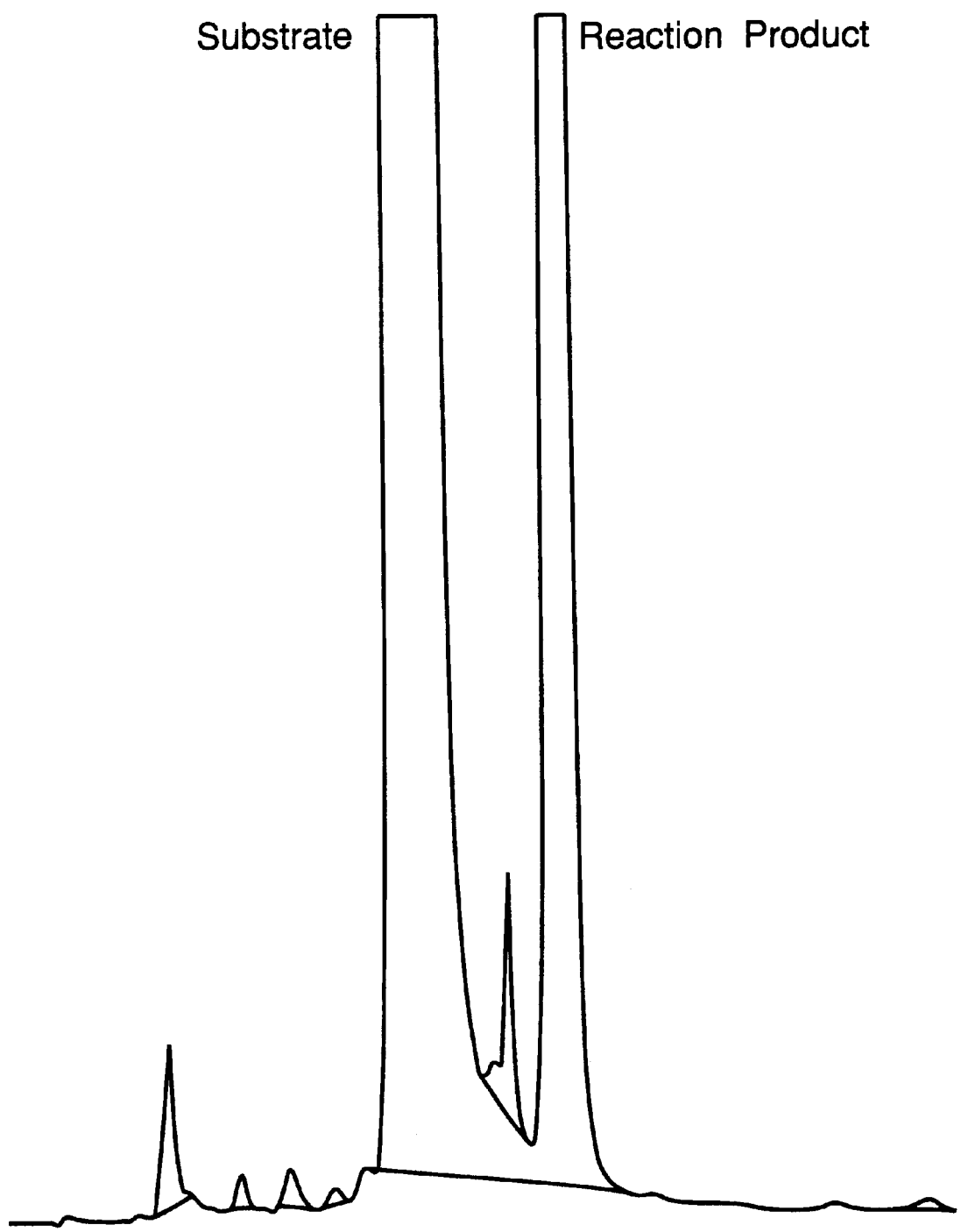

FIG. 5 shows a high performance liquid chromatogram for GnT-IV reaction products.

Figure 6:
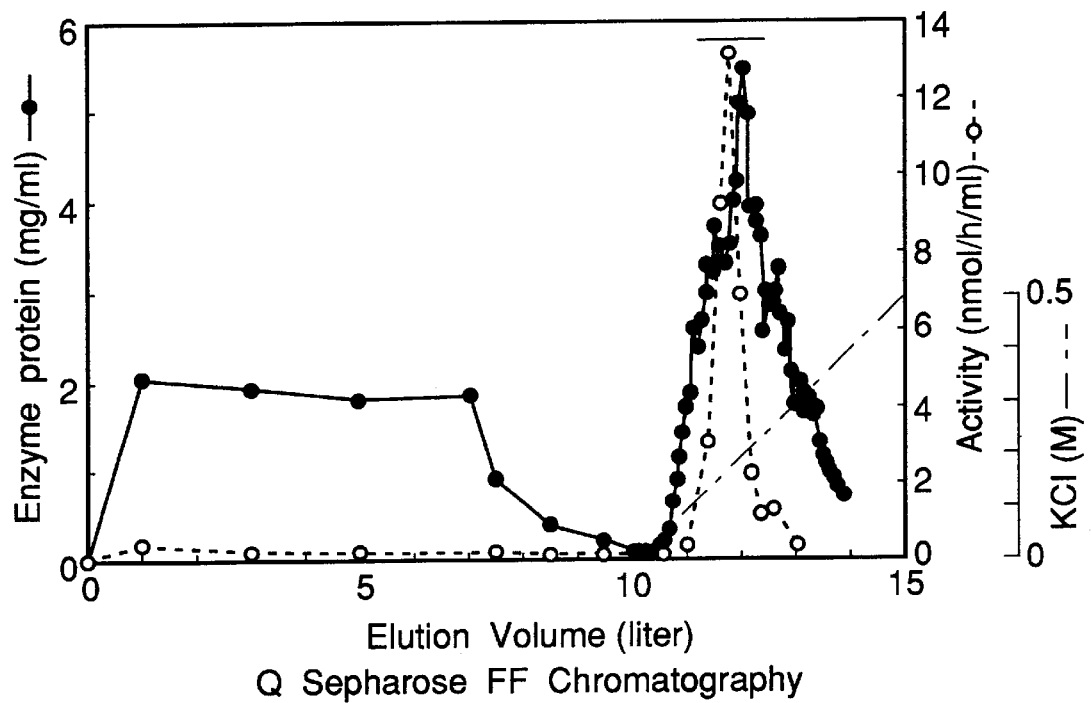

FIG. 6 shows the results of analysis of GnT-IV by Q-Sepharose FF chromatography.

Figure 7:
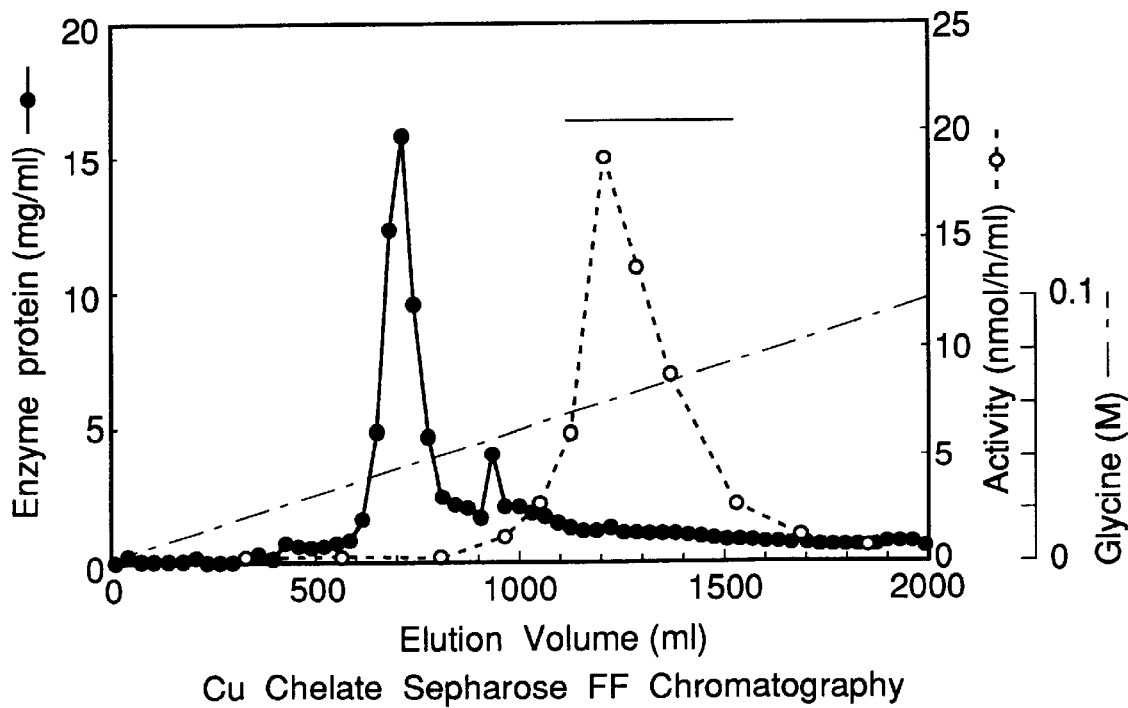

FIG. 7 show the results of analysis of GnT-IV by copper chelate Sepharose FF chromatography.

Figure 8:
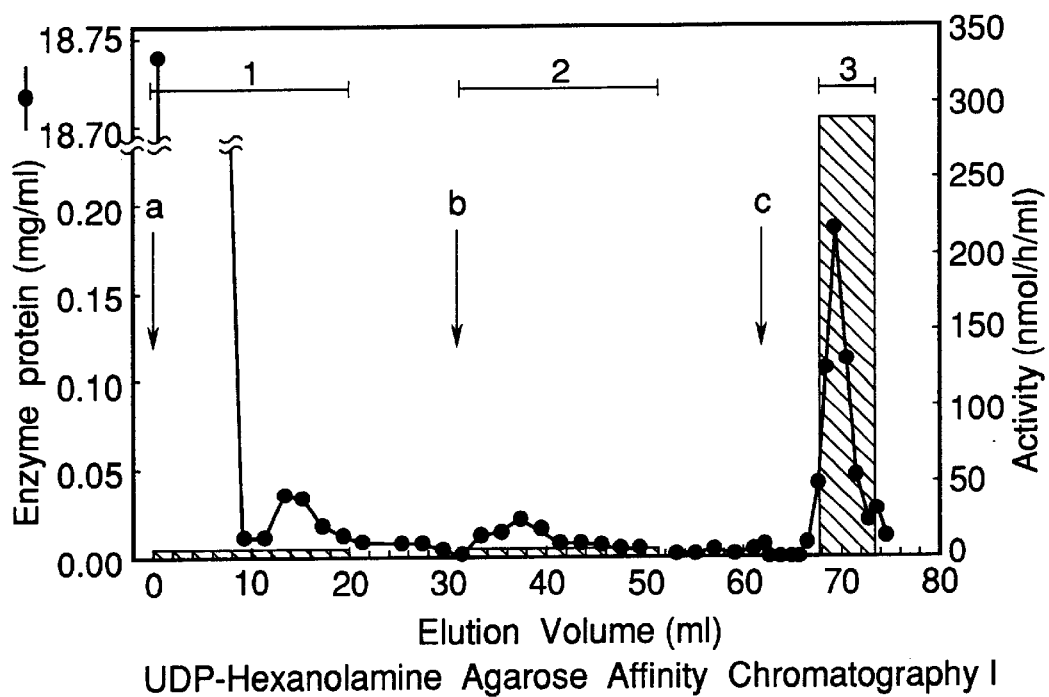

FIG. 8 shows the results of analysis of GnT-IV by UDP-Hexanolamine Agarose affinity chromatography (I).

Figure 9:
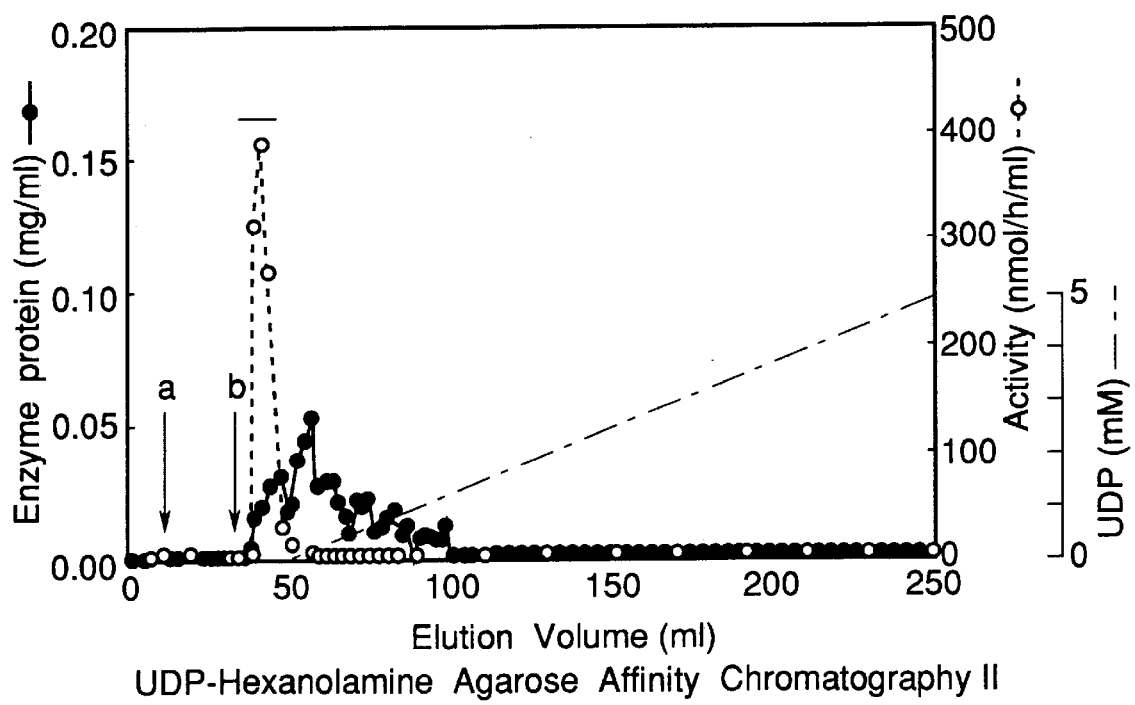

FIG. 9 shows the results of analysis of GnT-IV by UDP-Hexanolamine Agarose affinity chromatography (II).

Figure 10:
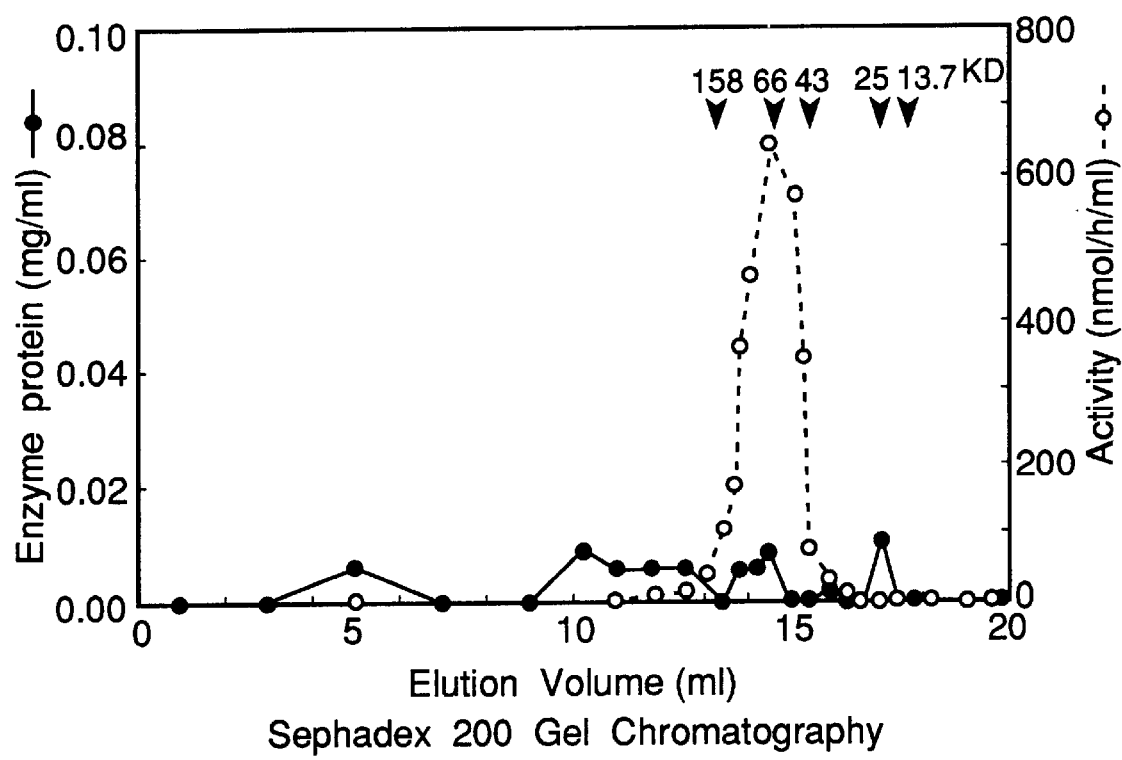

FIG. 10 shows the results of analysis of GnT-IV by Superdex 200 gel chromatography.

Figure 11:
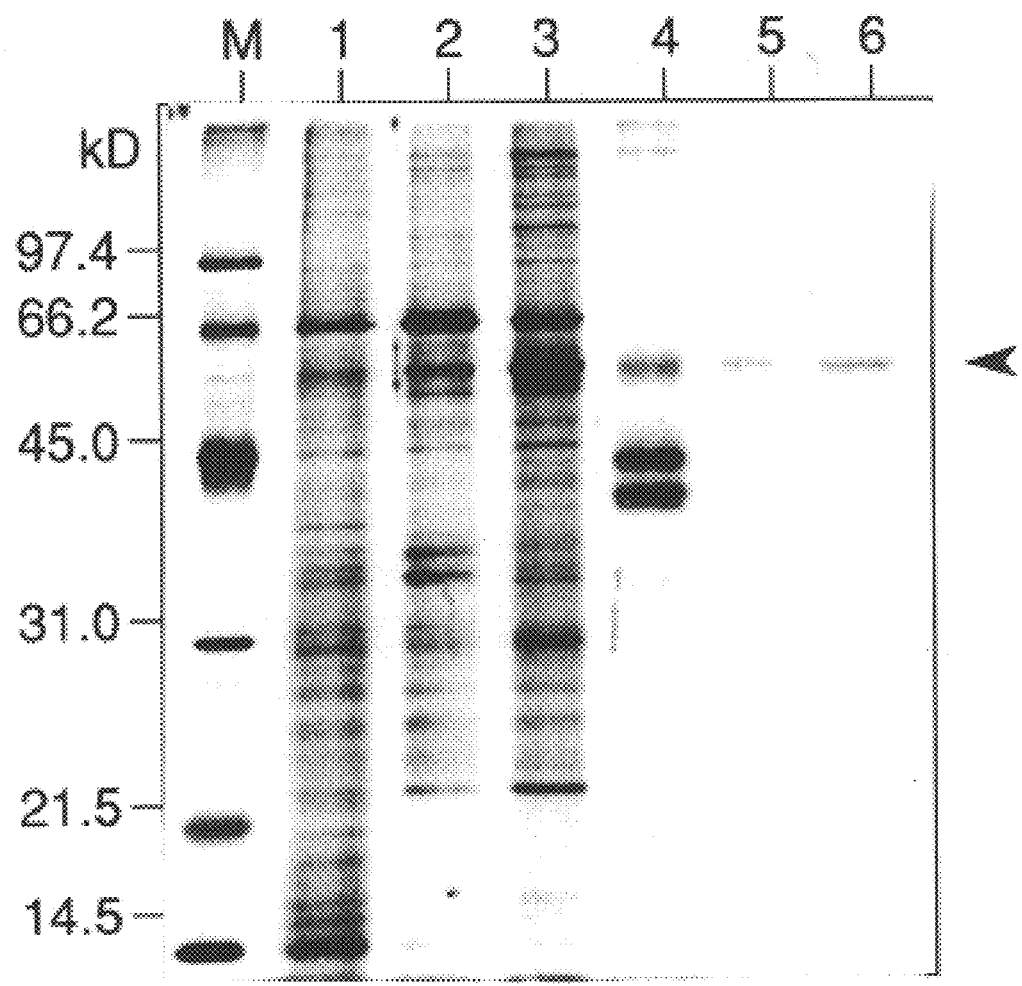

FIG. 11 is a photograph showing the results of SDS-PAGE (SDS polyacrylamide gel electrophoresis) of purified GnT-IV.

Figure 12:
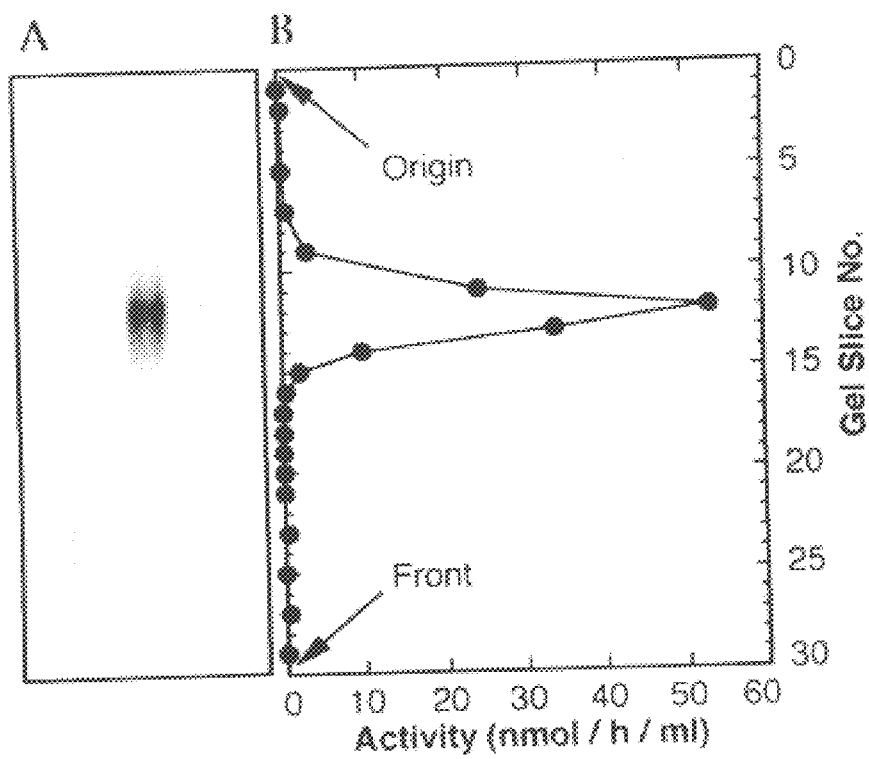

FIG. 12 shows the results of native gel electrophoresis of purified GnT-IV and the activity thereof.

Figure 13:
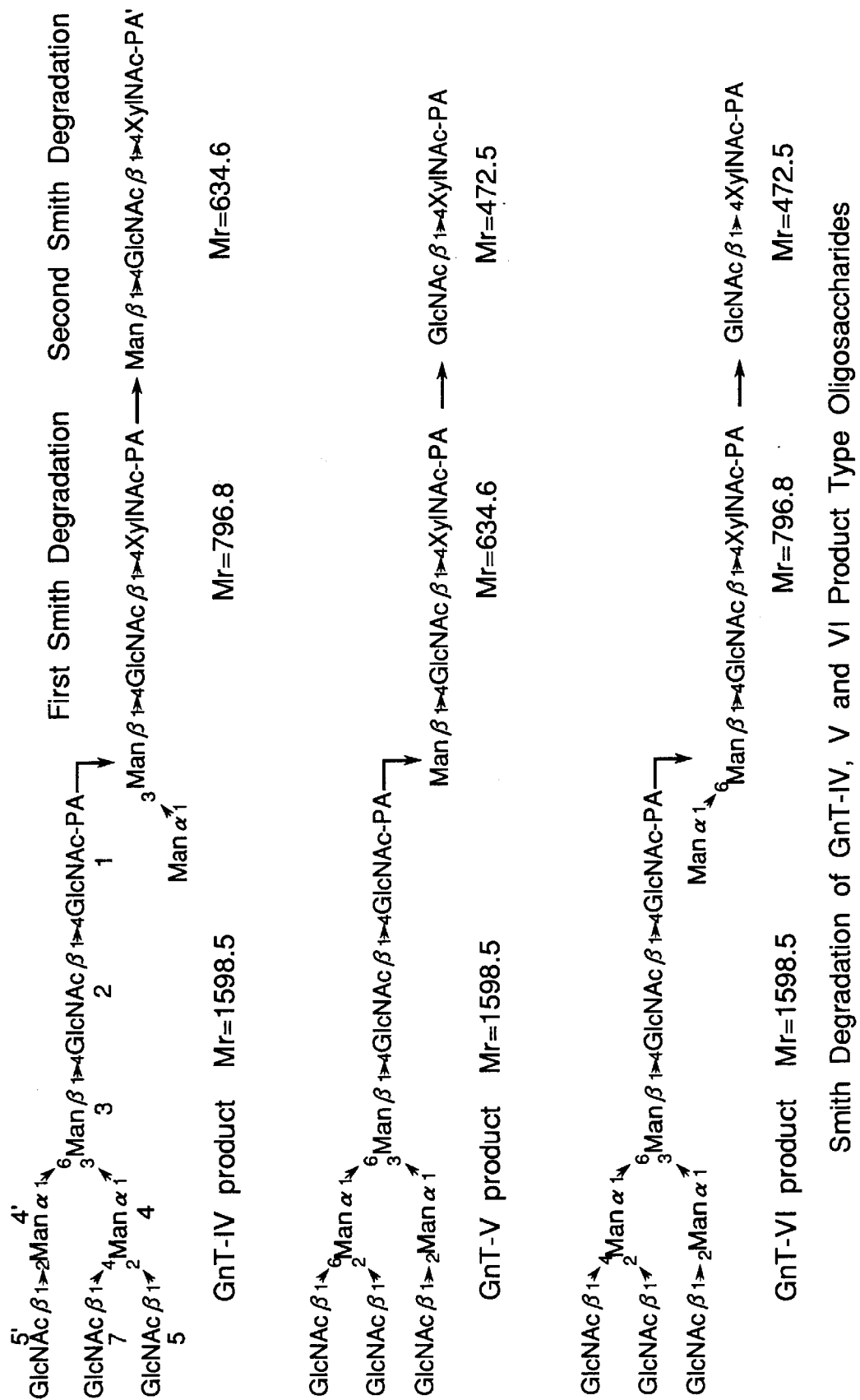

FIG. 13 shows Smith degradation profile of GnT-IV, -V and VI product type oligosaccharides.

Figure 14:
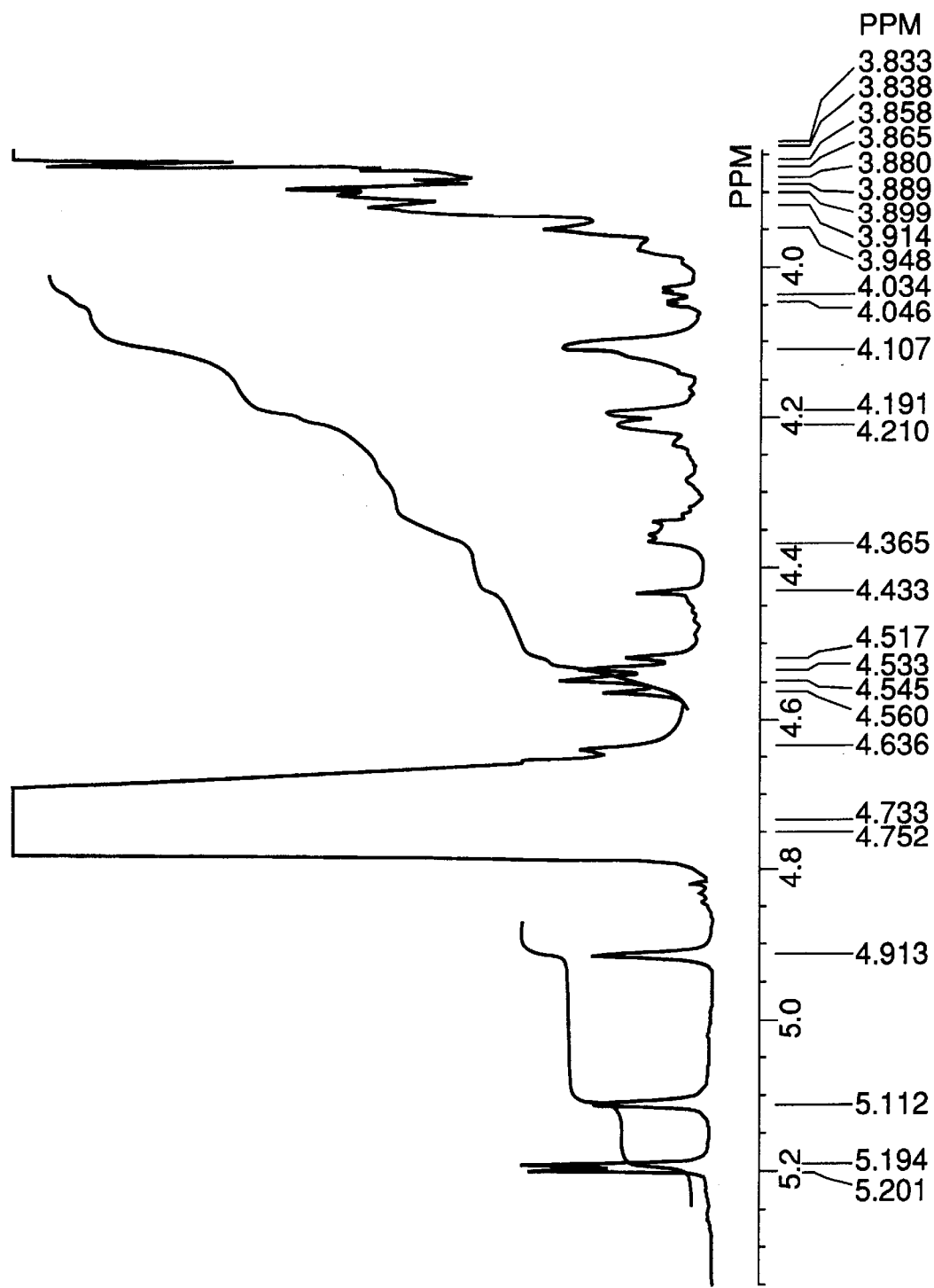

FIG. 14 shows the results of $^1$H-NMR (30° C.) of the GnT-IV reaction product.

Figure 15:
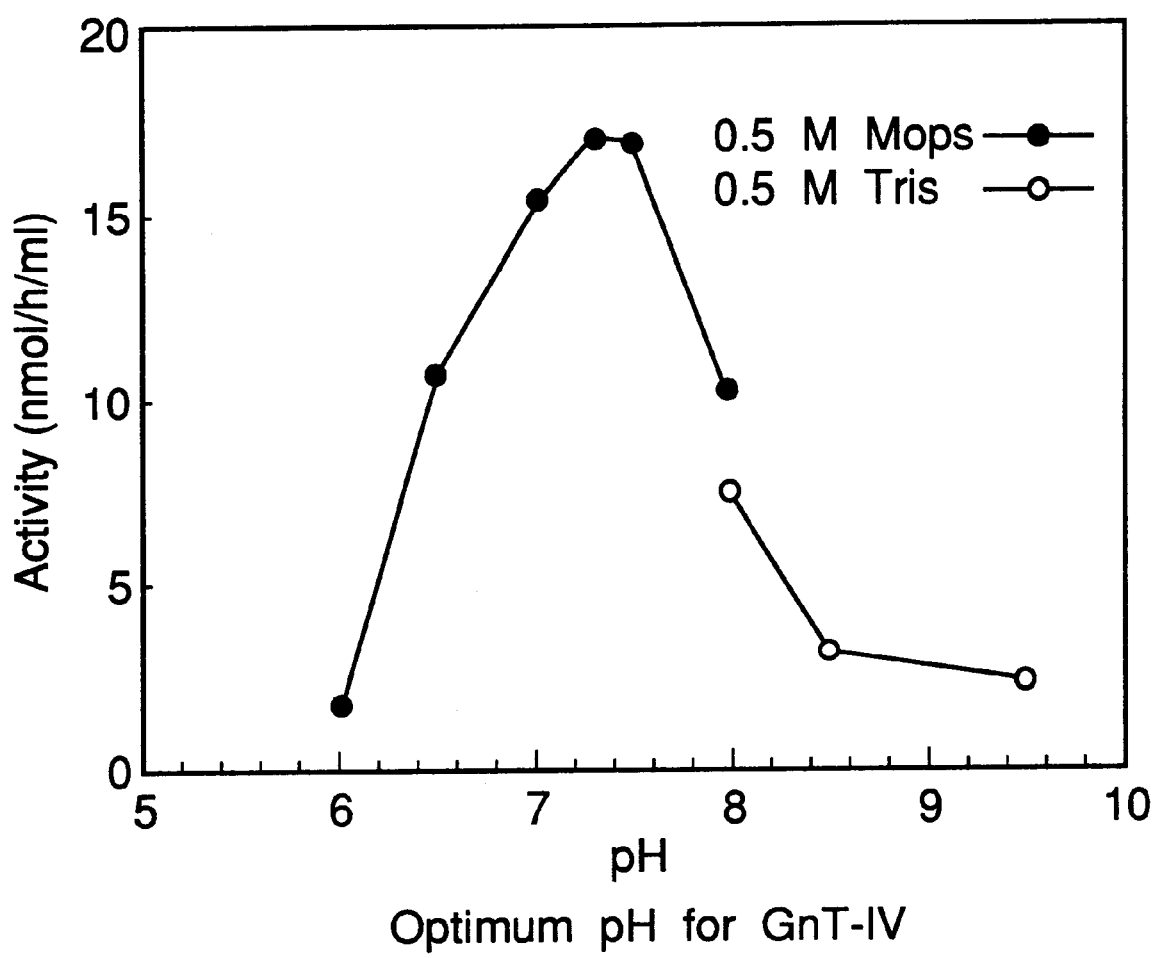

FIG. 15 shows the optimum pH for GnT-IV.

Figure 16:
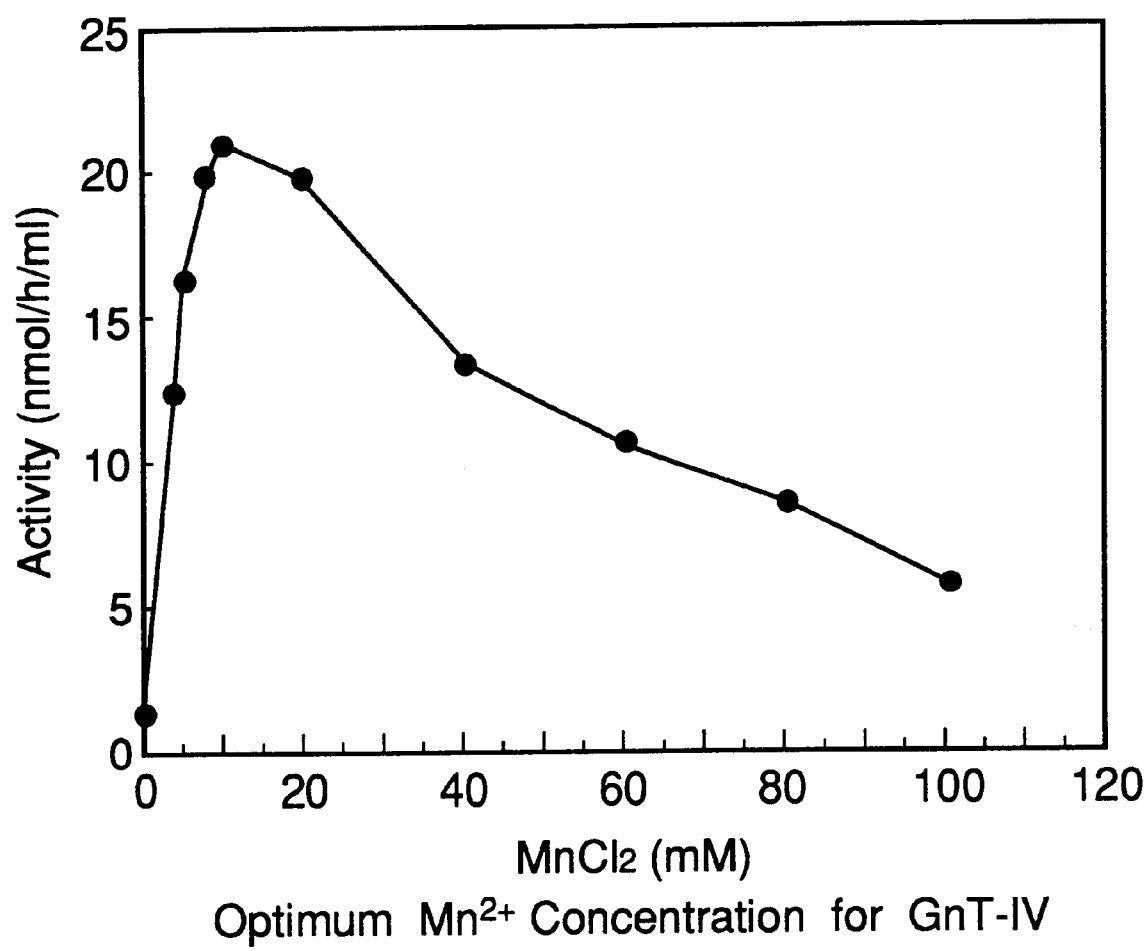

FIG. 16 shows the optimum Mn2+ concentration for GnT-IV.

Figure 17:
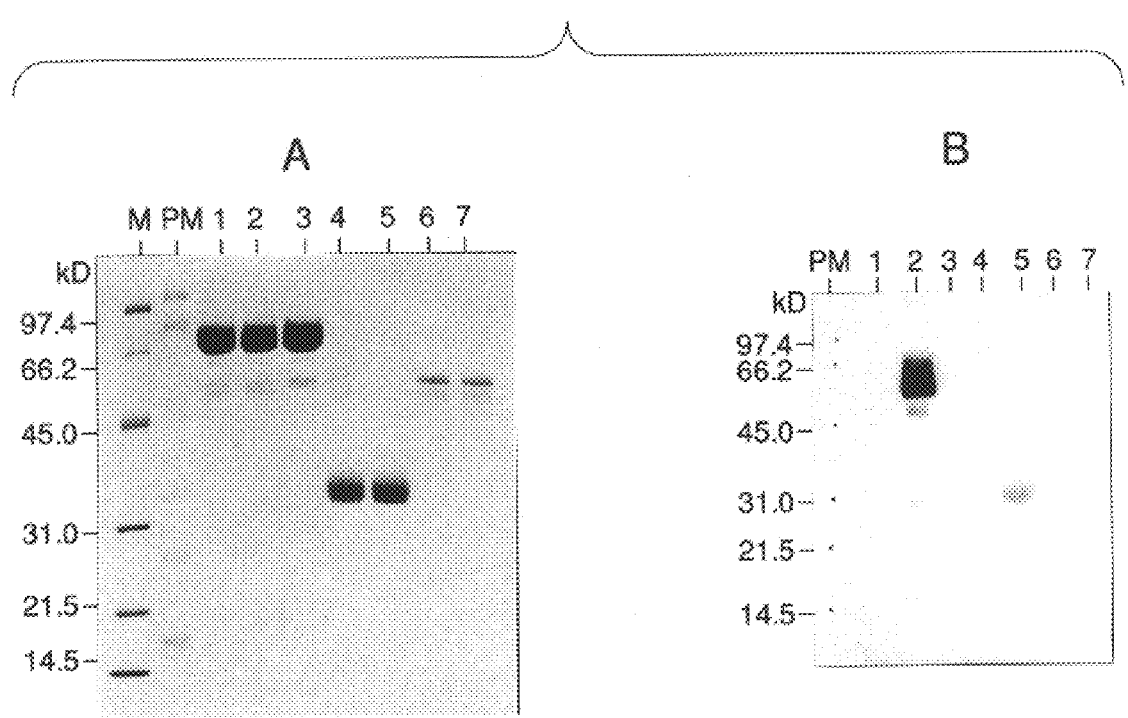

FIG. 17 shows the results of analysis by SDS-PAGE and fluorochromatography of glycoproteins which are the reaction products of GnT-IV.

Lanes 1 and 2: 7.6 μg of asialo agalacto human transferrin

Lane 3: 7.6 μg of asialo human transferrin

Lanes 4 and 5: 2.8 μg of asialo agalacto, CHO cell-derived recombinant human erythropoietin Lanes 6 and 7: 1.3 μg of asialo agalacto fetuin Lanes 1, 4 and 6 represent mock experiments in which reaction was performed without GnT-IV. M represents molecular markers (Bio-Rad). PM represents pre-stained molecular markers (Bio-Rad, USA).

GnT-IV reaction conditions: To 10 μl of a solution containing 0.702 mnol/hr of GnT-IV, a substrate glycoprotein equivalent to 1.6 nmol of biantennary type sugar chains (for fetuin alone, the sugar chain content was 1.6 nmol) and 450 nCi of UDP-[$^{14}$C] GlcNAc, an equal volume of an assay mixture (250 mM MOPS buffer, pH 7.3, 400 mM GlcNAc, 20% glycerol, 1.0% (w/v) Triton X-100, 15 mM MnCl$_2$, 1 mM UDP-GlcNAc) was added to obtain a reaction solution, which was incubated at 37° C. for 20 hours. One tenth of the resultant solution was analyzed by SDS-PAGE and fluorography.

For SDS-PAGE, 10–20% gradient gel (Daiichi Kagaku) was used. For fluorography, Amplify (Amersham) was used to expose the samples to X ray film for 20 hours.

Figure 18:
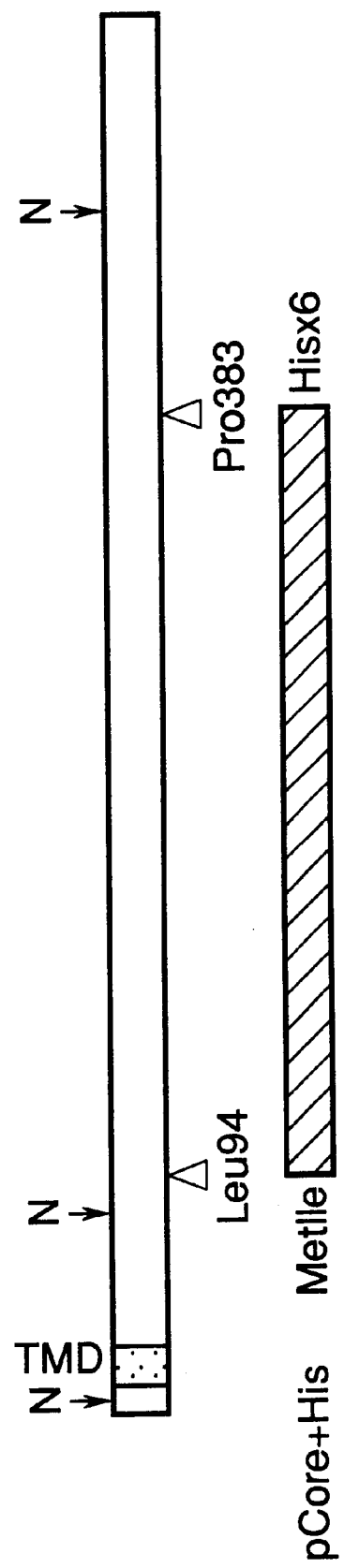

FIG. 18 shows the open reading frame of human GnT-IVa and the region contained in pCore-His expression vector.

Figure 19:
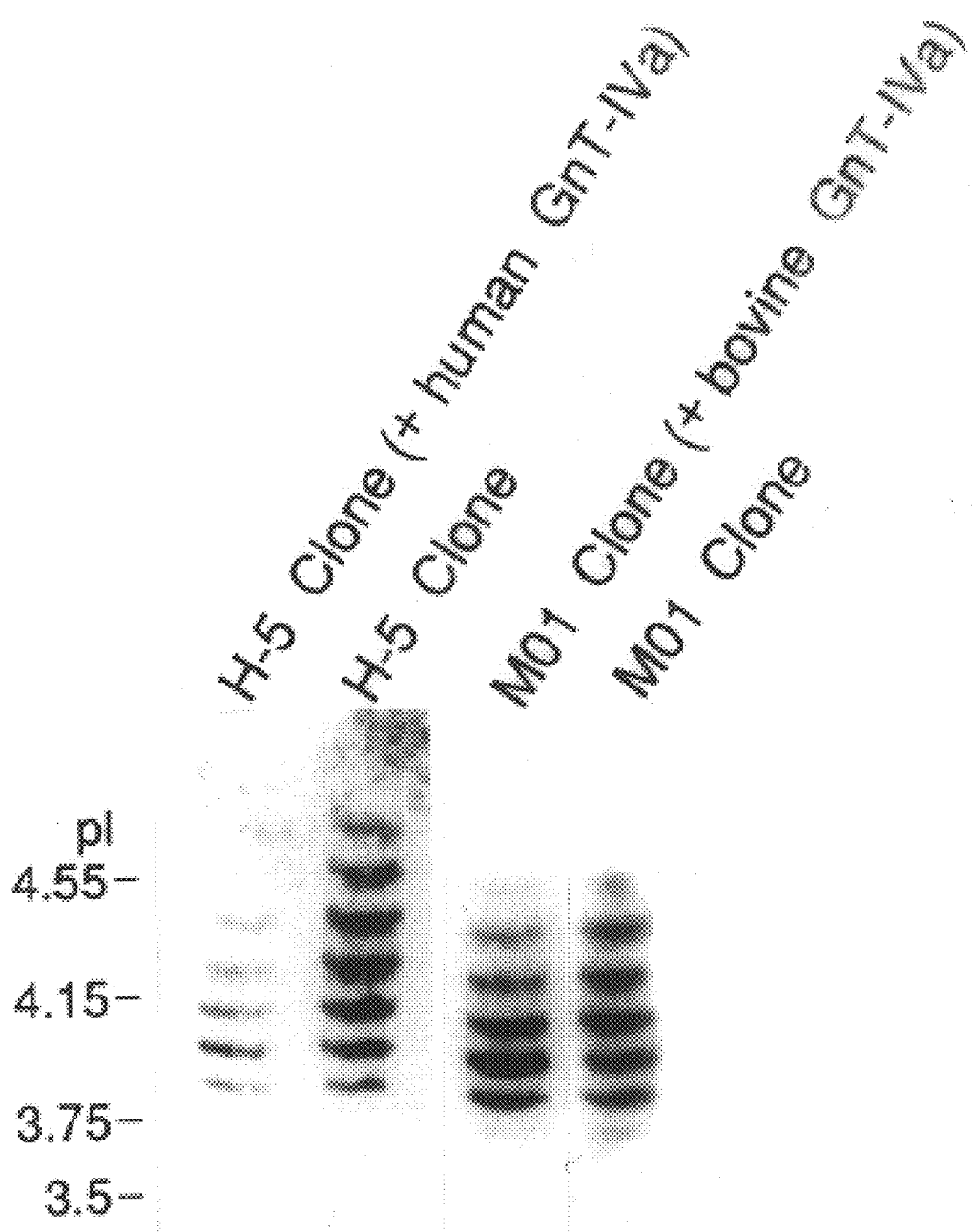

FIG. 19 shows the results of isoelectric focusing and Western analysis of erythropoietins produced by individual cell clones. Using two erythropoietin-producing strains and the same strains into which bovine and human GnT-IVa genes were introduced, respectively, the erythropoietin secreted by each strain was analyzed by isoelectric focusing and Western blotting using anti-erythropoietin antibody. On the left side, the positions of pI markers are shown.

BEST MODES FOR CARRYING OUT THE INVENTION

Hereinbelow, the present invention will be described in more detail with reference to the following Examples. However, the present invention is not limited to these Examples.

REFERENCE EXAMPLE 1

(1) Reagents Used in the Examples

Unless indicated otherwise, the reagents used were the highest grade products manufactured by Wako Purechemical Industries, Ltd.

(i) Pyridylaminated Oligosaccharides

Each of the pyridylaminated oligosaccharides used was obtained as described below. First, pyridylaminated oligosaccharides were prepared from human transferrin (apo type; Sigma, USA) according to the method of Tokugawa et al. [Biehuizen, M. F., Mattei, M. G. and Fukuda, M. (1993) Genes Dev., 7, 468–478]. The resultant material was treated with one or a combination of the following enzymes: Arethrobacter ureafaciens-derived sialidase (Nacalai Tesque), Asperugillus sp.-derived β-galactosidase (Toyobo), Jack bean-derived β-N-acetylhexosaminidase (Seikagaku Corp.), GnT-V active fraction in CHO-K1 cell extract (supernatant obtained by sonication of CHO-K1 cells in 2 volumes of 5 mM Tris-HCl buffer, pH 7.5, containing 2 mM MgCl$_2$ and 1 mM PMSF, and then centrifugation at 900×g for 10 min), and the GnT-V active fraction in the solubilized fraction from bovine small intestine homogenate (for the method of preparation, see "Preparation of the Microsome Fraction" and "Solubilization" in Example 1). A part of the pyridylaminated oligosaccharides were prepared by treating PA-Sugar Chain 021 and 022 (Takara Shuzo) with the above enzymes. In both cases, the oligosaccharides prepared were purified by reversed phase chromatography using an ODS column (10×250 mm; Vydac, USA) before use.

(ii) Glycoprotein Substrates

Bovine fetuin (Sigma, USA) and CHO cell-derived recombinant human erythropoietin (Kirin Brewery) were subjected to the following pretreatment to purify them into relatively uniform glycoform. Briefly, 40–100 mg of the glycoprotein was applied to a ConA-Sepharose column (5 ml; Pharmacia, Sweden) equilibrated with 10 mM Tris-HCl buffer, pH 7.4, containing 1 mM $MgCl_2$, 1 mM $CaCl_2$ and 0.15 M NaCl to thereby obtain a glycoform with a low biantennary sugar chain content as the non-adsorbed fraction. Thereafter, the column was eluted with the above buffer containing 1.0 M α-methyl mannoside (Nacalai Tesque) to thereby obtain the fraction adsorbing a glycoform with a high biantennary sugar chain content. Thus, fetuin with a low biantennary sugar chain content and erythropoietin with a high biantennary sugar chain content were obtained. With respect to human transferrin, there is no need to purify this glycoprotein since almost all sugar chains thereof are biantennary.

The thus obtained fetuin and human transferrin were individually reacted with 1 U of sialidase and 0 or 107 U of β-galactosidase in 1 ml of 0.4 M sodium acetate buffer, pH 5.0, containing 4 mM $MgCl_2$ at 37° C. for 16 hours to thereby obtain asialo or asialo agalacto glycoproteins. The erythropoietin with a high biantennary sugar chain content was reacted with 0.5 U of sialidase and 5 U of β-galactosidase in the same manner as described above to obtain an asialo agalacto glycoprotein.

Each of the thus obtained glycoprotein substrates was dialyzed against 50 mM ammonium acetate buffer, pH 7.3. Then, the amount of protein was determined with BCA protein assay (Pierce, USA) using BSA (bovine serum albumin) as a standard. Further, the protein was analyzed by SDS-PAGE (sodium dodesyl sulfate polyacrylamide gel electrophoresis). The thus prepared glycoproteins were used in the Examples.

(iii) RT-PCR (Reverse Transcription-Polymerase Chain Reaction)

For RT-PCR, Access RT-PCR System (Promega, USA) was used. For the amplification of a fragment of a gene of interest, Pfu polymerase (Stratagene, USA) was used.

(2) Equipment used in the Examples (i) Gene Sequencing

ABI PLISM 377 DNA Sequencer (Perkin-Elmer, USA) was used.

REFERENCE EXAMPLE 2

Specific Assay for GnT-IV Activity

Generally, there are two methods for assaying GnT-IV activity: a method in which the transfer of radiolabeled GlcNAc to an oligosaccharide substrate is examined and a method in which the transfer of GlcNAc to a labeled oligosaccharide substrate is fractionally analyzed by HPLC or the like. Taniguchi et al. developed a method in which GnT-III, -IV and -V activities are simultaneously determined using the GnT-II product type oligosaccharide as a receptor [Nishikawa, A., Fujii, S., Sugiyama, T. and Taniguchi, N. (1988) Anal. Biochem., 170, 349–354]. However, this assay method as it was inappropriate for the assay during purification of GnT-IV because the relative activity of GnT-IV is much lower than those of GnT-III and -V.

Then, the present inventors have developed a method for determining GnT-IV activity quantitatively and sensitively by increasing the amount of the acceptor pyridylaminated oligosaccharide to 10-fold compared to the amount used in the previous assay system [Tokugawa, K., Oguri, S. and Takeuchi, M. (1996) Glycoconjugate J., 13, 53–56]. Generally, it is very difficult to prepare such a large amount of acceptor oligosaccharides. However, according to the method of Tokugawa et al. [Tokugawa, K., Oguri, S. and Takeuchi, M. (1996) Glycoconjugate J., 13, 53–56], such oligosacchardes are readily prepared.

In Examples of the present invention, GnT-IV activity was assayed as described below.

The enzyme was reacted in 125 mM MOPS [3-(N-morpholino)propane-sulfonic acid] buffer, pH 7.3, containing 0.8 mM pyridylaminated oligosaccharide substrate (GnT-II product type oligosaccharide substrate), 20 mM UDP-GlcNAc, 7.5 mM $MnCl_2$, 200 mM GlcNAc, 0.5%(w/v) Triton X-100, 10% glycerol and 1% BSA at 37° C. for 4 hours. Then, the reaction was terminated by boiling the solution for 2 minutes. After removal of solids with a 0.45 nm filter, 5 µl of the filtrate was analyzed with an ODS-80TM column (4.6×150 mm; TOSO) (FIG. 5) at 50° C. with 50 mM ammonium acetate buffer, pH 4.0, containing 0.15% (w/v) n-butanol at a flow rate of 1.2 ml/min. The fluorescence of pyridylamino groups was detected using excitation at 320 nm and emission at 400 nm.

EXAMPLE 1

Isolation and Purification of the Enzyme (1) Screening of a Source of the Enzyme A source of the GnT-IV enzyme to be purified was searched for by utilizing the assay method described above. It was found that the relative activity of GnT-IV to those of GnT-III and GnT-V in bovine small intestine is rather higher than the relative activities of GnT-IV in any other tissues as shown in Table 1. Thus, bovine small intestine was selected as a starting material for purification.

TABLE 1

Search for Sources of GnT-IV Enzyme

|  |  | Specific Activity (pmol/h · mg-protein) | | |
|---|---|---|---|---|
| Source of the Enzyme | | IV | III | V |
| Cultured cells | CHO | 10.8 | 0 | 1097 |
|  | Bowes | 12.0 | 341 | 150 |
|  | AH66[1] | 2.0 | 634 | 30 |
|  | Solid AH[1] | 27 | 116 | 80 |
|  | Yoshida sarcoma[1] | 1.3 | 70 | 109 |
| Rat organs[1] | Small intestine | 17 | 280 | 68 |
|  | Heart | 9.4 | 11 | 10 |
|  | Spleen | 20 | 100 | 21 |
|  | Kidney | 1.9 | 1840 | 30 |
|  | Brain | 3.7 | 660 | 38 |
| Human[1] | Liver | 2.8 | 8.1 | 8.2 |
| Bovine organs | Small intestine | 25 | 174 | 41 |
|  | Heart | N.D. | N.D. | N.D. |
|  | Spleen | 10.9 | 0.7 | 10.9 |
| Colostrum |  | N.D. | N.D. | N.D. |

N.D. below detection limit
[1]data from Nishikawa, A. et al., BBA 1035, 313–318 (1990) addition of EDTA (ethylenediamine tetra-acetic acid). A divalent cation is essential for its activity. Among divalent cations, $Mn^{2+}$ shows the greatest effect, followed by $Co^{2+}$ and $Mg^{2+}$. Weak effect is recognized in $Ca^{2+}$ and $Fe^{2+}$. The optimum concentration of $Mn^{2+}$ is around 10 mM as shown in FIG. 16.

(2) Purification

Unless otherwise indicated, all the operations were performed at 4° C.

(i) Preparation of the Microsome Fraction

Two kilograms of bovine small intestine (obtained from a meat processor) was minced. Then, 4 volumes of an extraction buffer (10 mM Tris-HCl buffer, pH7.4, containing 0.25 M sucrose, 1 mM phenylmethylsulfonyl fluoride, 1 mM benzamidine hydrochloride, 1 mM dithiothreitol and 10 mg/ml antipain) was added thereto and homogenized with Polytron (Kinematica, Sweden). The resultant homogenate was centrifuged at 900×g for 10 minutes. Then, the supernatant was centrifuged further at 105,000×g for 60 minutes to thereby obtain the microsome fraction as a precipitate (Sample 1).

(ii) Solubilization

Sample 1 was suspended in 3 volumes of a solubilization buffer prepared by adding Triton-100 to the extraction buffer to give a final concentration of 1%. The supernatant was obtained by the centrifugation at 105,000×g for 60 minutes. The pellet was suspended again and collect the supernatant. The first and second extracts were combined (Sample 2).

(iii) Q-Sepharose FF Chromatography

Sample 2 was applied to Q-Sepharose FF Column (5×30 cm; Pharmacia, Sweden) pre-equilibrated with operation buffer 1 (20 mM Tris-HCl, pH 7.4, containing 1 mM benzamidine hydrochloride, 0.1% Triton X-100 and 20% glycerol) and then eluted by a linear gradient of 0–0.5 M KCl FIG. 6)(Sample 3).

(iv) Copper Chelate Sepharose FF Chromatography

Sample 3 was applied to Copper Chelate Sepharose FF Column (5×10 cm; Pharmacia, Sweden) pre-equilibrated with operation buffer 2 (obtainable by adding KCl to operation buffer 1 at a final concentration of 0.15 M). Then, non-adsorbed fractions were washed out with 5 volumes of operation buffer 2. Thereafter, the adsorbate was eluted by a linear gradient of 0.01 M glycine (FIG. 7). The resultant GnT-IV active fraction was pooled and concentrated with YM30 ultrafiltration membrane (Amicon, USA) (Sample 4).

(v) UDP-Hexanolamine Agarose Affinity Chromatography I

To UDP-Hexanolamine Agarose Affinity Column (1.2×4.5 cm; Sigma, USA) pre-equilibrated with operation buffer 3 (20 mM Tris-HCl, pH 8.0, containing 0.15 M KCl, 10 mM MnCl$_2$, 0.05% Triton X-100 and 20% glycerol), one half of Sample 4 dialyzed against 1 mM benzamidine hydrochloride-added operation buffer 3 was applied. Then, non-adsorbed fractions were washed out with operation buffer 4 (20 mM Tris-HCl, pH 8.0, containing 10 mM MnCl$_2$, 0.05% Triton X-100 and 20% glycerol). Thereafter, the adsorbate was eluted with operation buffer 4 to which 1 M (final concentration) KCl had been added (FIG. 8). The GnT-IV active fraction was pooled and dialyzed against operation buffer 5 (having the same composition as that of operation buffer 4 but having a pH of 7.4) (Sample 5).

(vi) UDP-Hexanolamine Agarose Affinity Chromatography II

Sample 5 was applied to UDP-Hexanolamine Agarose Affinity Column (1.0×6.5 cm; Sigma, USA) pre-equilibrated with operation buffer 5. Then, non-adsorbed fractions were washed out with operation buffer 5. Thereafter, the adsorbate was eluted with MnCl$_2$-removed operation buffer 5 (FIG. 9). The resultant GnT-IV active fraction was pooled (Sample 6).

(vii) Superdex 200 Gel Chromatography

Sample 6 was concentrated with a small Q-sepharose FF column and applied to Superdex 200HR5/5 Column (1×30 cm; Pharmacia, Sweden) pre-equilibrated with operation buffer 6 (obtained by adding KCl to operation buffer 5 at a final concentration of 0.15 M) (FIG. 10). Operation buffer 6 was applied to the column at a flow rate of 0.25 ml/min to thereby obtain the GnT-IV active fraction (Sample 7).

(viii) The amount of protein, activity and specific activity in each purification step are summarized in Table 2. The final sample was purified 224,000-fold compared to the small intestine homogenate.

TABLE 2

Purification of GnT-IV

| Purification Step | Amount of protein (mg) | Total enzyme activity (nmol/h) | Specific activity (nmol/h/mg) | Yield (%) | Purification factor (−fold) |
|---|---|---|---|---|---|
| Bovine small intestine homogenate | 112,900 | 49,500 | 0.44 | 100 | 1 |
| Solubilized fraction | 24,100 | 14,500 | 0.60 | 29 | 1.4 |
| Q-Sepharose | 4,000 | 7,200 | 1.80 | 14 | 4.1 |
| Cu Chelate Sepharose | 450 | 3,670 | 8.10 | 7.4 | 18.4 |
| UDP-Hexanolamine I | 0.59 | 1,950 | 3,310 | 3.9 | 7,510 |
| UDP-Hexanolamine II | 0.035 | 1,420 | 40,600 | 2.9 | 92,200 |
| Superdex 200 | 0.008 | 790 | 98,800 | 1.6 | 224,000 |

Started from 2 kg of bovine small intestine.

(3) Properties in Terms of Enzyme Chemistry and Protein Chemistry

(i) Purity

Sample 7 gave a single band at a molecular weight of 60 K in SDS-PAGE (FIG. 11). When Sample 7 was subjected to native-PAGE and the resultant band was cut out from the gel to determine GnT-IV activity, the location of the protein band agreed with the location of the activity (FIG. 12). Furthermore, any of GnT-I, -II -III or -V activity was not detected in Sample 7. From these findings, it was concluded that Sample 7 is pure GnT-IV. Taking into account that the apparent molecular weight of this protein was 77 K as determined by Triton X-100-containing gel filtration (FIG. 10), it is thought that GnT-IV does not have a subunit structure and expresses its activity in the form of a monomer. Whe n Sample 7 was treated wi th Peptide N-Glycosidase F (Boehringer-Mannheim, Germany), an increase in mobility was observed on SDS-PAGE. Thus, it is thought that GnT-IV from bovine small intestine is a glycoprotein having at least Asn-linked sugar chains.

(ii) Reaction Specificity

When this enzyme reacts on the GnT-II product type oligosaccharide represented by th e formula below as a substrate:

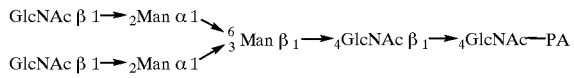

under the standard assay conditions, the enzyme yielded a single product (pyridylaminated oligosaccharide 1) as assayed by HPLC.

This product was collected, followed by determination of its structure by (i) a combination of Smith degradation and laser TOF-MS (time-of-flight mass spectrometer) and (ii) $^1$H-NMR. Thus, the reaction specificity of this enzyme was examined. When pyridylaminated oligosaccharide 1 was subjected to Smith degradation according to the method of Kobata and Takasaki [Kobata, A. and Takasaki, S. (1993) in Glycobiology "A Practical Approach" (Fukuda, M. and Kobata, A., eds) 165–185, IRL Press, Oxford, England], its mass number changed from 1599.0 to 795.30 as a result of the first degradation and further changed to 634.68 as a result of the second degradation. This agrees to the reaction pathway as shown in FIG. 13. Thus, it was concluded that the reaction product of this enzyme has the following structure:

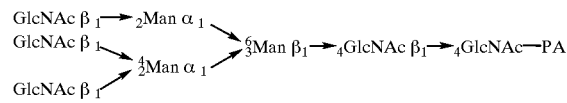

Further, when pyridylaminated oligosaccharide 1 was subjected to $^1$H-NMR, a peak of 4.53 ppm which corresponds to the anomeric proton of GlcNAc7 shown in the following formula was detected; its coupling constant J1, 2 was 7.9 Hz (FIG. 14). These results indicate that GlcNAc7 is, as shown in the formula below, attached to position 4 of Man4 via β-type linkage, supporting the above structure completely.

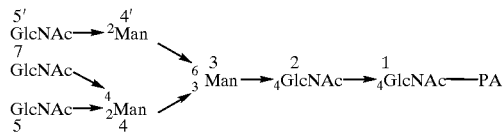

(iii) Optimum pH

The optimum pH of this enzyme is around 7.5 as shown in FIG. 15.

(iv) Requirement of Divalent Cation

As shown in Table 3, this enzyme is deactivated by the addition of EDTA (ethylenediamine tetra-acetic acid). A divalent cation is essential for its activity. Among divalent cations, $Mn^{2+}$ shows the greatest effect, followed by $Co^{2+}$ and $Mg^{2+}$. Weak effect is recognized in $Ca^{2+}$ and $Fe^{2+}$. The optimum concentration of $Mn^{2+}$ is around 10 mM as shown in FIG. 16.

TABLE 3

Divalent Cation Requirement of GnT-IV

| Additive | Activity (%) |
| --- | --- |
| None | 5.6 |
| EDTA | 0 |
| $MnCl_2$ | 100 |
| $CoCl_2$ | 74.8 |

TABLE 3-continued

Divalent Cation Requirement of GnT-IV

| Additive | Activity (%) |
| --- | --- |
| $MgCl_2$ | 72.5 |
| $CaCl_2$ | 7.2 |
| $FeCl_2$ | 9.8 |
| $CuCl_2$ | 0 |

GnT-IV activity was determined by adding each of the metal ions (10 mM) to a GnT-IV sample from which metal ions had been removed. GnT-IV activity is represented in per cent in the Table, wherein the activity when 10 mM $MnCl_2$ was added is regarded as 100%.

(v) Inhibition by Sugar Nucleotides

As shown in Table 4, UDP inhibited the activity of this enzyme most strongly. The inhibitory effects of UDP-glucose, UDP-GalNAc, 2'-deoxy-UDP and UDP-hexanolamine (Sigma, USA) followed that of UDP in this order. Uridine, UMP, TDP and CDP exhibited little inhibitory effect.

TABLE 4

Inhibition of GnT-IV by Nucleotides

| Additive | Activity (%) |
| --- | --- |
| None | 100 |
| Uridine | 115 |
| UMP | 97.3 |
| UDP | 27.3 |
| UTP | 88.2 |
| TDP | 110 |
| CDP | 112 |
| 2'-deoxy-UDP | 67.4 |
| UDP-hexanolamine | 73.6 |
| UDP-glucose | 56.6 |
| UDP-galactose | 87.3 |
| UDP-glucuronic acid | 92.3 |
| UDP-N-acetylgalactosamine | 59.7 |

GnT-IV activity when each nucleotide (2 mM) was added in the presence of 0.5 mM UDP-GlcNAc is expressed in per cent in the Table, wherein the activity when nothing was added is regarded as 100%.

(vi) Substrate Specificity

As shown in Table 5, this enzyme preferred the GnT-V product type oligosaccharide (E in Table 5) the most as an acceptor. Next to this, the enzyme preferred the GnT-II product type oligosaccharides (D in Table 5).

When the reactivity of this enzyme toward the GnT-II type oligosaccharide is regarded as 100%, this enzyme exhibits reactivities of 0% and 54% toward the core type oligosaccharides (A in Table 5) and the GnT-I product type oligosaccharides (C in Table 5), respectively.

This enzyme exhibits a reactivity of 46% toward a structure of GnT-II product type oligosaccharide in which fucose is attached via α1→6 linkage to the GlcNAc at the reducing terminus (F in Table 5).

This enzyme exhibits a reactivity of 0% toward a structure of GnT-II product type oligosaccharides in which the GlcNAc on the α1→3 mannose is lacking (B in Table 5).

This enzyme exhibits a reactivity of 16% toward a structure of GnT-II product type oligosaccharides in which galactose is attached via β1→4 linkage to the GlcNAc on the α1→6 mannose (G in Table 5), and a reactivity of 0% toward a structure of GnT-II product type oligosaccharide in which galactose is attached via β1→4 linkage to the GlcNAc on the α1→3 mannose (H and I in Table 5).

This enzyme exhibits a reactivity of 0% toward a structure of GnT-II product type oligosaccharides in which GlcNAc is attached via β1→4 linkage to the β1→4 mannose (J in Table 5).

The substrate specificity of this enzyme as described above almost agree with the substrate specificity of GnT-IV predicted by Schachter et al. [Glesson, P. A. and Schachter, H. (1983) J. Biol. Chem., 258, 6162–6173]. Thus, it has become clear that this enzyme of the invention is the very GnT-IV that has long been a missing link in the biosynthesis of complex type sugar chains.

TABLE 5

| | Receptor Oligosaccharide | Relative Activity of GlcNAc Transfer (%) |
|---|---|---|
| A | Man α1→6, Man α1→3 Man β1→$_4$GlcNAc β1→$_4$GlcNAc—PA | 0 |
| B | GlcNAc β1→$_2$Man α1→6, Man α1→3 Man β1→$_4$GlcNAc β1→$_4$GlcNAc—PA | 0 |
| C | Man α1→6, GlcNAc β1→$_2$Man α1→3 Man β1→$_4$GlcNAc β1→$_4$GlcNAc—PA | 54 |
| D | GlcNAc β1→$_2$Man α1→6, GlcNAc β1→$_2$Man α1→3 Man β1→$_4$GlcNAc β1→$_4$GlcNAc—PA | 100 |
| E | GlcNAc β1→6, GlcNAc β1→$_2$Man→6, GlcNAc β1→$_2$Man→3 Man β1→$_4$GlcNAc β1→$_4$GlcNAc—PA | 164 |
| F | GlcNAc β1→$_2$Man α1→6, GlcNAc β1→$_2$Man α1→3 Man β1→$_4$GlcNAc β1→$_4$GlcNAc(Fuc α1→6)—PA | 46 |
| G | Gal β1→$_4$GlcNAc β1→$_2$Man α1→6, GlcNAc β1→$_2$Man α1→3 Man β1→$_4$GlcNAc β1→$_4$GlcNAc—PA | 16 |
| H | GlcNAc β1→$_2$Man α1→6, Gal β1→$_4$GlcNAc β1→$_2$Man α1→3 Man β1→$_4$GlcNAc β1→$_4$GlcNAc—PA | 0 |

TABLE 5-continued

| Receptor Oligosaccharide | Relative Activity of GlcNAc Transfer (%) |
|---|---|
| I  Galβ1→4GlcNAcβ1→2Manα1⟶6(Manβ1→4GlcNAcβ1→4GlcNAc—PA), Galβ1→4GlcNAcβ1→2Manα1⟶3 | 0 |
| J  GlcNAcβ1→2Manα1⟶6, GlcNAcβ1→4(Manβ1→4GlcNAcβ1→4GlcNAc—PA), GlcNAcβ1→2Manα1⟶3 | 0 |

(vii) Kinetic Parameters

Under the assay conditions as described in Reference Example 2, the Km and Vmax values of this enzyme toward the GnT-II product type oligosaccharides were 0.73 mM and 3.23 μM/min, respectively, and these values toward the GnT-V product type oligosaccharides were 0.13 mM and 1.75 μM/min, respectively. The Km value toward the UDP-GlcNAc was 0.22 mM.

Among the pyridylaminated oligosaccharides obtained, those represented by the following formulas were found to be novel oligosaccharides:

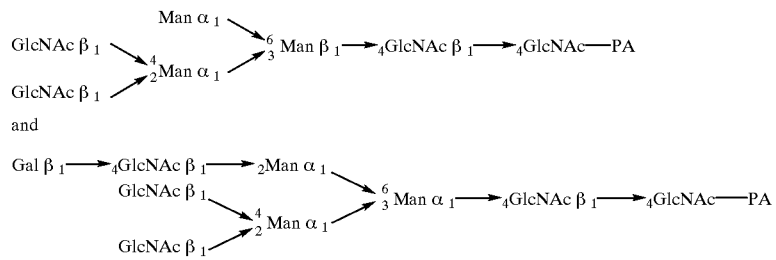

and (viii) Action on Glycoproteins

In order to demonstrate that GnT-IV can act on not only oligosaccharide substrates but also oligosaccharide chains on glycoproteins, GnT-Iv reacts on asialo agalacto glycoproteins using UDP-[$^{14}$C] GlcNAc as a sugar donor. Then, the reaction products were analyzed by SDS-PAGE and fluorography (Panels A and B, FIG. 17). As shown in lanes 2 and 5 of Panel B in FIG. 17, transfer of [$^{14}$C] GlcNAc to asialo agalacto human transferrin and asialo agalacto, CHO cell-derived recombinant human erythropoietin.

The human transferrin having the GnT-IV product type sugar chain (of the following formula) obtained by this GnT-IV reaction is a novel substance which does not occur in nature.

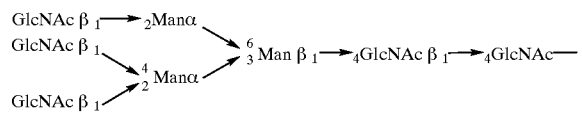

EXAMPLE 2

Peptide Mapping Analysis

About 1 mg of this enzyme of the invention finally purified was electrophoresed on 0.1% SDS-10% polyacrylamide gel according to the method of Laemmli [Laemmli, U. K. Nature (1970) 313, 756–762]. The separated proteins were electroblotted onto a PVDF membrane. The protein fixed on the membrane was S-carboxymethylated and then digested with lysylendopeptidase Achromobacter protease I (AP-I) (Wako Pure Chemical Industries, Ltd) to obtain an AP-I-digested fragment mixture. The AP-I-digested PVDF membrane was further digested with Asp-N (Takara Shuzo) to obtain an Asp-N-digested fragment mixture. Each of the peptide fragment mixtures was separated by high performance liquid chromatography and subjected to amino acid sequence analysis. As a result, the sequences shown in SEQ ID NOS: 1–14 were obtained.

EXAMPLE 3

Isolation and Identification of Bovine GnT-IVa cDNA (1) RT-PCR

Based on the amino acid sequences shown in SEQ ID NOS: 7 and 11 obtained in Example 2, oligomer AP-5F shown in SEQ ID NO: 15 and oligomer DN-9R shown in SEQ ID NO: 16 were synthesized respectively. An RT-PCR was performed using as a template the total RNA extracted from bovine small intestine tissue by the guanidium isothiocyanate method and using the above primers. As a result, an amplified fragment of about 170 bp which seemed specific was obtained. This fragment was subcloned.

(2) Screening of a Library

A bovine small intestine cDNA library (Clontech, USA) was screened with the above-mentioned RT-PCR product to obtain four positive plaques. The nucleotide sequences of these clones were determined. The resultant sequences contained a number of nucleotide sequences coding for some of the partial amino acid sequences (SEQ ID NOS: 1–14) obtained in Example 2, and also contained a sequence appearing to be a termination codon. Using a fragment of 150 bp representing the most upstream region of the resultant nucleotide sequence, the library was screened again to obtain two positive plaques. The nucleotide sequences of these clones were determined. Then, the library was further screened similarly with a probe of 150 bp of the most upstream region, however, new clones were not obtained.

(3) 5' RACE (Rapid Amplification of the cDNA Ends)

Subsequently, 5' RACE was performed in order to obtain a full-length cDNA. Using the sequence of the most upstream region obtained by the phage screening, the first 5' RACE was performed. However, an initiation codon could not be found. Then, based on the sequence obtained by the first 5' RACE, the second 5' RACE was performed to thereby obtain a sequence containing an initiation codon. This sequence was ligated to the previously obtained partial gene sequence of the phage clone to thereby obtain a gene fragment containing an intact open reading frame (Gene 1). The nucleotide sequence for the thus obtained gene fragment is shown in SEQ ID NO: 17, and the amino acid sequence deduced therefrom is shown in SEQ ID NO: 18. It was confirmed that this DNA fragment contains all of the nucleotide sequences coding for the 14 partial amino acid sequences (SEQ ID NOS: 1–14) obtained in Example 2.

EXAMPLE 4

Construction of an Expression Vector using the Cloned Bovine GnT-IVa Gene and a Method for Producing GnT-IVa Enzyme (1) Construction of a Vector A primer (SEQ ID NO: 19) which introduces an XhoI site into a region upstream of the initiation codon of Gene 1 and another primer (SEQ ID NO: 20) which introduces an XbaI site into a region downstream of the termination codon of the gene were synthesized. Then, the entire gene coding for GnT-IV enzyme was amplified by PCR with the primers. The amplified fragment obtained was digested with XhoI and XbaI, and inserted between the XhoI and XbaI sites of pSVL vector (Pharmacia, Sweden) to prepare plasmid pBGT4.

(2) Introduction into COS7 Cells

Plasmid pBGT4 was introduced into COS7 cells (RIKEN Cell Bank) by electroporation. Briefly, 10 µg of the plasmid was added to approximately 5×10$^6$ cells in 0.8 ml of PBS(−) (Nissui Pharmaceutical Co.). A voltage of 1600 V was applied at a capacitance of 25 µF with a gene pulser (BioRad, USA) at room temperature to introduce the gene into the cells. The resultant cells were transferred to a 90 mm laboratory dish and cultured in 10 ml of Dulbecco's modified Eagle's medium (Base Catalogue No. 12430, Life Technologies, Inc., USA) containing 10% fetal bovine serum under 5% $CO_2$ at 37° C. for 72 hours. Thereafter, the cells were recovered and suspended in 100 µl of a buffer (5 mM Tris-HCl, pH 7.5, 2 mM $MgCl_2$, 1 mM phenylmethylsulfonyl fluoride), followed by sonication and centrifugation at 2000×g for 5 minutes. Thus, a cell extract was obtained.

(3) Assay of GnT-IV Activity

GnT-IV activity in the cell extract was determined by the method described in Reference Example 2. The results are shown in Table 6. Compared to the extract from cells into which PSVL vector was introduced as a control, the extracts into which plasmid pBGT4 was introduced exhibited 44–78 times higher GnT-IV activity per cell. From these results, it was confirmed that Gene 1 encodes GnT-IV enzyme. Thus, GnT-IV enzyme can be produced by cultured cells according to this method.

TABLE 6

| Plasmid | Specific Activity (pmol/hr/mg protein) | Activity Ratio |
| --- | --- | --- |
| pSVL | 409 | 1 |
| pBGT4(#1) | 29623 | 72 |
| pBGT4(#2) | 31773 | 78 |
| pBGT4(#3) | 20182 | 44 |

Reaction time: 4 hours
Activity ratios are expressed in relation to the total activity of pSVL that is regarded as 1.

EXAMPLE 5

Isolation and Identification of Human GnT-IVa cDNA (1) RT-PCR

Based on the nucleotide sequence of bovine GnT-IVa obtained in Example 3, primer h1-2F shown in SEQ ID NO: 21 and primer h1-1R shown in SEQ ID NO: 22 were synthesized. Using total RNA from human liver (Clontech, USA) as a template, an RT-PCR was performed with the above primers. As a result, an amplified fragment of about 650 bp which seemed to be specific was obtained. This fragment was subcloned, and the nucleotide sequence thereof was determined.

(2) screening of a Library

A CDNA library from human liver (Clontech, USA) was screened using the 685 bp DNA fragment obtained by the above RT-PCR as a probe.

Two positive plaques of hGT4/λgt10-1 and hGT4/λgt10-2 were obtained. The nucleotide sequences of the inserts in these phage clones were determined. As a result, hGT4/λgt10-1 contained a 804 bp DNA region and hGT4/λgt10-2 contained a 2115 bp DNA region. The former region was entirely included in the latter region. As shown in SEQ ID NO: 23, the DNA fragment contained in hGT4/λgt10-2 had an open reading frame (ORF) highly homologous to the amino acid sequence of bovine GnT-IVa (96% identical). From the results described in Example 6, it was confirmed that this ORF is human GnT-IVa gene. The amino acid sequence of this ORF is shown in SEQ ID NO: 24.

EXAMPLE 6

Construction of an Expression Plasmid for Human GnT-IVa Gene and a Method for Producing Human GnT-IVa Enzyme (1) Construction of Expression Plasmid pHGT4-1 for Human GnT-IVa Gene A primer (h1-7F; SEQ ID NO: 25) which introduces an XhoI site into a region upstream of the initiation codon of human GnT-IVa gene and another primer (h1-7R; SEQ ID NO: 26) which is complementary to a region downstream of the termination codon of the gene were synthesized. Using RNA from human liver (Clontech, USA) as a template, the entire gene coding for human GnT-IVa enzyme was amplified by RT-PCR with the above primers. The resultant amplified fragment was inserted in the SrfI site of plasmid pCRScript Amp SK(+) (Stratagene, DNA) in the opposite direction to the transcription of lacZ gene. Using the resultant plasmid, it was confirmed by nucleotide sequence analysis that the amplified fragment encodes the amino acid sequence shown in SEQ ID NO: 24. Further, this plasmid was digested with XhoI and SacI to obtain an XhoI-SacI 1.7 kb fragment. This fragment was inserted bewteen the XhoI and Sacd sites of pSVL vector (Pharmacia, Sweden) to prepare an expression plasmid pHGT4-1 for human GnT-IVa gene.

(2) Introduction of Human GnT-IVa Gene into COS7 Cells

Plasmid pHGT4-1 was introduced into COS7 cells by electroporation. The resultant cells were cultured under 10% $CO_2$ at 37° C. for 72 hours. Then, the cells were harvested, suspended in 100 µl of a buffer (5 mM Tris-HCl, pH 7.5, 2 mM magnesium chloride, 1 mM phenylmethylsulfon yl fluoride), disrupted by sonication, centrifuged at 2000×g for 5 minutes and collect supernatant to obtain a cell extract.

(3) Expression of Human GnT-IVa Gene in COS7 Cells

GnT-IV activity in the cell extract was determined by the method described in Reference Example 2. The results are shown in Table 7. Compared to the extract from cells into which pSVL vector was introduced as a control, the extracts from cells into which plasmid pHGT4-1 was introduced exhibited 21–28 times higher GnT-IV activity per cell. From these results, it was confirmed that GnT-IVa gene shown in SEQ ID NO: 23 encodes the glycosyltransferase GnT-IV. It was also confirmed that human GnT-IVa enzyme can be produced by cultured cells according to this method.

TABLE 7

| Plasmid | Specific Activity (pmol/hr/mg protein) | Activity Ratio |
| --- | --- | --- |
| pSVL | 1037 | 1 |
| pHGT4-1(#1) | 28951 | 28 |
| pHGT4-1(#2) | 21788 | 21 |
| pHGT4-2(#1) | 11024 | 11 |
| pHGT4-2(#2) | 8029 | 8 |

Reaction time: 1.3 hours
Activity ratios are expressed in relation to the total activity of pSVL that is regarded as 1.

Reaction time: 1.3 hours

Activity ratios are expressed in relation to the total activity of pSVL that is regarded as 1.

EXAMPLE 7

Isolation and Identification of Human GnT-IVb cDNA (1) Acquisition of Human GnT-IVa-like Gene by PCR, RT-PCR and 5' RACE (Rapid Amplification of CDNA Ends)

Nucleotide sequences having similarity to the nucleotide sequence of human GnT-IVa gene obtained in Example 3 were searched for in the DNA database GenBank by BLASTN. As a result, Accession Numbers R12057, H10557 and W16571 were found out. Then, primer h2-45F shown in SEQ ID NO: 27 and primer h2-43R shown in SEQ ID NO: 28 were synthesized to perform a PCR using a cDNA library from human brain of Quick Screen Human cDNA Library Panel (Clontech, USA) as a template. The amplified fragment was subcloned into the SrfI site of pCRScript Amp SK(+) (Stratagene, USA) and subjected to analysis of the nucleotide sequence. Also, primer h2-2F shown in SEQ ID NO: 29 and primer h2-1R shown in SEQ ID NO: 30 were synthesized to perform an RT-PCR using total RNA from human lung (Clontech, USA) as a template. As a result, an amplified fragment of about 500 bp of the expected size was obtained. Then, this fragment was subcloned into the SrfI site of pCRScript Amp SK(+) (Stratagene, USA) and subjected to analysis of the nucleotide sequence.

The thus obtained nucleotide sequences of the two DNA fragments were overlapping with each other forming a region of 1006 bp. In this region, one reading frame which encodes the homologous amino acid sequences to those of bovine and human GnT-IVa was recognized. Thus, the existence of a protein relating to GnT-IVa proteins was suggested.

Then, possible nucleotide sequences which may be an upstream sequence to R12057 or a downstream sequence to W16571 were searched for in the DNA database GenBank by BLASTN. As a result, R15554 was found as an upstream sequence to R12057, and W16466 as a downstream sequence to W16571. However, a apparently inappropriate termination codon was contained in the ORFs deduced from these nucleotide sequences. Therefore, in order to confirm the nucleotide sequences, DNA fragments were obtained by RT-PCR. As primers, h2-1F shown in SEQ ID NO: 31, h2-3F shown in SEQ ID NO: 32 and h2-8R shown in SEQ ID NO: 33 were synthesized. With a combination of h2-1F and the h1-1R described in Example 5, or a combination of h2-3F and h2-8R, an RT-PCR was performed using total RNA from human liver (Clontech, USA) as a template. Amplified fragments of about 550 bp and about 300 bp, both coinciding with the expected sizes, were detected. Each of these fragments was subcloned in the SrfI site of pCRScript Amp SK(+) to analyze the nucleotide sequence thereof. As a result, it was confirmed that these fragments are respectively overlapping with an upstream region and a downstream region to the 1006 bp region between h2-45F and h2-1R mentioned above. In the ligated region of 1361 bp, an ORF was found which encodes 433 amino acids protein having high similarity to the amino acid sequences of bovine and human GnT-IVa proteins.

However, when this ORF is compared to the amino acid sequences of GnT-IVa proteins, it was presumed that the starting methionine should be present in a region upstream to this ORF. Therefore, the upstream region was obtained by 5'-RACE using Human Lung 5'-RACE-Ready cDNA (Clontech, USA). In the first PCR, an anchor primer and h2-5R shown in SEQ ID NO: 34 were used as primers. In the second PCR, an anchor primer and h2-3R shown in SEQ ID NO: 35 were used as primers. The fragments obtained by 5'-RACE were purified, digested with ECORI and PstI, and then separated by agarose gel electrophoresis. A fragment of about 450 bp was recovered from the gel. This fragment was inserted between the EcoRI and PstI sites of pUC18 vector (Pharmacia, Sweden) to analyze the nucleotide sequence thereof. As a result, it was confirmed that this fragment is overlapping with a region upstream of the region between h2-1F and h2-8R. In the ligated region of 1758 bp, one ORF was confirmed which encodes 548 amino acids protein having high similarity to the amino acid sequences of bovine and human GnT-IVa proteins. The nucleotide sequence of this ORF is shown in SEQ ID NO: 36, and the amino acid sequence thereof in SEQ ID NO: 37. From the results described in Example 8 below, it was confirmed that this gene is human GnT-IVb gene.

EXAMPLE 8

Construction of an Expression Plasmid for Human GnT-IVb Gene and a Method for Producing Human GnT-IVb Enzyme (1) Construction of Expression Plasmid pHGT4-2 for Human GnT-IVb Gene A primer (h2-4: SEQ ID NO: 38) which introduces an XhoI site into a region upstream of the initiation codon of human GnT-IVb gene, and another primer (h2-10R: SEQ ID NO: 39) which introduces an XbaI site in a region downstream to the termination codon of the above gene were synthesized. Using these primers, the entire ORF coding for human GnT-IVb enzyme was amplified by RT-PCR with RNA from human lung (Clontech, USA) as a template. The amplified fragment was inserted into the SrfI site of plasmid pCRScript Amp SK(+), followed by determination of the nucleotide sequence thereof. As a result, it was confirmed that the amplified fragment is coding for the amino acid sequence of SEQ ID NO: 37. Further, this plasmid was digested with XhoI and XbaI to obtain an XhoI-XbaI 1.7 kb fragment. This fragment was inserted between the XhoI and XbaI sites of pSVL vector (Pharmacia, Sweden) to construct an expression plasmid pHGT4-2 for human GnT-IVb gene.

(2) Introduction of Human GnT-IVb Gene into COS7 Cells

Plasmid pHGT4-2 was introduced into COS7 cells by electroporation. The resultant cells were cultured under 10% $CO_2$ at 37° C. for 72 hours. Then, the cells were recovered, suspended in 100 μl of a buffer (5 mM Tris-HCl, pH 7.5, 2 mM magnesium chloride, 1 mM phenyl-methylsulfonyl fluoride), disrupted by sonication, centrifuged at 2000×g for 5 minutes and collect supernatant to thereby obtain a cell extract.

(3) Expression of Human GnT-IVb Gene in COS7 Cells

GnT-IV activity in the cell extract was determined by the method described in Reference Example 2. The results are shown in Table 7 above. Compared to the extract from cells into which pSVL vector was introduced as a control, the extracts from cells into which plasmid pHGT4-2 was introduced exhibited 8–11 times higher GnT-IV activity per cell. From these results, it was confirmed that the GnT-IVb gene shown in SEQ ID NO: 36 encodes the glycosyltransferase GnT-IV. It was also confirmed that human GnT-IVb enzyme can be produced by cultured cells according to this method.

EXAMPLE 9

Construction of Expression Plasmids for Bovine GnT-IVa N-Terminal Deletion Mutants and their Expression of (1) Construction of Expression Plasmids pSigIle93, pSigPro113 and pSigPro142 for Bovine GnT-IVa A primer (XhoEsig: SEQ ID NO:40) which introduces an XhoI site into a region upstream of the signal sequence of human erythropoietin (GenBank Accession Number X02157) and an antisense primer (E4-1R: SEQ ID NO:41) which ligates the C-terminus of the above signal sequence to a part of the bovine GnT-IVa amino acid sequence spanning from position 93 (Ile) to the end were synthesized to amplify the signal sequence of human erythropoietin by PCR. Also, a sense primer (E4-1F: SEQ ID NO:42) corresponding to the above antisense primer and a primer (4EXPR: SEQ ID NO:20) which introduces an XbaI site in a region downstream of the termination codon of bovine GuT-IVa gene were synthesized to amplify a partial sequence of bovine GnT-IVa gene by PCR. Using portions of the resultant two PCR products as a mixed template, a PCR was performed with primers XhoEsig and 4EXPR. The amplified fragment was digested with XhoI and XbaI and inserted between the XhoI and XbaI sites of pSVL vector (Pharmacia, Sweden), to thereby construct plasmid pSigIle93 that expresses an amino acid sequence in which the human erythropoietin signal is linked to a part of the bovine GnT-IVa amino acid sequence spanning from position 93 to the end.

Plasmid pSigPro113 that expresses an amino acid sequence in which the human erythropoietin signal is linked to a part of the bovine GnT-IVa amino acid sequence spanning from position 113 (Pro) to the end; or plasmid pSigPro142 that expresses an amino acid sequence in which the human erythropoietin signal is linked to a part of the bovine GnT-IVa amino acid sequence spanning from position 142 (Pro) to the end was constructed respectively in the same manner as described above using E4-2R primer (SEQ ID NO:43) or E4-3R primer (SEQ ID NO:44) instead of E4-1R primer; and E4-2F primer (SEQ ID NO:45) or E4-3F primer (SEQ ID NO:46) instead of E4-1F primer.

(2) Introduction of plasmids expressing Bovine GnT-IVa N-Terminal Deletion Mutants into COS7 Cells Plasmid pSigIle93, pSigPro113 or pSigPro142 was introduced into COS7 cells by electroporation. The resultant cells were cultured under 10% $CO_2$ at 37° C. for 72 hours. Then, the cells and the culture supernatant were recovered separately. The cells were suspended in 100 μl of a buffer (5 mM Tris-HCl, pH 7.5, 2 mM magnesium chloride, 1 mM phenylmethylsulfonyl fluoride), disrupted by sonication and centrifuged at 2000×g for 5 minutes to thereby obtain a cell extract. The culture supernatant was concentrated to about 100 μl with Centriplus 30 (Amicon).

(3) Expression of Bovine GnT-IVa N-Terminal Deletion Mutants in COS7 Cells

GnT-IV activity in the culture supernatant and the cell extract was determined by the method described in Reference Example 2. The results are shown in Table 8. Compared to the total activity (i.e., activity in cells+activity in supernatant) of the cells into which pBGT4 vector was introduced as a positive control, the total activity of the cells into which pSigIle93 was introduced was more than 30%. Furthermore, more than one third of the activity was secreted into the culture supernatant. From these results, it was found that the amino acids from the N-terminus to position 92 of the bovine GnT-IVa amino acid sequence can be deleted while retaining the enzyme activity. It was also shown that GnT-IVa enzyme can be expressed secretively by using an appropriate secretion signal.

TABLE 8

| Plasmid | Fraction | Activity (pmol/hr) | Activity Ratio in Each Fraction (%) | Total Activity Ratio (%) |
|---|---|---|---|---|
| pSVL | Supernatant | 136 | 0.5 | 1.9 |
| pSVL | Cells | 384 | 1.4 | |
| pBGT4 | Supernatant | 722 | 2.7 | 100.0 |
| pBGT4 | Cells | 26152 | 97.3 | |
| pSigIle93 | Supernatant | 3106 | 11.6 | 31.9 |
| pSigIle93 | Cells | 5471 | 20.4 | |
| pSigPro113 | Supernatant | 312 | 1.2 | 3.4 |
| pSigPro113 | Cells | 606 | 2.3 | |
| pSigPro142 | Supernatant | 219 | 0.8 | 2.2 |
| pSigPro142 | Cells | 381 | 1.4 | |

Reaction time: 2.5 hours
The activity ratios are expressed in percent in relation to the total activity of pBGT4 that is regarded as 100%.

EXAMPLE 10

Construction of Expression Plasmids for Bovine GnT-IVa C-Terminal Deletion Mutants and their Expression (1) Construction of Expression Plasmids pCGly499, pCPro465, pCLys432 and pCPro383 for Bovine GnT-IVa A primer (SEQ ID NO:19) which introduces an XhoI site into a region upstream of the initiation codon of bovine GnT-IVa gene and a primer (CGly499: SEQ ID NO:47) which ligates the termination codon after the Gly codon at position 499 and introduce an XbaI site in a region downstream to the termination codon above were synthesized to amplify a partial sequence of bovine GnT-IVa gene by PCR. The amplified fragment was digested with XhoI and XbaI, and inserted between the XhoI and XbaI sites of pSVL vector (Pharmacia, Sweden). Thus, plasmid pCGly499 which expresses the bovine GnT-IVa amino acid sequence up to position 499 (Glycine) was constructed. Using CPro465 primer (SEQ ID NO:48), CLys432 primer (SEQ ID NO:49) or CPro383 primer (SEQ ID NO:50) instead of CGly499 primer, three additional plasmids were constructed in the same manner. They were designated pCPro465 (plasmid which expresses the bovine GnT-IVa amino acid sequence up to position 465 (Proline)); pCLys432 (plasmid which expresses the bovine GnT-IVa amino acid sequence up to position 432 (Lysine)); and pCPro383 (plasmid which expresses the bovine GnT-IVa amino acid sequence up to position 383 (Proline)), respectively.

(2) Introduction of plasmids expressing Bovine GnT-IVa C-Terminal Deletion Mutants into COS7 Cells Plasmid pCGly499, pCPro465, pCLys432 or pCPro383 was introduced into COS7 cells by electroporation. The resultant cells were cultured under 10% $CO_2$ at 37° C. for 72 hours. Then, the cells were recovered and suspended in 100 µl of a buffer (5 mM Tris-HCl, pH 7.5, 2 mM magnesium chloride, 1 mM phenylmethylsulfonyl fluoride), disrupted by sonication and centrifuged at 2000×g for 5 minutes to thereby obtain a cell extract.

(3) Expression of Bovine GnT-IVa C-Terminal Deletion Mutants in COS7 Cells

GnT-IV activity in the cell extract was determined by the method described in Reference Example 2. The results are shown in Table 9. Compared to the GnT-IV activity of the extract from cells into which PBGT4 vector was introduced as a positive control, that activity of the extract from cells into which pCGly499, pCPro465, pCLys432 or pCPro383 was introduced was 15.2%, 12.1%, 2.8% or 104.2% per cell, respectively. From these results, it was shown that GnT-IV activity can be retained even if the amino acids from position 384 to the C-terminus in the bovine GnT-IVa amino acid sequence are deleted.

TABLE 9

| Plasmid | Specific Activity (pmol/hr/mg protein) | Activity Ratio (%) |
| --- | --- | --- |
| pSVL | 77 | 1 |
| pBGT4 | 14917 | 100 |
| pCGly499 | 2263 | 15 |
| pCPro465 | 1798 | 12 |
| pCLys432 | 410 | 3 |
| pCPro383 | 15551 | 104 |

Reaction Time: 2 hours
Activity ratios are expressed in percent in relation to the total activity of pBGT4 which is regarded as 100%.

EXAMPLE 11

Construction of Plasmids to Express various GnT-IV Genes in *E. coli* and their Expression (1) Construction of *E. coli* Expression Plasmid for Bovine GnT-IVa A primer (BSP-N: SEQ ID NO:51) which introduces a BspHI site in a region upstream of the initiation codon of bovine GnT-IVa gene and another primer (C-Hd: SEQ ID NO:52) which introduces a HindIII site in a region downstream of the termination codon were synthesized to amplify the entire open reading frame of bovine GnT-IVa gene by PCR. The amplified fragment was digested with BspHI and HindIII, and introduced between the NcoI and HindIII sites of pTrc99A vector (Pharmacia, Sweden) to thereby construct plasmid pEBGT4. Using BSP-sN primer (SEQ ID NO:53) instead of BSP-N primer together with C-Hd primer, plasmid pEIle93 was constructed in a similar manner. Further, a gene coding for the open reading frame in which His-Tag is added to the C-terminus was amplified using BSP-N primer, a primer (CH-Hd: SEQ ID NO:54) which can introduce His-Tag, a termination codon and a HindIII site in a region downstream of the C-terminus of bovine GnT-IVa gene and a primer (H-Hd: SEQ ID NO:55) which has His-Tag, a termination codon and a HintdIII site, to thereby construct plasmid pEBGT4+His in a similar manner.

(2) Construction of *E. coli* Expression Plasmid for Human GnT-IVa Gene and Human GnT-IVb Gene A primer (4aBSPIL94: SEQ ID NO:56) which introduces an initiation codon and an Ile codon in a region upstream of position 94 (Leu) of the human GnT-IVa amino acid sequence and which can also introduce a BSPHI site at a region further upstream thereof; a primer (4aCH-Hd: SEQ ID NO: 57) which introduces His-Tag, a termination codon and a HindIII site in a region downstream of the C-terminal amino acid; and H-Hd primer were synthesized to amplify a gene fragment composed a partial sequence of the human GnT-IVa amino acid sequence to which a sequence encoding His-Tag is added. The amplified fragment was digested with BspHI and HindIII, and inserted between the Nco I and HindIII sites of pTrc99A vector (Pharmacia, Sweden) to thereby construct plasmid pMA4a+His. Further, using CP383H-Hd primer (SEQ ID NO:58) instead of 4aCH-Hd primer, plasmid pCore+His was constructed in a similar manner (FIG. 18). A fragment of human GnT-IVb gene was amplified using a primer (4bBSP-N: SEQ ID NO:59) which introduces a Bsp HI site in a region upstream of the initiation codon of human GnT-IVb gene and 4bSACR primer (SEQ ID No: 60), digested with BspHI and Sac I, and then inserted between the Nco I and Sac I sites of pTrc99A vector (Pharmacia, Sweden). Between the SacI and HindIII sites of the resultant plasmid, a partial length of human GnT-IVb gene amplified using 4bSACF primer (SEQ ID NO:61), a primer (4bCH-Hd: SEQ ID NO: 62) which introduces His-Tag at the C-terminus of the human GnT-IVb amino acid sequence and H-Hd primer, and digested with Sac I and HindIII was inserted to thereby achieve plasmid pEHGT4-2+His. Further, a partial sequence of human GnT-IVb gene was amplified using a primer (4bNCOG91: SEQ ID NO:63) which introduces an Nco I site and an initiation codon in a region upstream of position 91 (Gly) of the human GnT-IVb amino acid sequence, 4bCH-Hd primer and H-Hd primer, digested with Nco I and HindIII, and then inserted between the Nco I and HindIII sites of pTrc99A vector (Pharmacia, Sweden) to thereby construct plasmid pMA4b+His.

(3) Introduction of Each Expression Plasmid into *E. coli* BL21 Strain

Each expression plasmid was introduced into competent cells of *E. coli* BL21 strain prepared by the calcium method. The resultant cells were cultured on LB agar plate containing 100 µg/ml ampicillin. The resultant colonies of *E. coli* transformed with each plasmid were inoculated into LB liquid medium and cultured under shaking at 37° C. overnight. Then, the culture was inoculated into a fresh LB liquid medium to give a concentration of 2%. While the turbidity (OD 595 nm) of the culture fluid was about 0.1 to 0.2, IPTG (isopropyl b-D-thiogalactopyranoside) was added thereto to give a final concentration of 1 mM. The cells were cultured at 37° C. for 2 hours or at 25° C. for 4 hours. Then, 500 µl of the cells was harvested. The cell pellet was suspended in 50 μl of a buffer (5 mM Tris-HCl, pH 7.5, 2 mM $MgCl_2$, 1 mM phenylmethylsulfonyl fluoride), disrupted by sonication and centrifuged at 2000×g for 5 minutes to obtain a cell extract as a supernatant.

(4) Expression of Each Expression Plasmid in *E. coli* BL21 Strain GnT-IV activity in the cell extract was determined by the method described in Reference Example 2. Table 10 shows the results of the expression of the bovine gene. Although the extract from *E. coli* cells into which pTrc99A vector was introduced as a control had little GnT-IV, the extract from *E. coli* cells into which pEBGT4 was introduced had definite GnT-IV activity. From these results, it was demonstrated that GnT-IV enzyme can be produced by *E. coli*. The His-tag sequence added to the C-terminus of bovine GnT-IVa did not influence greatly upon GnT-IV activity. Thus, it was shown that an appropriate tag sequence can be added to GnT-IV enzyme. The mutant (pEIle93) in which the N-terminal 92 amino acid are deleted exhibited stronger GnT-IV activity. Thus, the expression of variants of GnT-IV enzyme which was confirmed in animal cells was also shown possible in *E. coli*.

TABLE 10

| Plasmid | Activity (pmol/hr/mg protein) | Activity Ratio (%) |
| --- | --- | --- |
| pTrc99A | 0 | 0 |
| pEBGT4 | 4611 | 100 |
| pEBGT4 + His | 3090 | 67 |
| pEIle93 | 5841 | 127 |

Reaction time: 3.0 hours
After IPTG addition, cells were cultured at 37° C. for 2 hours.
Activity ratios are expressed in percent in relation to the total activity of pEBGT4 which is regarded as 100%.

Table 11 shows the results of the expression of the human gene. Compared to the extract from *E. coli* cells into which pTrc99A vector was introduced as a control, the extract from *E. coli* cells into which any of the expression plasmids was introduced had GnT-IV activity significantly. As shown in bovine GnT-IVa enzyme, it was also possible in human GnT-IVa and GnT-IVb enzymes to delete an N-terminal sequence while retaining the activity. Further, the human GnT-IVa enzyme which has both N-terminal deletion and C-terminal deletion exhibited high GnT-IV activity (pCore+ His). This shows that those portions deleted in this mutant are not essential for GnT-IV activity.

TABLE 11

| Plasmid | Activity (pmol/hr/mg protein) | Activity Ratio (%) |
| --- | --- | --- |
| pTrc99A | 0 | 0 |
| pEBGT4 + His | 21390 | 637 |
| pMA4a + His | 3359 | 100 |
| pCore + His | 39766 | 1184 |
| pEHGT4-2 + His | 270 | 8 |
| pMA4b + His | 2812 | 84 |

Reaction time: 4.0 hours
After IPTG addition, cells were cultured at 25° C. for 4 hours.
Activity ratios are expressed in percent in relation to the total activity of pMA4a + His which is regarded as 100%.

EXAMPLE 12

Conversion of the Sugar Chain Branching Structure of a Recombinant Erythropoietin (EPO) by Introducing Bovine or Human, GnT-IVa Gene into EPO-Producing CHO Cells (1) Introduction of GnT-IVa Expression Plasmid into EPO-Producing CHO Cells EPO-producing CHO cell clones were created according to the method disclosed in Japanese Examined Patent Publication.No. 2-17156. GnT-IVa expression plasmid pBGT4 or pHGT4-1 was introduced into the resultant cell clones Mo1 and H-5 by electroporation. In the introduction, 15 μg of the expression plasmid and 1.5 μg of a drug resistance marker plasmid (pSv2bsr from Kaken Pharmaceutical or pMAMneo from Clontech) were used in mixture. The electroporated cells were cultured under 10% $CO_2$ at 37° C. for about 60 hours. Then, blasticidin S (Kaken Pharmaceuticals) (final concentration: 10 μg/ml) or geneticin (Life Technologies, Inc.) (final concentration: 500 μg/ml) was added to the medium, in which the cells were cultured for another 10 days to 2 weeks. Thus, clones resistant to either of two drugs were isolated.

(2) Confirmation of the Expression of the Introduced GnT-IVa Genes in EPO-Producing CHO Cell Clones EPO-producing CHO cell clones (initial clones) and individual drug resistant clones were cultured in an appropriate scale. Total RNA from each clone was purified. Then, RNA dot blot analysis was performed using a part of GnT-IVa gene as a probe to thereby examine the amount of GnT-IVa mRNA. Further, GnT-IV activity expressed in the initial clones and the drug resistant clones was determined by the assay described in Reference Example 2. Those clones which gave a strong signal in RNA dot blot analysis and yet exhibited higher GnT-IV activity than the initial clones were selected and used for EPO production. The selected clones had increased GnT-IV activity; for example, MO1 (bovine GnT-IVa) #36 exhibited about 104-fold increase over MO1 clone, and H-5(human GnT-IVa) #23 exhibited about 125-fold increase over H-5 clone.

(3) Production of EPO using GnT-IVa Gene-Introduced EPO-Producing CHO Cell Clones EPO is expressed secretively into culture fluid. Then, EPO-producing CHO cell clones MO1 and H-5, and the above-mentioned clones MO1 (bovine GnT-IVa) #36 and H-5(human GnT-IVa) #23 were cultured in roller bottles. First, each clone was adhesion-cultured in a growth medium, and then $1.5 \times 10^7$ cells were transferred to a 850 $cm^2$ roller bottle containing 200 ml of a growth medium. The cells were cultured under 10% $CO_2$ at 37° C. for 3 days so that they adhered to the bottle uniformly. Thereafter, the growth medium was removed, and the cells were washed with PBS buffer. Then, 200 ml of a serum-free medium was added to the bottle, in which the cells were cultured under 10% $CO_2$ at 37° C. for 7 days. Thereafter, the culture supernatant was recovered.

As a growth medium, D-MEM/F12 mixed medium supplemented with 5% fetal bovine serum, 290 mg/liter L-glutamic acid, 1×MEM non-essential amino acid solution and 100 nM methotrexate was used. As a serum-free medium, the above medium without fetal bovine serum was used. EPO contained in each of the serum-free culture supernatants was quantitatively determined by ELISA usig anti-human EPO antibody.

(4) Analysis of EPOs Produced by GnT-IVa Gene-Introduced or -Non-Introduced Clones Based on Their Sugar Chain Structures A recombinant EPO does not exist as a single molecule on isoelectric focusing gel; it is mixture of molecules with various electric charges. Since the protein moiety does not vary, it has been shown that the difference in electric charge among these molecules is based on the difference in sugar chain structure; such mixture of molecules is called glycoforms [Watson, E. and Yao, F., Anal. Biochem. (1993), 210, 389–93]. EPO has three Asn-linked sugar chains; the branching structures of individual sugar chains vary from biantennary to tetraantennary. Gal (galactose) is further attaching to the end of each of branched GlcNAc's, and sialic acid is further attaching to this Gal. Therefore, if the degree of sugar chain branching is increased by the introduction of GnT-IVa gene, the number of sialic acid molecules attaching to Gal should increase and, thus, the content of glycoforms with low isoelectric point should increase. Then, the inventors performed analysis by isoelectric focusing to detect changes in the sugar chain structure of the EPOs produced by GnT-IVa gene-introduced EPO-producing cells.

For the isoelectric focusing, Multiphor II equipment manufactured by Pharmacia was used. The gel was composed of 5% acrylamide (30: 0.8) and 1.5% Pharmalyte 2.5–5 (Pharmacia). As the (+) electrode solution, 0.1 M sulfuric acid was used. As the (−) electrode solution, 0.2 M L-histidine was used. After the isoelectric focusing, samples were electrophoretically transferred onto a PVDF membrane, followed by Western blot analysis using anti-EPO mouse monoclonal antibody to detect the bands of individual glycoforms of the EPOs. Briefly, the serum-free culture supernatant of each cell clone was concentrated to about 7 to 1000-fold with Centriplus 30 and Microcon 30 (both manufactured by Amicon), if necessary. At the beginning, about 50–100 IU of EPO was used as a sample, but this amount was adjusted appropriately so that the intensities of bands detected by Western blot analysis would be almost equal between samples.

When the EPO from MO1 clone was compared to the EPO from MO1 (bovine GnT-IVa) #36 clone, it was confirmed that the positions of major glycoforms in the latter show a shift to the low pI side (+electrode solution side) by at least one glycoporm (FIG. 19). From this result, it is thought that the GnT-IVa enzyme expressed as a result of the gene introduction increased the number of GlcNAc branches in the Asn-linked sugar chains attaching to EPO, thus increasing the number of sialic acid molecules attaching to increase the content of glycoforms with low isoelectric points. A similar analysis was performed on H-5 clone and H-5(human GnT-IVa )#23 clone. As a result, it was also found that the positions of major EPO glycoforms in the latter shift to the low pI side (FIG. 19).

From the above, it was demonstrated that it is possible to modify the structure of Ans-linked sugar chains of the protein produced by the cell by introducing a GnT-IVa gene into any cell.

Industrial Applicability

According to the present invention, a novel β1→4 N-acetyl-glucosaminyltransferase (GnT-IV), a method for producing the GnT-IV enzyme and a gene coding for the GnT-IV are provided. With the GnT-IV of the present invention, it has become possible to produce a glycocoujugate having a branching structure which could not be formed with conventional glycosyltransferases. Thus, the GnT-IV of the invention is useful not only for producing or improving glycoconjugate type pharmaceuticals, reagents and foods, but also for modifying the sugar chain structure of any biopolymer.

The GnT-IV gene of the invention is also useful for diagnosing or treating diseases such as cancer and for modifying the sugar chain structure of glycoconjugate products produced by microorganisms.

Further, an antibody or anti-serum raised against the GnT-IV protein of the invention as an antigen, or a part or all of the GnT-IV gene of the invention as a probe is useful for characterizing microorganisms, cultured cells, various animal tissues, blood cells and blood or for diagnosing diseased cells or tissues such as cancer.

What is claimed is:

1. An isolated and purified DNA coding for a protein which comprses an amino acid sequence daving at least 96% homology to the amino acid sequence shown in SEQ ID NO:24 and has β1,4 N-acetylglucosaminyltransferase-IV (GnT-IV) activity.

2. The DNA of claim 1, wherein the DNA encodes a protein comprising an amino acid sequence of residues 94 to 383 of SEQ ID NO:24.

3. The DNA of claim 1, wherein the DNA encodes a protein comprising the amino acid sequence of SEQ ID NO:24.

4. An isolated and purified DNA coding for a protein which comprises an amino acid sequence having at least 96% homology to the amino acid sequence shown in SEQ ID NO:37 and that has β1,4 N-acetylglucosaminyltransferase-IV (GnT-IV) activity.

5. The DNA of claim 4, wherein the DNA encodes a protein comprising an amino acid sequence of residues 91 to 548 of SEQ ID NO:37.

6. The DNA of claim 4, wherein the DNA encodes a protein comprising the amino acid sequence of SEQ ID NO:37.

7. An isolated and purified DNA coding for a protein which comprises an amino acid sequence having at least 96% homology to the amino acid sequence shown in SEQ ID NO:18 and that has β1,4 N-acetylglucosaminyltransferase-IV (GnT-IV) activity.

8. The DNA of claim 7, wherein the DNA encodes a protein comprising an amino acid sequence of residues 94 to 383 of SEQ ID NO:18.

9. The DNA of claim 7, wherein the DNA encodes a protein comprising the amino acid sequence of SEQ ID NO:18.

10. An isolated and purified GnT-IV enzyme-encoding DNA comprising the nucleotide sequence shown in SEQ ID NO:17.

11. An isolated and purified GnT-IV enzyme-encoding DNA comprising the nucleotide sequence shown in SEQ ID NO:23.

12. An isolated and purified GnT-IV enzyme-encoding DNA comprising the nucleotide sequence shown in SEQ ID NO:36.

13. A GnT-IV enzyme purified to homogeneity which is encoded by the DNA of claim 1.

14. A GnT-IV enzyme purified to homogeneity which is encoded by the DNA of claim 2.

15. A GnT-IV enzyme purified to homogeneity which is encoded by the DNA of claim 3.

16. A GnT-IV enzyme purified to homogeneity which is encoded by the DNA of claim 4.

17. A GnT-IV enzyme purified to homogeneity which is encoded by the DNA of claim 5.

18. A GnT-IV enzyme purified to homogeneity which is encoded by the DNA of claim 6.

19. A GnT-IV enzyme purified to homogeneity which is encoded by the DNA of claim 7.

20. A GnT-IV enzyme purified to homogeneity which is encoded by the DNA of claim 8.

21. A GnT-IV enzyme purified to homogeneity which is encoded by the DNA of claim 9.

22. A GnT-IV enzyme purified to homogeneity which is encoded by the DNA of claim 10.

23. A GnT-IV enzyme purified to homogeneity which is encoded by the DNA of claim 11.

24. A GnT-IV enzyme purified to homogeneity which is encoded by the DNA of claim 12.

25. A recombinant DNA obtained by inserting into a vector DNA, a DNA segment coding for the GnT-IV enzyme of claim 13.

26. A recombinant DNA obtained by inserting into a vector DNA, a DNA segment coding for the GnT-IV enzyme of claim 14.

27. A recombinant DNA obtained by inserting into a vector DNA, a DNA segment coding for the GnT-IV enzyme of claim 15.

28. A recombinant DNA obtained by inserting into a vector DNA, a DNA segment coding for the GnT-IV enzyme of claim 16.

29. A recombinant DNA obtained by inserting into a vector DNA, a DNA segment coding for the GnT-IV enzyme of claim 17.

30. A recombinant DNA obtained by inserting into a vector DNA, a DNA segment coding for the GnT-IV enzyme of claim 18.

31. A recombinant DNA obtained by inserting into a vector DNA, a DNA segment coding for the GnT-IV enzyme of claim 19.

32. A recombinant DNA obtained by inserting into a vector DNA, a DNA segment coding for the GnT-IV enzyme of claim 20.

33. A recombinant DNA obtained by inserting into a vector DNA, a DNA segment coding for the GnT-IV enzyme of claim 21.

34. A recombinant DNA obtained by inserting into a vector DNA, a DNA segment coding for the GnT-IV enzyme of claim 22.

35. A recombinant DNA obtained by inserting into a vector DNA, a DNA segment coding for the GnT-IV enzyme of claim 23.

36. A recombinant DNA obtained by inserting into a vector DNA, a DNA segment coding for the GnT-IV enzyme of claim 24.

37. A host cell comprising a foreign DNA encoding a GnT-IV enzyme of claim 13.

38. A host cell comprising a foreign DNA encoding a GnT-IV enzyme of claim 14.

39. A host cell comprising a foreign DNA encoding a GnT-IV enzyme of claim 15.

40. A host cell comprising a foreign DNA encoding a GnT-IV enzyme of claim 16.

41. A host cell comprising a foreign DNA encoding a GnT-IV enzyme of claim 17.

42. A host cell comprising a foreign DNA encoding a GnT-IV enzyme of claim 18.

43. A host cell comprising a foreign DNA encoding a GnT-IV enzyme of claim 19.

44. A host cell comprising a foreign DNA encoding a GnT-IV enzyme of claim 20.

45. A host cell comprising a foreign DNA encoding a GnT-IV enzyme of claim 21.

46. A host cell comprising a foreign DNA encoding a GnT-IV enzyme of claim 22.

47. A host cell comprising a foreign DNA encoding a GnT-IV enzyme of claim 23.

48. A host cell comprising a foreign DNA encoding a GnT-IV enzyme of claim 24.

49. A method for producing a GnT-IV enzyme comprising culturing the host cell of claim 37 in a medium and recovering the GnT-IV enzyme from the resultant culture.

50. A method for producing a GnT-IV enzyme comprising culturing the host cell of claim 38 in a medium and recovering the GnT-IV enzyme from the resultant culture.

51. A method for producing a GnT-IV enzyme comprising culturing the host cell of claim 39 in a medium and recovering the GnT-IV enzyme from the resultant culture.

52. A method for producing a GnT-IV enzyme comprising culturing the host cell of claim 40 in a medium and recovering the GnT-IV enzyme from the resultant culture.

53. A method for producing a GnT-IV enzyme comprising culturing the host cell of claim 41 in a medium and recovering the GnT-IV enzyme from the resultant culture.

54. A method for producing a GnT-IV enzyme comprising culturing the host cell of claim 42 in a medium and recovering the GnT-IV enzyme from the resultant culture.

55. A method for producing a GnT-IV enzyme comprising culturing the host cell of claim 43 in a medium and recovering the GnT-IV enzyme from the resultant culture.

56. A method for producing a GnT-IV enzyme comprising culturing the host cell of claim 44 in a medium and recovering the GnT-IV enzyme from the resultant culture.

57. A method for producing a GnT-IV enzyme comprising culturing the host cell of claim 45 in a medium and recovering the GnT-IV enzyme from the resultant culture.

58. A method for producing a GnT-IV enzyme comprising culturing the host cell of claim 46 in a medium and recovering the GnT-IV enzyme from the resultant culture.

59. A method for producing a GnT-IV enzyme comprising culturing the host cell of claim 47 in a medium and recovering the GnT-IV enzyme from the resultant culture.

60. A method for producing a GnT-IV enzyme comprising culturing the host cell of claim 48 in a medium and recovering the GnT-IV enzyme from the resultant culture.

61. A method for modifying the branching structure of a sugar chain of a glycoprotein produced by a host cell, comprising introducing into the host cell a DNA of claim 25.

62. A method for modifying the branching structure of a sugar chain of a glycoprotein produced by a host cell, comprising introducing into the host cell a DNA of claim 26.

63. A method for modifying the branching structure of a sugar chain of a glycoprotein produced by a host cell, comprising introducing into the host cell a DNA of claim 27.

64. A method for modifying the branching structure of a sugar chain of a glycoprotein produced by a host cell, comprising introducing into the host cell a DNA of claim 28.

65. A method for modifying the branching structure of a sugar chain of a glycoprotein produced by a host cell, comprising introducing into the host cell a DNA of claim 29.

66. A method for modifying the branching structure of a sugar chain of a glycoprotein produced by a host cell, comprising introducing into the host cell a DNA of claim 30.

67. A method for modifying the branching structure of a sugar chain of a glycoprotein produced by a host cell, comprising introducing into the host cell a DNA of claim 31.

68. A method for modifying the branching structure of a sugar chain of a glycoprotein produced by a host cell, comprising introducing into the host cell a DNA of claim 32.

69. A method for modifying the branching structure of a sugar chain of a glycoprotein produced by a host cell, comprising introducing into the host cell a DNA of claim 33.

70. A method for modifying the branching structure of a sugar chain of a glycoprotein produced by a host cell, comprising introducing into the host cell a DNA of claim 34.

71. A method for modifying the branching structure of a sugar chain of a glycoprotein produced by a host cell, comprising introducing into the host cell a DNA of claim 35.

72. A method for modifying the branching structure of a sugar chain of a glycoprotein produced by a host cell, comprising introducing into the host cell a DNA of claim 36.

* * * * *